(12) United States Patent
Chan et al.

(10) Patent No.: US 10,584,133 B2
(45) Date of Patent: Mar. 10, 2020

(54) THIENOPYRIMIDINONE COMPOUNDS

(71) Applicant: BioTheryX, Inc., Chappaqua, NY (US)

(72) Inventors: Kyle W. H. Chan, San Diego, CA (US); Aparajita Hoskote Chourasia, San Diego, CA (US); Paul E. Erdman, San Diego, CA (US); Leah Fung, San Diego, CA (US); Imelda Lam, San Diego, CA (US); Frank Mercurio, Rancho Santa Fe, CA (US); Robert Sullivan, Vista, CA (US); Eduardo Torres, San Diego, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

(21) Appl. No.: 16/368,409

(22) Filed: Mar. 28, 2019

(65) Prior Publication Data

US 2019/0322682 A1  Oct. 24, 2019

Related U.S. Application Data

(60) Provisional application No. 62/650,922, filed on Mar. 30, 2018.

(51) Int. Cl.
*C07D 495/04* (2006.01)
*A61P 35/00* (2006.01)

(52) U.S. Cl.
CPC ............ *C07D 495/04* (2013.01); *A61P 35/00* (2018.01)

(58) Field of Classification Search
CPC ............................. C07D 495/04; A61P 35/00
USPC ....................................................... 544/278
See application file for complete search history.

(56) References Cited

U.S. PATENT DOCUMENTS

| | | | |
|---|---|---|---|
| 5,334,596 A | 8/1994 | Hartman | |
| 6,476,052 B1* | 11/2002 | Muller | A61K 31/445 514/323 |
| 8,524,742 B2* | 9/2013 | Zhang | C07D 495/04 514/321 |
| 9,260,448 B2 | 2/2016 | Choo | |
| 9,273,068 B2 | 3/2016 | Geneste | |
| 9,670,212 B2 | 6/2017 | Leahy | |
| 10,040,804 B2* | 8/2018 | Chan | A61P 11/00 |
| 10,336,771 B2* | 7/2019 | Chan | A61P 25/28 |
| 10,406,165 B2* | 9/2019 | Chan | A61K 31/55 |
| 2005/0176738 A1 | 8/2005 | Goodfellow | |
| 2012/0230983 A1* | 9/2012 | Muller | A61K 45/06 424/133.1 |
| 2014/0314753 A1 | 10/2014 | Hege et al. | |
| 2017/0145028 A1 | 5/2017 | Ghosh | |
| 2018/0170948 A1* | 6/2018 | Chan | C07D 519/00 |
| 2018/0264000 A1* | 9/2018 | Chan | C07D 403/04 |
| 2018/0298027 A1* | 10/2018 | Chan | A61P 35/00 |

FOREIGN PATENT DOCUMENTS

| | | |
|---|---|---|
| WO | WO 98/02162 | 1/1998 |
| WO | WO 03/076400 | 9/2003 |
| WO | WO 05/030704 | 4/2005 |
| WO | WO 17/075182 | 5/2017 |
| WO | WO 17/120446 | 7/2017 |

OTHER PUBLICATIONS

Chemical Abstracts STN Registry Database, record for RN 1495719-95-3, entered on Dec. 15, 2013. (Year: 2013).*
Hagner; Blood 2015, 126, 779-789. (Year: 2015).*
Ballell et al., 2013, Fueling Open-Source Drug Discovery: 177 Small-Molecule Leads against Tuberculosis, ChemMedChem, 8(2):313-321.
Brito et al., 2005, Polyglycine expansions in eRFs/GSPT1 are associated with gastric cancer susceptibility, Carcinogenesis, 26(12):2046-2049.
Carey, 1992, Organic Chemistry, 2d ed., McGraw-Hill, Inc., New York, pp. 328-331.
Chauvin et al., Aug. 2007, Human eukaryotic release factor 3a depletion causes cell cycle arrest at $G_1$ phase through inhibition of the mTOR pathway, Mol. Cell. Bio., 27(16):5619-5629.
Desagher et al., Sep. 2001, Phosphorylation of bid by casein kinases I and II regulates its cleavage by caspase 8, Molecular Cell., 8:601-611.
Hashimoto et al., 2012, Translation termination factor eRF3 is targeted for caspase-mediated proteolytic cleavage and degradation during DNA damage-induced apoptosis, Apoptosis, 17:1287-1299.
Ishii et al., 2017, A novel Rac1-GSPT1 signaling pathway controls astrogliosis following central nervous system injury, J. Biol. Chem., 292(4):1240-1250.
Knippschild et al., 2005, The casein kinase 1 family: participation in multiple cellular processes in eukaryotes, Cell Signalling, 17:675-689.
Li et al., Jan. 2014, eRF3b, a biomarker for hepatocellular carcinoma, influences cell cycle and phosphoralation status of 4E-BP1, PLOS One, 9(1):e86371, 8 pp.
Malta-Vacas et al., 2009, Differential expression of GSPT1 $GGC_n$ alleles in cancer, Canc. Genet. Cyto., 195:132-142.
Matyskiela et al., Jun. 22, 2016, A novel cereblon modulator recruits GSTP1 to the CRL4 CRBN ubiquitin ligase (includes methods), Nature, 535:252-257.
McMurry, 2000, Organic Chemistry, 5th Edition, Brooks/Cole, Pacific Grove, CA, pp. 398 and 408.
Miri et al., 2011, $GGC_n$ polymorphism of eRF3a/GSPT1 gene and breast cancer susceptibility, Med. Oncol., 29:1581-1585.
Netea et al., 2009, Differential requirement for the activation of the inflammasome for processing and release of IL-1β in monocytes and macrophages, Blood, 113(10):2324-2335 (2009).
Streitweiser et al., 1981, Introduction to Organic Chemistry, 2d ed., Macmillan Publishing Co., Inc., New York, pp. 169-171.
Wallach, 2013, The TNF cytokine family: one track in a road paved by many, Cytokine, 63:225-229.
Wright et al., 2007, Newer potential biomarkers in prostate cancer, Rev. Urol., 9(4):207-213.

(Continued)

*Primary Examiner* — Daniel R Carcanague

(74) *Attorney, Agent, or Firm* — Knobbe, Martens, Olson & Bear, LLP

(57) ABSTRACT

The present disclosure provides compounds that modulate protein function and/or restore protein homeostasis. The disclosure provides methods of modulating protein-mediated diseases, disorders, conditions, or responses. Compositions, including in combination with other therapeutic agents, are provided.

44 Claims, No Drawings

(56) References Cited

OTHER PUBLICATIONS

Zhang et al., 2007, Thienopyrimidinone bis-aminopyrrolidine ureas as potent melanin-concentrating hormone receptor-1 (MCH-R1) antagonists, Bloorganic & Medicinal Chemistry Letters, 17(9):2535-2539.
International Search Report and Written Opinion dated May 24, 2019 in application No. PCT/US2019/024612.

* cited by examiner

THIENOPYRIMIDINONE COMPOUNDS

INCORPORATION BY REFERENCE TO PRIORITY APPLICATION

The present application claims the benefit of priority to U.S. Provisional Application No. 62/650,922, filed Mar. 30, 2018, which is hereby incorporated by reference in its entirety.

BACKGROUND

Field

Compounds, methods of making such compounds, pharmaceutical compositions and medicaments comprising such compounds, and methods of using such compounds to treat, prevent or diagnose diseases, disorders, or conditions associated with protein malfunction are provided.

Description of the Related Technology

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Misregulation of protein synthesis may contribute to uncontrolled cell growth, proliferation, and migration, leading to cancer. For example, the translation termination factor GSPT1 (eRF3a) mediates stop codon recognition and facilitates release of a nascent peptide from the ribosome. In addition to its role in translation termination, GSPT1 is also involved in several other critical cellular processes, such as cell cycle regulation, cytoskeleton organization and apoptosis. GSPT1 has been implicated as an oncogenic driver of several different cancer types, including breast cancer, hepatocellular carcinoma, gastric cancer, and prostate cancer. See, e.g., Brito, et al., *Carcinogenesis*, Vol. 26, No. 12, pp. 2046-49 (2005); Brito, et al., *Canc. Genet. Cyto.*, Vol. 195, pp. 132-42 (2009); Tavassoli, et al., *Med. Oncol.*, Vol. 29, pp. 1581-85 (2011); Wright and Lange, *Rev. Urol.*, Vol. 9, No. 4, pp. 207-213 (2007); Hoshino, et al., *Apoptosis*, Vol. 17, pp. 1287-99 (2012); Liu, et. al., PLOS One, Vol. 9, No. 1, e86371 (2014); and Jean-Jean, et al., *Mol. Cell. Bio.*, Vol. 27, No. 16, pp. 5619-29 (2007). GSPT1 also contributes to glial scar formation and astrogliosis after a central nervous system (CNS) injury. See, e.g., Ishii et al., *J. Biol. Chem.*, Vol. 292, No. 4, pp. 1240-50 (2017).

Tumor necrosis factor-alpha (TNF-alpha) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others.

TNF-alpha is produced by variety of activated immune cells, particularly monocytes and macrophages. Elevated levels of TNF-alpha have been implicated in several pathological conditions including inflammation, infection, autoimmune disease, cancer development and several other disorders. Indeed, virtually all of the players in the human immune system have been report to have some level of functional relationship with TNF-alpha. See, e.g., Wallach, Cytokine, Vol. 63, 225-9 (2013). TNF is able to induce fever, apoptotic cell death, cachexia, inflammation, and to inhibit tumorigenesis and viral replication.

IL-1α and IL-1β are proinflammatory cytokines that activate cells by binding the IL-1 receptor type I (IL-1RI). These proteins are the most powerful endogenous pyrogens known. IL-1α is constitutively expressed as a precursor in cells forming biological barriers, such as epithelial cells, keratinocytes, and mucosal and endothelial cells, as well as other organ cells. IL-1α does not require processing for activation and is released from damaged or dying cells. In contrast, IL-1β must be proteolytically cleaved into its active form. Active IL-1β is primarily generated in a subset of blood monocytes, dendritic cells, and tissue macrophages, where its activation and release are tightly regulated, although studies systematically assessing other cells capable of producing IL-1β are limited. See, e.g., Nold, et al., Blood, Vol. 113, 2324-35 (2009).

Recent data from clinical trials support the use of protein antagonists of cytokines, for example soluble TNF-alpha receptor fusion protein (etanercept) or the monoclonal TNF-alpha antibody (infliximab), for the treatment of rheumatoid arthritis, Crohn's disease, juvenile chronic arthritis and psoriatic arthritis. Thus, the reduction of pro-inflammatory cytokines such as TNF-alpha and interleukin-1 (IL-I) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including the zinc-finger transcription factor Aiolos. Aiolos is a transcription factor whose expression is restricted to lymphoid lineages. Aiolos binds to the Bcl-2 promoter, and also interacts with the Bcl-2 and Bcl-XL proteins to promote cell survival. Upregulation of Aiolos expression, for example, can reduce apoptosis of HIV-1 infected cells.

Likewise, expression of Aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Thus, down-regulation of Aiolos may reduce or eliminate metastasis.

Similarly, the casein kinase 1 family of proteins plays a role in the mitotic spindle formation, in DNA repair, and in RNA metabolism. See, e.g., Knippschild, et al., Cell Signal, Vol 17, pp. 675-689 (2005). There are six isoforms in humans: α, γ1, γ2, γ3, δ and ε. CK1α has been shown to have an anti-apoptotic function; its inhibition increased Fas-induced apoptosis, whereas the overexpression of CK1α delayed BID-mediated cell death. See, e.g., Desagher, et al., Mol Cell., Vol. 8, pp. 601-611 (2001). In addition, CK1α inhibits TRAIL induced apoptosis by modification of the TNF receptor or FADD at the death-inducing signaling complex (DISC). Thus, downregulation of CK1α leads to enhancement of TRAIL-induced cell death. CK1α also promotes cell survival by interacting with the retinoid X receptor (RXR). Downregulation of CK1α enhances the apoptotic effect of RXR agonists. Likewise, the ikaros family of proteins are tumor suppressors that play a role in leukemia.

One mechanism to disrupt protein drivers of disease is to decrease the cellular concentration of these proteins. For example, proteolytic degradation of cellular proteins is essential to normal cell function. Hijacking this process, by targeting specific disease-related proteins, presents a novel mechanism for the treatment of disease. The irreversible nature of proteolysis makes it well-suited to serve as a regulatory switch for controlling unidirectional processes.

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. The E3 ligases confer specificity to ubiquitination reactions by binding directly to particular substrates.

SUMMARY

The compounds disclosed in the present application have been discovered to exert surprising and unexpected biological effects. In particular, the compounds disclosed in the present application modulate protein function and/or modulate protein levels to restore protein homeostasis. Some embodiments provide compounds comprising an E1-binding group, an E-2 binding group, an E-3 binding group, or a combination thereof.

Some embodiments provide a compound of Formula (I):

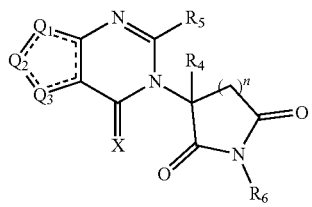

(I)

or a pharmaceutically acceptable salt or solvate thereof, wherein $Q_1$ is $CR_1$ or —S—;

$Q_2$ is $CR_2$ or —S—;

$Q_3$ is $CR_3$ or —S—;

wherein one of $Q_1$, $Q_2$, and $Q_3$ is —S—;

each $\equiv\equiv\equiv$ is a single or double bond;

each of $R_1$, $R_2$, and $R_3$ is independently hydrogen, deuterium, hydroxyl, halogen, cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_1$-$C_6$ haloalkyl, a substituted or unsubstituted $C_3$-$C_8$ cycloalkyl, a substituted or unsubstituted $C_6$-$C_{10}$ aryl, a substituted or unsubstituted 3-10 membered heterocyclyl, or a substituted or unsubstituted 5-10 membered heteroaryl;

each of $R_4$ and $R_5$ is independently selected from the group consisting of hydrogen, deuterium, halogen, and a substituted or unsubstituted $C_1$-$C_6$ alkyl;

$R_6$ is selected from the group consisting of hydrogen, deuterium, hydroxy, a substituted or unsubstituted $C_1$-$C_6$ alkyl, and a substituted or unsubstituted $C_1$-$C_6$ alkoxy;

X is O, NH, or S; and n is 1, 2, or 3.

Some such embodiments of the compounds of Formula (I) may be further represented by Formula (Ia):

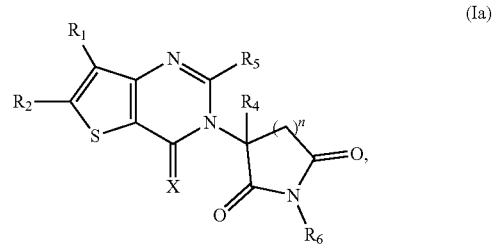

(Ia)

or Formula (Ib)

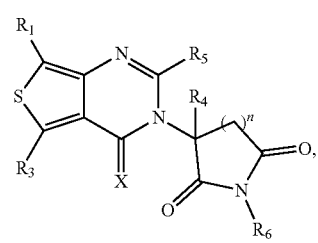

(Ib)

or Formula (Ic):

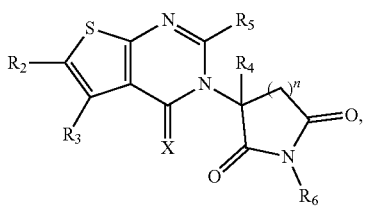

or a pharmaceutically acceptable salt thereof.

Other embodiments provide a compound of Formula (II):

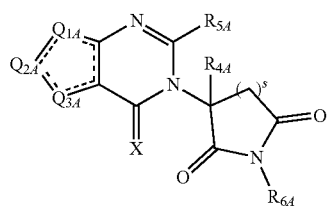

or a pharmaceutically acceptable salt or solvate thereof, wherein $Q_{1A}$ is $CR_{1A}$ or —S—;

$Q_{2A}$ is $CR_{2A}$ or —S—;

$Q_{3A}$ is $CR_{3A}$ or —S—;

each ═══ is a single or double bond;

wherein one of $Q_1$, $Q_2$, and $Q_3$ is —S—;

each of $R_{1A}$, $R_{2A}$, and $R_{3A}$ is independently hydrogen, deuterium, hydroxyl, halogen, cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_1$-$C_6$ haloalkyl, a substituted or unsubstituted $C_3$-$C_8$ cycloalkyl, a substituted or unsubstituted $C_6$-$C_{10}$ aryl, a substituted or unsubstituted 3-10 membered heterocyclyl, a substituted or unsubstituted 5-10 membered heteroaryl,

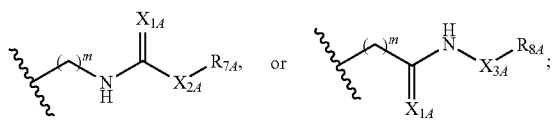

wherein at least one of $R_{1A}$, $R_{2A}$, and $R_{3A}$ is

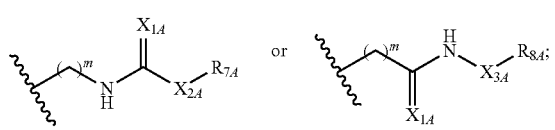

each of $R_{4A}$ and $R_{5A}$ is independently selected from the group consisting of hydrogen, deuterium, halogen, and a substituted or unsubstituted $C_1$-$C_6$ alkyl;

$R_{6A}$ is selected from the group consisting of hydrogen, deuterium, hydroxy, a substituted or unsubstituted $C_1$-$C_6$ alkyl, and a substituted or unsubstituted $C_1$-$C_6$ alkoxy;

$X_A$ is O, NH, or S;

s is 1, 2, or 3;

each $X_{1A}$ is independently O, NH, or S;

each $X_{2A}$ is independently selected from the group consisting of —$NR_{9A}$—, —$(CH_2)_h$—$(NR_{9A})$—$(CH_2)_i$—, —$(CH_2)_h$—$(NR_{9A})$—$(CH_2)_i$—$(NR_{9A})$—, —$(CH_2)_{1-5}$—, —$(CF_2)_{1-5}$—, —$(CD_2)_{1-5}$—, —O—, —C(═O)—, and —S—;

each $X_{3A}$ is independently selected from the group consisting of —$(CH_2)_t$—$(NR_{9A})$—$(CH_2)_j$—, —$(CH_2)_t$—$(NR_{9A})$—$(CH_2)_j$—$(NR_{9A})$—, —$(CH_2)_{1-5}$—, —$(CF_2)_{1-5}$—, and —$(CD_2)_{1-5}$—;

each m is independently 0, 1, 2, 3, 4, or 5;

each h, i, and j is independently 0, 1, 2, 3, 4, or 5;

each t is independently 1, 2, 3, 4, or 5;

each $R_{7A}$ and $R_{8A}$ is independently selected from the group consisting of a substituted or unsubstituted $C_3$-$C_{10}$ cycloalkyl, a substituted or unsubstituted $C_6$-$C_{10}$ aryl, a substituted or unsubstituted 5-10 membered heteroaryl, a substituted or unsubstituted 3-10 membered heterocyclyl, and a substituted or unsubstituted $C_1$-$C_{10}$ alkyl; and $R_{9A}$ is hydrogen, or a substituted or unsubstituted $C_1$-$C_6$ alkyl.

Some such embodiments of the compounds of Formula (II) may be further represented by Formula (IIa):

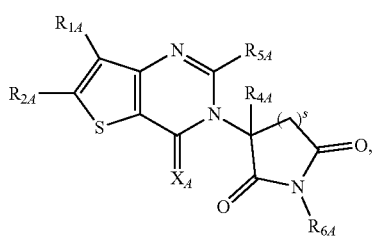

or Formula (IIb):

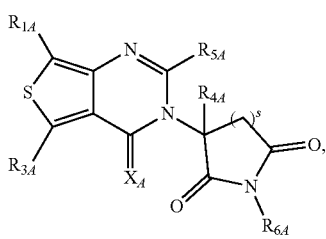

or Formula (IIc):

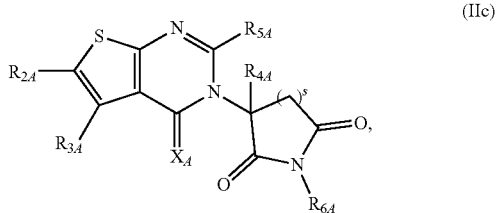

(IIc)

or a pharmaceutically acceptable salt thereof.

Still other embodiments provide a pharmaceutical composition comprising a compound of Formula (I), a compound of Formula (II), or a pharmaceutically acceptable salt of any of the foregoing, and one or more pharmaceutically acceptable excipients.

Some embodiments provide a method of treating, ameliorating, or preventing a disease, disorder, or condition associated with GSPT1, comprising administering a therapeutically effective amount of a compound of Formula (I), a compound of Formula (II), or a pharmaceutically acceptable salt of any of the foregoing, or a pharmaceutical composition comprising a compound of Formula (I), a compound of Formula (II), or a pharmaceutically acceptable salt of any of the foregoing.

Other embodiments provide a method of treating, ameliorating, or preventing a disease, disorder, or condition associated with one or more proteins, comprising administering a therapeutically effective amount of a compound of Formula (I), a compound of Formula (II), or a pharmaceutically acceptable salt of any of the foregoing, or a pharmaceutical composition comprising a compound of Formula (I), a compound of Formula (II), or a pharmaceutically acceptable salt of any of the foregoing. In some such embodiments of the method, the one or more proteins are selected from the group consisting of cytokine, aiolos, phosphodiesterase (PDE) (such as PDE6), ikaros, helios, and CK1α, and combinations thereof. In some embodiments, the one or more proteins are selected from the group consisting of cytokine, aiolos, ikaros, helios, and CK1α. In some embodiments, the protein is a cytokine selected from the group consisting of IL-1β, IL-6, TNFα, and IL-2.

Still other embodiments provide a method of decreasing the risk of skin cancer in a subject in need thereof, comprising administering a therapeutically effective amount of a compound of Formula (I), a compound of Formula (II), or a pharmaceutically acceptable salt of any of the foregoing, or a pharmaceutical composition comprising a compound of Formula (I), a compound of Formula (II), or a pharmaceutically acceptable salt of any of the foregoing.

Some embodiments provide a method for treating, ameliorating, or preventing a skin disorder, disease, or condition in a subject, comprising administering a therapeutically effective amount of a compound of Formula (I), a compound of Formula (II), or a pharmaceutically acceptable salt of any of the foregoing, or a pharmaceutical composition comprising a compound of Formula (I), a compound of Formula (II), or a pharmaceutically acceptable salt of any of the foregoing.

Other embodiments provide a method of increasing skin pigmentation or increasing eumelanin levels in a subject in need thereof, comprising administering a therapeutically effective amount of a compound of Formula (I), a compound of Formula (II), or a pharmaceutically acceptable salt of any of the foregoing, or a pharmaceutical composition comprising a compound of Formula (I), a compound of Formula (II), or a pharmaceutically acceptable salt of any of the foregoing.

Some embodiments provide a method of inhibiting GSPT1 activity, comprising contacting a cell with a compound of Formula (I), a compound of Formula (II), or a pharmaceutically acceptable salt of any of the foregoing.

Other embodiments provide a method of modulating protein activity, comprising contacting a cell with a compound of Formula (I), a compound of Formula (II), or a pharmaceutically acceptable salt thereof. In some such embodiments, the protein is selected from the group consisting of a cytokine, aiolos, phosphodiesterase (PDE) (such as PDE6), ikaros, helios, and CK1α. In some such embodiments, the method inhibits protein activity. In some other embodiments, the method stimulates or activates protein activity.

Still other embodiments provide a method of increasing p53 activity, comprising contacting a cell with a compound of Formula (I), a compound of Formula (II), or a pharmaceutically acceptable salt of any of the foregoing.

Some embodiments provide a method of decreasing MDM2 activity, comprising contacting a cell with a compound of Formula (I), a compound of Formula (II), or a pharmaceutically acceptable salt of any of the foregoing.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

DETAILED DESCRIPTION

The section headings used herein are for organizational purposes only and are not to be construed as limiting the subject matter described.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:

| | |
|---|---|
| ° C. | Temperature in degrees Centigrade |
| DCM | Dichloromethane (methylene chloride) |
| DMSO | Dimethylsulfoxide |
| EA | Ethyl acetate |
| g | Gram(s) |
| h or hr | H(s) |
| HCl | Hydrochloric acid |
| HOBt | Hydroxybenzotriazole |
| IL | Interleukin |
| LPS | Lipopolysaccharide |
| MeOH | Methanol |
| MS | Mass spectrometry |
| mg | Milligram(s) |
| mL | Milliliter(s) |
| NaCl | Sodium chloride |
| NaOH | Sodium hydroxide |
| NBS | N-Bromosuccinimide |
| PBMC | Peripheral blood mononuclear cell |
| PG | Protecting group |
| ppt | Precipitate |
| psi | Pounds per square inch |
| RPMI | Roswell Park Memorial Institute medium |
| rt | Room temperature |
| TNF | Tumor necrosis factor |
| μL | Microliter(s) |
| μM | Micromolar |
| wt. | weight |

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

The term "pharmaceutical combination" as used herein is a broad term, and is to be given its ordinary and customary meaning to a person of ordinary skill in the art (and is not to be limited to a special or customized meaning), and refers without limitation to a product that results from the mixing or combining of more than one active ingredient and includes both fixed and non-fixed combinations of the active ingredients. The term "fixed combination" means that the active ingredients, e.g., a compound of a preferred embodiment and a co-agent, are both administered to a patient simultaneously in the form of a single entity or dosage. The term "non-fixed combination" means that the active ingredients, e.g., a compound of a preferred embodiment and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

As used herein, any "R" group(s) such as, without limitation, $R_2$, $R_3$, $R_4$, $R_5$, $R_6$, $R_9$, and $R_{10}$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring:

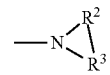

Whenever a group is described as being "optionally substituted" that group may be unsubstituted or substituted with one or more of the indicated substituents. Likewise, when a group is described as being "unsubstituted or substituted" if substituted, the substituent may be selected from one or more of the indicated substituents. If no substituents are indicated, it is meant that the indicated "optionally substituted" or "substituted" group may be individually and independently substituted with one or more group(s) individually and independently selected from alkyl, alkenyl, alkynyl, cycloalkyl, cycloalkenyl, cycloalkynyl, aryl, heteroaryl, heterocyclyl, aralkyl, heteroaralkyl, heterocyclyl (alkyl), hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heterocyclyl group. That is, the alkyl, alkenyl, alkynyl, ring of the cycloalkyl, ring of the cycloalkenyl, ring of the cycloalkynyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, (CH₃)₂CH—, CH₃CH₂CH₂CH₂—, CH₃CH₂CH(CH₃)— and (CH₃)₃C—. If no "a" and "b" are designated with regard to an alkyl, alkenyl, alkynyl, cycloalkyl cycloalkenyl, cycloalkynyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "carbocyclyl" refers to a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Multicyclic carbocyclyl groups can include, for example, a non-aromatic hydrocarbon ring fused to an aromatic hydrocarbon ring. Examples of carbocyclyl groups include, but are in no way limited to, cycloalkyl groups and cycloalkenyl groups, as defined herein, as well as 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., the ring system is not aromatic). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

"Lower alkylene groups" are straight-chained —$CH_2$— tethering groups, forming bonds to connect molecular fragments via their terminal carbon atoms. Lower alkylene groups contain from 1 to 6 carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "aralkyl" and "aryl(alkyl)" refer to an aryl group, as defined above, connected, as a substituent, via a lower alkylene group, as described above. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group, as defined above, connected, as a substituent, via a lower alkylene group, as defined above. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "heterocyclyl(alkyl)" is a heterocyclic or a heterocyclyl group, as defined above, connected, as a substituent, via a lower alkylene group, as defined above. The lower alkylene and heterocyclyl groups of a heterocyclyl(alkyl) may be substituted or unsubstituted. Examples include but are not limited to tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

As used herein, "alkoxy" refers to the formula OR wherein R is an alkyl, an alkenyl, an alkynyl, a cycloalkyl, a cycloalkenyl or a cycloalkynyl, as defined above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "acyl" refers to a hydrogen, alkyl, alkenyl, alkynyl, or aryl, as defined above, connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—"group wherein X is a halogen.

A "trihalomethanesulfonamido" group refers to an "$X_3CS(O)_2N(R_A)$—" group wherein X is a halogen and $R_A$ hydrogen, alkyl, alkenyl, alkynyl, cycloalkyl, cycloalkenyl, cycloalkynyl, aryl, heteroaryl, heterocyclyl, aralkyl, or heterocyclyl(alkyl).

The terms "amino" and "unsubstituted amino" as used herein refer to a —$NH_2$ group. The term "mono-substituted amino group" as used herein refers to an amino (—$NH_2$) group where one of the hydrogen atom is replaced by a substituent. The term "di-substituted amino group" as used herein refers to an amino (—$NH_2$) group where each of the two hydrogen atoms is replaced by a substituent. In some embodiment, the substituent may be independently alkyl, alkenyl, alkynyl, cycloalkyl, cycloalkenyl, cycloalkynyl, aryl, heteroaryl, heterocyclyl, aralkyl, or heterocyclyl(alkyl), as defined herein.

An "(alkyl)amine is an alkyl group, as defined herein, connected to a —$NR_AR_B$ group, wherein $R_A$ can be hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined herein; and $R_B$ can be alkyl, alkenyl, alkynyl, cycloalkyl, cycloalkenyl, cycloalkynyl, aryl, heteroaryl, heterocyclyl, aralkyl, or heterocyclyl(alkyl), as defined herein. The alkyl portion of the (alkyl) amine, includes, for example, $C_1$-$C_6$ alkyl groups. Examples of (alkyl)amine groups include, but are not limited to methylamino, ethylamino, n-propylamino,

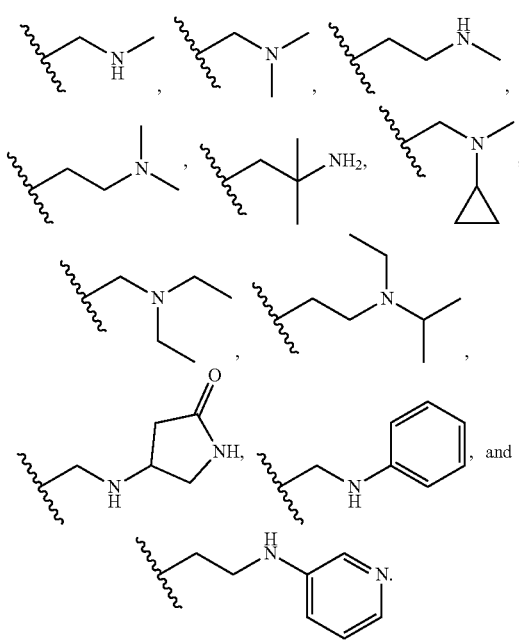

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or heterocyclyl (alkyl), as defined above. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heterocyclyl, aralkyl, or heterocyclyl (alkyl), as defined above. An N-sulfonamido may be substituted or unsubstituted.

An "O-carbamyl" group refers to a "—OC(=O)N($R_AR_B$) "group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or heterocyclyl (alkyl), as defined above. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An 0-thiocarbamyl may be substituted or unsubstituted.

An "N-thiocarbamyl" group refers to an "ROC(=S)N($R_A$)—"group in which R and $R_A$ can be independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or heterocyclyl (alkyl), as defined above. A C-amido may be substituted or unsubstituted.

An "N-amido" group refers to a "RC(=O)N($R_A$)—"group in which R and $R_A$ can be independently hydrogen, alkyl, alkenyl, alkynyl, cycloalkyl, cycloalkenyl, cycloalkynyl, aryl, heteroaryl, heterocyclyl, aralkyl, or heterocyclyl (alkyl), as defined above. An N-amido may be substituted or unsubstituted.

A "urea" group refers to a "—N($R_AR_B$)—C(=O)—N($R_AR_B$)—" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. A urea group may be substituted or unsubstituted.

A "thiourea" group refers to a "—N($R_AR_B$)—C(=S)—N($R_AR_B$)—" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. A thiourea group may be substituted or unsubstituted.

The term "halogen atom" or "halogen" as used herein, means any one of the radio-stable atoms of column 7 of the Periodic Table of the Elements, such as, fluorine, chlorine, bromine, and iodine.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "solvate" as used herein is a broad term, and is to be given its ordinary and customary meaning to a person of ordinary skill in the art (and is not to be limited to a special or customized meaning), and refers without limitation to mean that the solvent is complexed with a compound in a reproducible molar ratio, including, but not limited to, 0.5:1, 1:1, or 2:1. Thus, the term "pharmaceutically acceptable solvate," refers to a solvate wherein the solvent is one that does not cause significant irritation to an organism to which it is administered and does not abrogate the biological activity and properties of the compound.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

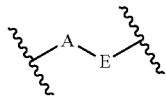

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

Compounds of Formula (I)

Some embodiments provide a compound of Formula (I):

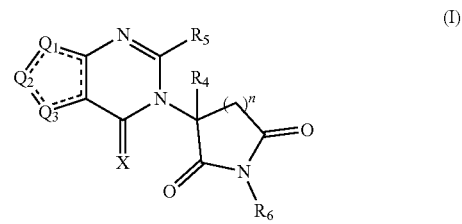

or a pharmaceutically acceptable salt or solvate thereof, as described herein.

In some embodiments, each of $R_1$, $R_2$, and $R_3$ is independently hydrogen, deuterium, hydroxyl, halogen (such as fluoro, chloro, bromo, or iodo), cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy (such as methoxy, ethoxy, n-propoxy, iso-propoxy, n-butoxy, sec-butoxy, t-butoxy, pentoxy (straight chain or branched) and hexoxy (straight chain or branched)), a substituted or unsubstituted $C_1$-$C_6$ alkyl (such as methyl, ethyl, n-propyl, iso-propyl, n-butyl, sec-butyl, t-butyl, pentyl (straight chain or branched) and hexyl (straight chain or branched)), a substituted or unsubstituted $C_2$-$C_6$ alkenyl (such as 1-propene, 2-propene, or 2-butene), a substituted or unsubstituted $C_2$-$C_6$ alkynyl (such as ethynyl or propargyl), a substituted or unsubstituted $C_1$-$C_6$ haloalkyl (such as —$CH_2F$, —$CHF_2$, —$CF_3$, —$CH_2CF_3$, —$CClH_2$, —$CCl_2H$, and —$CCl_3$), a substituted or unsubstituted $C_3$-$C_8$ cycloalkyl (such as cyclopropyl, cyclobutyl, cyclopentyl, cyclohexyl, cycloheptyl, and cyclooctyl), a substituted or unsubstituted $C_6$-$C_{10}$ aryl (such as phenyl and naphthyl), a substituted or unsubstituted 3-10 membered heterocyclyl (such as aziridine, oxirane, azetidine, oxetane, morpholine, piperidine, piperazine, pyrrolidine, azepane, pyrrolidone, pyrrolidione, 4-piperidone, pyrazoline, pyrazolidine, tetrahydropyran, 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane), or a substituted or unsubstituted 5-10 membered heteroaryl (such as furan, furazan, thiophene, benzothiophene, pyrrole, oxazole, benzoxazole, thiazole, benzothiazole, imidazole, benzimidazole, indole, indazole, pyrazole, benzopyrazole, isoxazole, benzoisoxazole, isothiazole, triazole, benzotriazole, pyridine, pyridazine, pyrimidine, pyrazine, purine, quinoline, isoquinoline, quinazoline, and quinoxaline). In some embodiments, at least one of $R_1$, $R_2$, and $R_3$ is not hydrogen.

In some embodiments, when $R_1$, $R_2$, and/or $R_3$ is an substituted 4-6 membered heterocyclyl that contains one or more nitrogen atoms, at least one nitrogen atom may be substituted with hydrogen or a substituted or unsubstituted $C_1$-$C_6$ alkyl; for example, the substituted 4-6 membered heterocyclyl may be

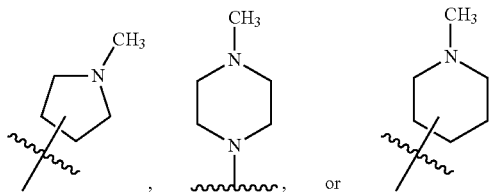

When $R_1$, $R_2$, and/or $R_3$ is an substituted $C_3$-$C_8$ cycloalkyl, $C_3$-$C_8$ cycloalkyl may be substituted with $C_1$-$C_6$ haloalkyl; for example, the substituted $C_3$-$C_8$ cycloalkyl may be

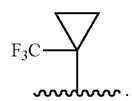

In some embodiments, the compound of Formula (I) is also represented by Formula (Ia)

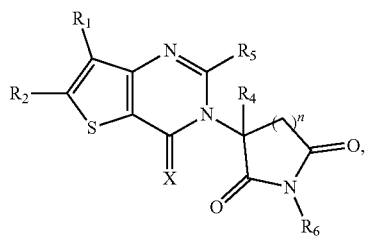

Formula (Ib)

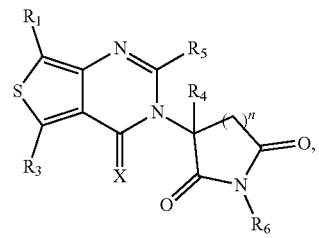

or Formula (Ic)

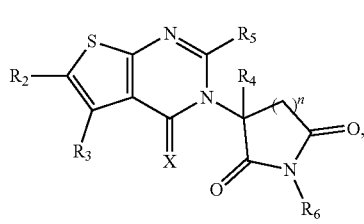

or a pharmaceutically acceptable salt thereof.

In some embodiments, the compound of Formula (I) is a compound of Formula (Ia):

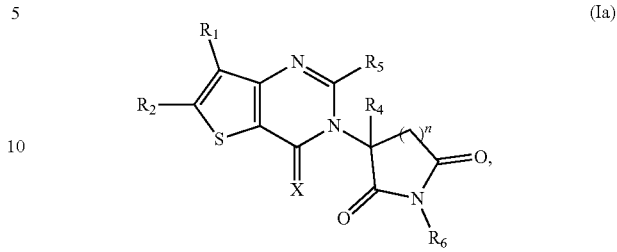

or a pharmaceutically acceptable salt thereof.

In some embodiments, the compound of Formula (I) is a compound of Formula (Ib):

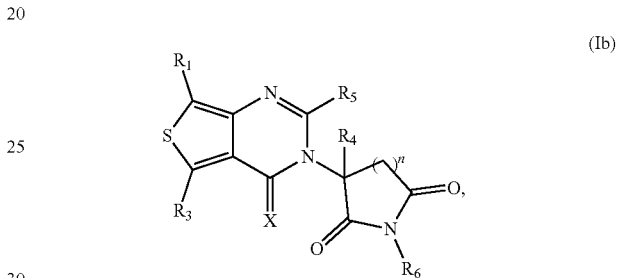

or a pharmaceutically acceptable salt thereof.

In some embodiments, the compound of Formula (I) is a compound of Formula (Ic):

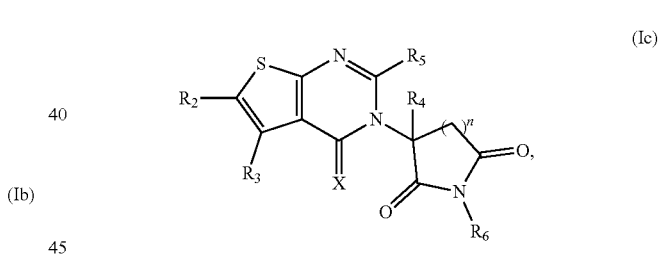

or a pharmaceutically acceptable salt thereof.

In some embodiments of the compound of Formula (I), (Ia), (Ib), or (Ic), n is 1. In some other embodiments, n is 2. In some other embodiments, n is 3.

In some embodiments of the compound of Formula (I), (Ia), (Ib), or (Ic), $R_4$ is hydrogen. In some embodiments, $R_4$ is deuterium. In some embodiments, $R_4$ is halogen. In some embodiments, $R_4$ is fluoro. In some embodiments, $R_4$ is a substituted or unsubstituted $C_1$-$C_6$ alkyl. In some embodiments, $R_4$ is an unsubstituted $C_1$-$C_6$ alkyl.

In some embodiments of the compound of Formula (I), (Ia), (Ib), or (Ic), $R_5$ is hydrogen. In some embodiments, $R_5$ is deuterium. In some embodiments, $R_5$ is halogen. In some embodiments, $R_5$ is fluoro. In some embodiments, $R_5$ is a substituted or unsubstituted $C_1$-$C_6$ alkyl. In some embodiments, $R_5$ is an unsubstituted $C_1$-$C_6$ alkyl.

In some embodiments of the compound of Formula (I), (Ia), (Ib), or (Ic), $R_6$ is hydrogen. In some embodiments, $R_6$ is deuterium. In some embodiments, $R_6$ is a substituted or unsubstituted $C_1$-$C_6$ alkyl. In some embodiments, $R_6$ is an unsubstituted $C_1$-$C_6$ alkyl.

In some embodiments of the compound of Formula (I), (Ia), (Ib), or (Ic), X is O. In some other embodiments, X is NH or S.

In some embodiments of the compound of Formula (I), (Ia), (Ib), or (Ic), $R_1$, $R_2$, and $R_3$ are independently hydrogen, deuterium, hydroxyl, halogen, cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl (such as cyclopropyl, cyclobutyl, cyclopentyl, and cyclohexyl), a substituted or unsubstituted phenyl, a substituted or unsubstituted naphthyl, a substituted or unsubstituted 4-6 membered heterocyclyl (such as oxetane, azetidine, tetrahydrofuran, 2-oxopiperidine, isoxazole, piperazine, tetrahydropyran, piperidine, and morpholine), or a substituted or unsubstituted 5 or 6 membered heteroaryl (such as imidazole, furan, thiophene, oxazole, thiazole, pyrrole, pyridine, pyrimidine, pyrazine, and pyridazine). In some such embodiments, one of $R_1$, $R_2$, and $R_3$ is hydrogen. In some embodiments, two of $R_1$, $R_2$, and $R_3$ are hydrogen.

In some further embodiments of the compound of Formula (I), (Ia), (Ib), or (Ic), $R_1$, $R_2$, and $R_3$ are independently hydrogen, deuterium, hydroxyl, fluoro, chloro, cyano, nitro, an unsubstituted or substituted amino, an unsubstituted $C_1$-$C_3$ alkoxy, an unsubstituted $C_1$-$C_6$ alkyl, a substituted $C_1$-$C_6$ alkyl (substituted with $C_1$-$C_6$ alkoxy, amino, —N($C_1$-$C_3$ alkyl)$_2$, or —NH($C_1$-$C_3$ alkyl)), an unsubstituted $C_1$-$C_3$ haloalkyl (such as —$CF_3$), an unsubstituted $C_3$-$C_6$ cycloalkyl, or an unsubstituted 4-6 membered heterocyclyl. In some such embodiments, each of $R_1$, $R_2$, and $R_3$ is independently hydrogen, deuterium, hydroxyl, halogen, cyano, nitro, —$NH_2$, —N($C_1$-$C_3$ alkyl)$_2$, —NH($C_1$-$C_3$ alkyl), an unsubstituted $C_1$-$C_3$ alkoxy, an unsubstituted $C_1$-$C_3$ alkyl, —$CF_3$, cyclopropyl, unsubstituted or substituted piperidinyl, or unsubstituted or substituted morpholinyl. In some embodiments, $R_1$ and $R_2$, or $R_1$ and $R_3$, or $R_2$ and $R_3$, are both hydrogen. In some embodiments, one of $R_1$ and $R_2$, or one of $R_1$ and $R_3$, or one of $R_2$ and $R_3$, is hydrogen.

In some embodiments, the compound of Formula (I) is represented by Formula (Ia). In some such embodiments, each of $R_1$ and $R_2$ is independently hydrogen, deuterium, hydroxyl, fluoro, chloro, cyano, nitro, amino, —N($C_1$-$C_3$ alkyl)$_2$, —NH($C_1$-$C_3$ alkyl), an unsubstituted $C_1$-$C_3$ alkoxy, an unsubstituted $C_1$-$C_6$ alkyl, a substituted $C_1$-$C_6$ alkyl (substituted with $C_1$-$C_6$ alkoxy, amino, —N($C_1$-$C_3$ alkyl)$_2$, or —NH($C_1$-$C_3$ alkyl)), an unsubstituted $C_1$-$C_3$ haloalkyl (such as —$CF_3$), an unsubstituted or substituted $C_3$-$C_6$ cycloalkyl (such as cyclopropyl, optionally substituted with $C_1$-$C_3$ haloalkyl, e.g., —$CF_3$), or an unsubstituted or substituted 4-6 membered heterocyclyl (such as pyrrolidinyl, piperazinyl, piperidinyl or morpholinyl, each optionally substituted with $C_1$-$C_3$ alkyl, e.g., methyl). In some embodiments, at least one, or both of $R_1$ and $R_2$ is hydrogen. In some other embodiments, at least one of $R_1$ and $R_2$ is not hydrogen. For example, one of $R_1$ and $R_2$ is selected from the group consisting of an unsubstituted $C_1$-$C_3$ alkoxy, an unsubstituted $C_1$-$C_3$ alkyl, an amino substituted $C_1$-$C_3$ alkyl, an unsubstituted $C_1$-$C_2$ haloalkyl, halogen, —$NH_2$, and —NH($C_1$-$C_3$ alkyl).

In some embodiments, the compound of Formula (I) is represented by Formula (Ib). In some such embodiments, each of $R_1$ and $R_3$ is independently hydrogen, deuterium, hydroxyl, fluoro, chloro, cyano, nitro, amino, —N($C_1$-$C_3$ alkyl)$_2$, —NH($C_1$-$C_3$ alkyl), an unsubstituted $C_1$-$C_3$ alkoxy, an unsubstituted $C_1$-$C_6$ alkyl, a substituted $C_1$-$C_6$ alkyl (substituted with $C_1$-$C_6$ alkoxy, amino, —N($C_1$-$C_3$ alkyl)$_2$, or —NH($C_1$-$C_3$ alkyl)), an unsubstituted $C_1$-$C_3$ haloalkyl (such as —$CF_3$), an unsubstituted or substituted $C_3$-$C_6$ cycloalkyl (such as cyclopropyl, optionally substituted with $C_1$-$C_3$ haloalkyl, e.g., —$CF_3$), or an unsubstituted or substituted 4-6 membered heterocyclyl (such as pyrrolidinyl, piperazinyl, piperidinyl or morpholinyl, each optionally substituted with $C_1$-$C_3$ alkyl, e.g., methyl). In some embodiments, at least one, or both of $R_1$ and $R_3$ is hydrogen. In some other embodiments, at least one of $R_1$ and $R_3$ is not hydrogen. For example, one of $R_1$ and $R_3$ is selected from the group consisting of an unsubstituted $C_1$-$C_3$ alkoxy, an unsubstituted $C_1$-$C_3$ alkyl, an amino substituted $C_1$-$C_3$ alkyl, an unsubstituted $C_1$-$C_2$ haloalkyl, halogen, —$NH_2$, and —NH($C_1$-$C_3$ alkyl).

In some embodiments, the compound of Formula (I) is represented by Formula (Ic). In some such embodiments, each of $R_2$ and $R_3$ is independently hydrogen, deuterium, hydroxyl, fluoro, chloro, cyano, nitro, amino, —N($C_1$-$C_3$ alkyl)$_2$, —NH($C_1$-$C_3$ alkyl), an unsubstituted $C_1$-$C_3$ alkoxy, an unsubstituted $C_1$-$C_6$ alkyl, a substituted $C_1$-$C_6$ alkyl (substituted with $C_1$-$C_6$ alkoxy, amino, —N($C_1$-$C_3$ alkyl)$_2$, or —NH($C_1$-$C_3$ alkyl)), an unsubstituted $C_1$-$C_3$ haloalkyl (such as —$CF_3$), an unsubstituted or substituted $C_3$-$C_6$ cycloalkyl (such as cyclopropyl, optionally substituted with $C_1$-$C_3$ haloalkyl, e.g., —$CF_3$), or an unsubstituted or substituted 4-6 membered heterocyclyl (such as pyrrolidinyl, piperazinyl, piperidinyl or morpholinyl, each optionally substituted with $C_1$-$C_3$ alkyl, e.g., methyl). In some embodiments, at least one, or both of $R_1$ and $R_3$ is hydrogen. In some other embodiments, at least one of $R_2$ and $R_3$ is not hydrogen. For example, one of $R_2$ and $R_3$ is selected from the group consisting of an unsubstituted $C_1$-$C_3$ alkoxy, an unsubstituted $C_1$-$C_3$ alkyl, an amino substituted $C_1$-$C_3$ alkyl, an unsubstituted $C_1$-$C_2$ haloalkyl, halogen, —$NH_2$, and —NH($C_1$-$C_3$ alkyl).

In some embodiments, the compound of Formula (I), is selected from the group consisting of:

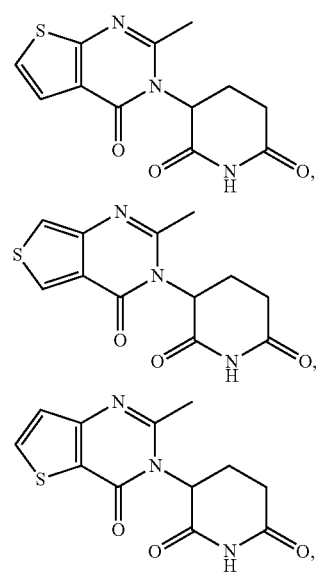

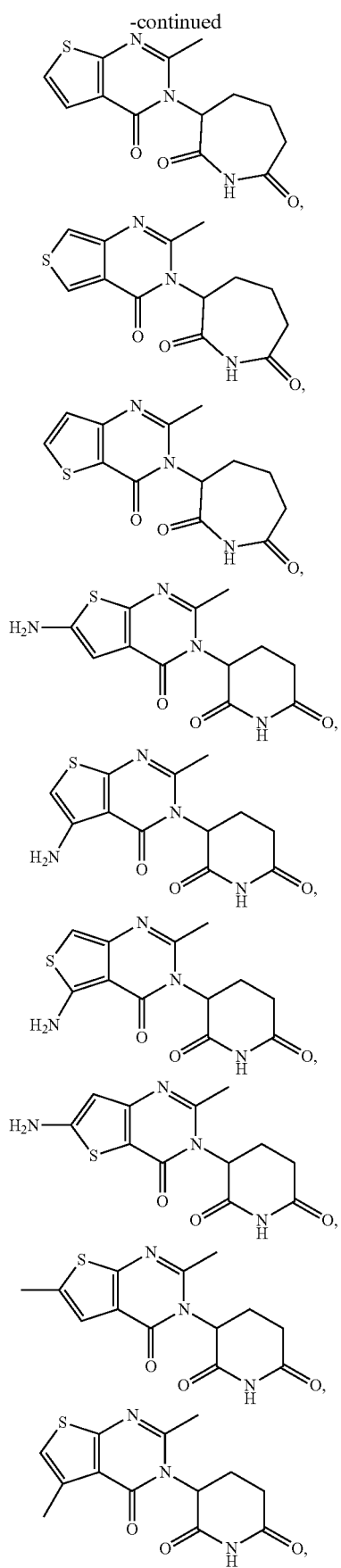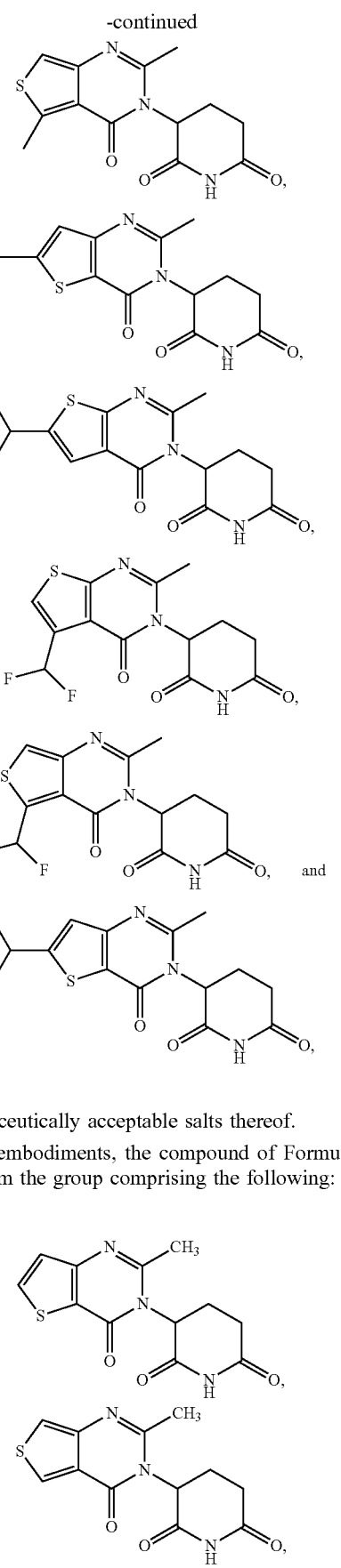
and pharmaceutically acceptable salts thereof.
In some embodiments, the compound of Formula (I) is selected from the group comprising the following:
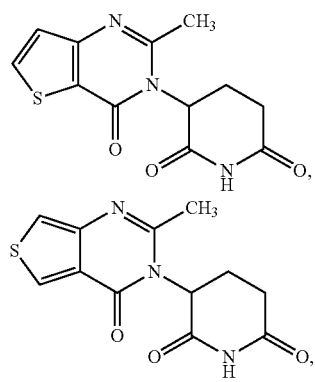

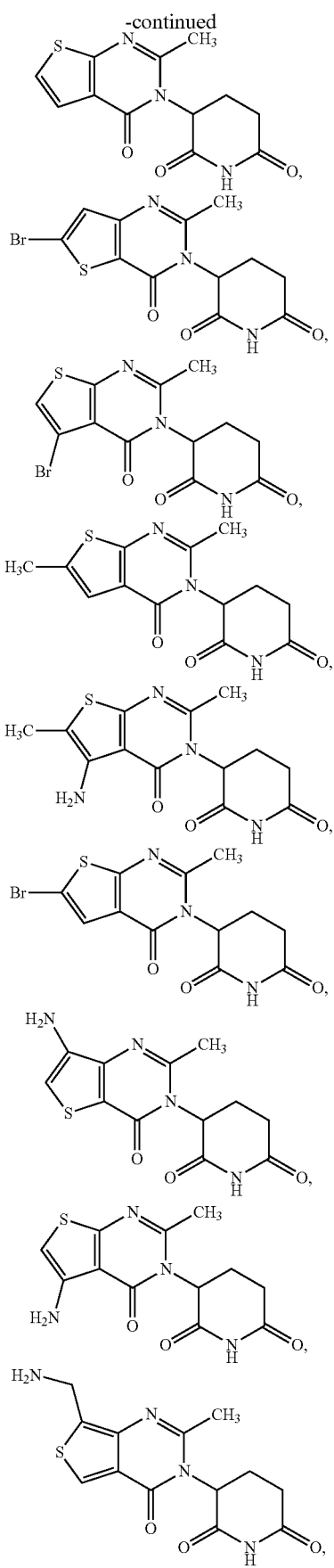

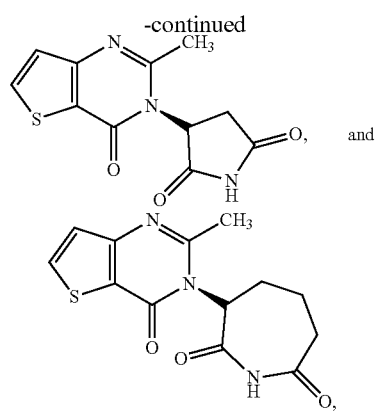

and pharmaceutically acceptable salts thereof.

In some embodiments, the compound of Formula (I) is in the form of a pharmaceutically acceptable salt, for example, a trifluoroacetic acid salt. In one embodiment, the compound of Formula (I) is

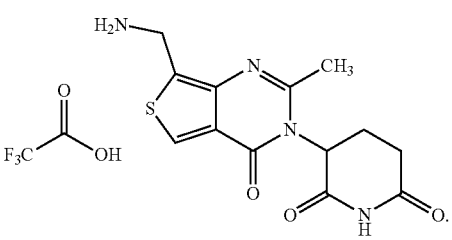 [SMILES: O=C(O)C(F)(F)F ; Cc1nc2c(CN)scc2c(=O)n1C1CCC(=O)NC1=O]

Compounds of Formula (II)

Some embodiments provide a compound of Formula (II):

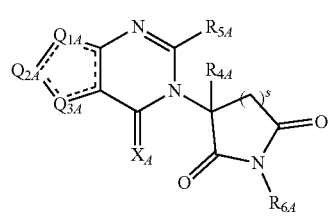

(II)

or a pharmaceutically acceptable salt or solvate thereof, as described herein.

In some embodiments of the compound of Formula (II), $R_{1A}$, $R_{2A}$, and $R_{3A}$ are independently hydrogen, deuterium, hydroxyl, halogen (such as fluoro, chloro, bromo, or iodo), cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy (such as methoxy, ethoxy, n-propoxy, iso-propoxy, n-butoxy, sec-butoxy, t-butoxy, pentoxy (straight chain or branched) and hexoxy (straight chain or branched)), a substituted or unsubstituted $C_1$-$C_6$ alkyl (such as methyl, ethyl, n-propyl, iso-propyl, n-butyl, sec-butyl, t-butyl, pentyl (straight chain or branched) and hexyl (straight chain or branched)), a substituted or unsubstituted $C_2$-$C_6$ alkenyl (such as 1-propene, 2-propene, or 2-butene), a substituted or unsubstituted $C_2$-$C_6$ alkynyl (such as ethynyl or propargyl), a substituted or unsubstituted $C_1$-$C_6$ haloalkyl (such as —CH$_2$F, —CHF$_2$, —CF$_3$, —CH$_2$CF$_3$, and —CCl$_3$), a substituted or unsubstituted C$_3$-C$_8$ cycloalkyl (such as cyclopropyl, cyclobutyl, cyclopentyl, cyclohexyl, cycloheptyl, and cyclooctyl), a substituted or unsubstituted C$_6$-C$_{10}$ aryl (such as phenyl and naphthyl), a substituted or unsubstituted 3-10 membered heterocyclyl (such as aziridine, oxirane, azetidine, oxetane, morpholine, piperidine, piperazine, pyrrolidine, azepane, pyrrolidone, pyrrolidione, 4-piperidone, pyrazoline, pyrazolidine, tetrahydropyran, 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane), a substituted or unsubstituted 5-10 membered heteroaryl (such as furan, furazan, thiophene, benzothiophene, pyrrole, oxazole, benzoxazole, thiazole, benzothiazole, imidazole, benzimidazole, indole, indazole, pyrazole, benzopyrazole, isoxazole, benzoisoxazole, isothiazole, triazole, benzotriazole, pyridine, pyridazine, pyrimidine, pyrazine, purine, quinoline, isoquinoline, quinazoline, and quinoxaline),

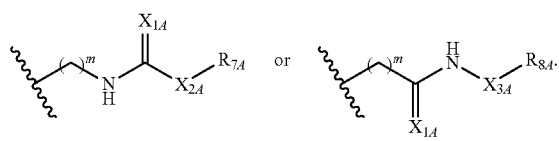

In some embodiments, when R$_{1A}$, R$_{2A}$, and/or R$_{3A}$ is an substituted 4-6 membered heterocyclyl that contains one or more nitrogen atoms, at least one nitrogen atom may be substituted with hydrogen or a substituted or unsubstituted C$_1$-C$_6$ alkyl; for example, the substituted 4-6 membered heterocyclyl may be

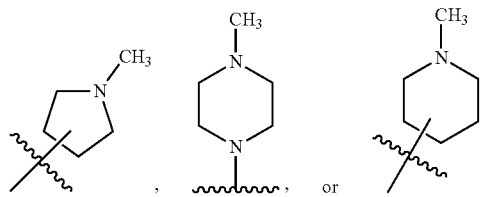

When R$_{1A}$, R$_{2A}$, and/or R$_{3A}$ is an substituted C$_3$-C$_8$ cycloalkyl, C$_3$-C$_8$ cycloalkyl may be substituted with C$_1$-C$_6$ haloalkyl; for example, the substituted C$_3$-C$_8$ cycloalkyl may be

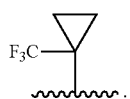

In some embodiments, at least one of R$_{1A}$, R$_{2A}$, and R$_{3A}$ is

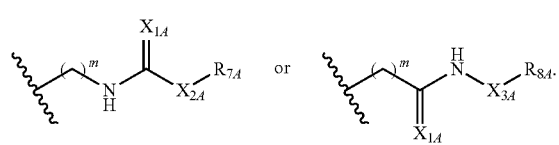

In some further embodiments, one of R$_{1A}$, R$_{2A}$, and R$_{3A}$ is

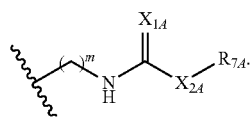

In some other embodiments, one of R$_{1A}$, R$_{2A}$, and R$_{3A}$ is

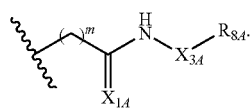

In some embodiments, the compounds of Formula (II) may be further represented by Formula (IIa):

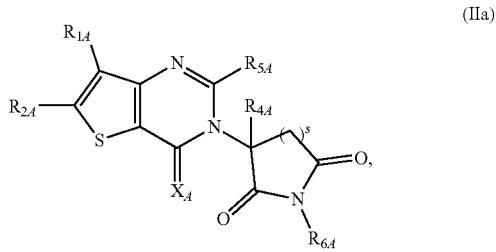

(IIa)

or Formula (IIb):

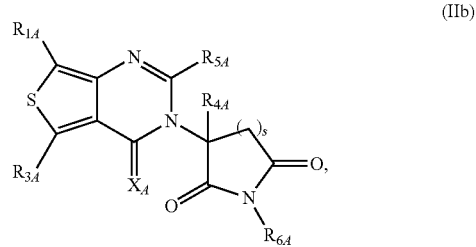

(IIb)

or Formula (IIc):

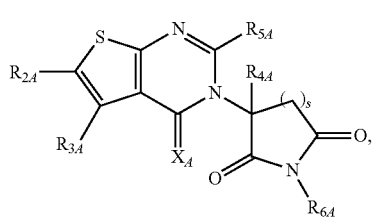

(IIc)

or a pharmaceutically acceptable salt thereof.

In some embodiments, the compound of Formula (II) may also represented by Formula (IIa):

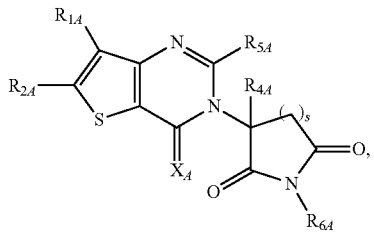

or a pharmaceutically acceptable salt thereof.

In some embodiments, the compound of Formula (II) may also be represented by Formula (IIb):

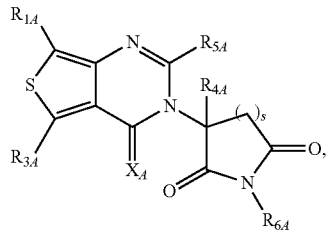

or a pharmaceutically acceptable salt thereof.

In some embodiments, the compound of Formula (II) may also be represented by Formula (IIc):

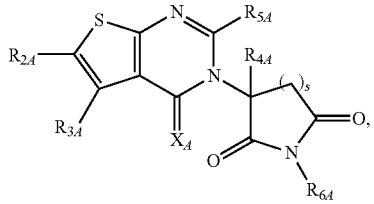

or a pharmaceutically acceptable salt thereof.

In some embodiments of the compound of Formula (II), (IIa), (IIb), or (IIc), s is 1. In some embodiments, s is 2. In some embodiments, s is 3.

In some embodiments of the compound of Formula (II), (IIa), (IIb), or (IIc), $R_{4A}$ is hydrogen. In some embodiments, $R_{4A}$ is deuterium. In some embodiments, $R_{4A}$ is halogen. In some embodiments, $R_{4A}$ is fluoro. In some embodiments, $R_{4A}$ is a substituted or unsubstituted $C_1$-$C_6$ alkyl. In some embodiments, $R_{4A}$ is an unsubstituted $C_1$-$C_6$ alkyl.

In some embodiments of the compound of Formula (II), (IIa), (IIb), or (IIc), $R_{5A}$ is hydrogen. In some embodiments, $R_{5A}$ is deuterium. In some embodiments, $R_{5A}$ is halogen. In some embodiments, $R_{5A}$ is fluoro. In some embodiments, $R_{5A}$ is a substituted or unsubstituted $C_1$-$C_6$ alkyl. In some embodiments, $R_{5A}$ is an unsubstituted $C_1$-$C_6$ alkyl.

In some embodiments of the compound of Formula (II), (IIa), (IIb), or (IIc), $R_{6A}$ is hydrogen. In some embodiments, $R_{6A}$ is deuterium. In some embodiments, $R_{6A}$ is a substituted or unsubstituted $C_1$-$C_6$ alkyl. In some embodiments, $R_{6A}$ is an unsubstituted $C_1$-$C_6$ alkyl.

In some embodiments of the compound of Formula (II), (IIa), (IIb), or (IIc), $X_A$ is O. In some embodiments, $X_A$ is NH. In some embodiments, $X_A$ is S.

In some embodiments of the compound of Formula (II), (IIa), (IIb), or (IIc), one of $R_{1A}$, $R_{2A}$, and $R_{3A}$ is

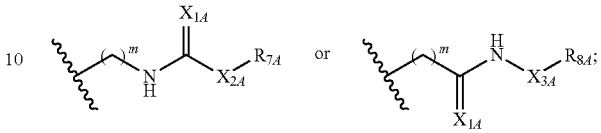

and the other of $R_{1A}$, $R_{2A}$, and $R_{3A}$ are independently hydrogen, deuterium, hydroxyl, halogen, cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl (such as cyclopropyl, optionally substituted with $C_1$-$C_3$ haloalkyl, e.g., —$CF_3$), a substituted or unsubstituted phenyl, a substituted or unsubstituted naphthyl, a substituted or unsubstituted 4-6 membered heterocyclyl (such as pyrrolidinyl, piperazinyl, piperidinyl or morpholinyl, each optionally substituted with $C_1$-$C_3$ alkyl, e.g., methyl), or a substituted or unsubstituted 5 or 6 membered heteroaryl. In some further embodiments, the other of $R_{1A}$, $R_{2A}$, and $R_{3A}$ are independently hydrogen, deuterium, halogen, cyano, nitro, an unsubstituted amino, an unsubstituted $C_1$-$C_3$ alkoxy, an unsubstituted $C_1$-$C_3$ haloalkyl, or an unsubstituted $C_1$-$C_6$ alkyl. In some further embodiments of the compound of Formula (II), (IIa), (IIb), or (IIc), one of $R_{1A}$, $R_{2A}$, and $R_{3A}$ is

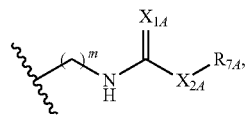

and the other of $R_{1A}$, $R_{2A}$, and $R_{3A}$ are independently hydrogen, deuterium, halogen, —$NH_2$, an unsubstituted $C_1$-$C_3$ haloalkyl, or an unsubstituted $C_1$-$C_6$ alkyl. In some further embodiments, one of $R_{1A}$, $R_{2A}$, and $R_{3A}$ is

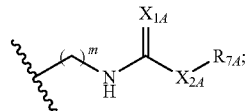

and the other of $R_{1A}$, $R_{2A}$, and $R_{3A}$ are hydrogen. In some embodiments, $R_{1A}$ is

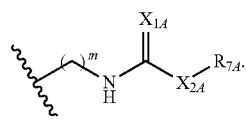

In some embodiments, $R_{2A}$ is

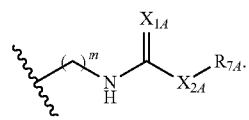

In some embodiments, $R_{3A}$ is

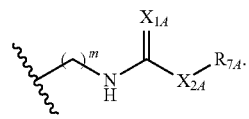

In some such embodiments, each $X_{1A}$ is independently O or NH. In some such embodiments, each $X_{2A}$ is independently $-NR_{9A}-$, $-(CH_2)_h-(NR_{9A})-(CH_2)_i-$, $-(CH_2)_h-(NR_{9A})-(CH_2)_i-(NR_{9A})-$, $-(CH_2)_{1-5}-$, $-(CF_2)_{1-5}-$, $-(CD_2)_{1-5}-$, $-O-$, or $-S-$. In some further embodiments, $X_{2A}$ is $-NR_{9A}-$. In some further embodiments, $X_{2A}$ is $-(CH_2)_{1-5}-$. In some other embodiments, $X_{2A}$ is $-C(=O)-$. In some such embodiments, each $X_{3A}$ is independently $-(CH_2)_t-(NR_{9A})-(CH_2)_j-$, $-(CH_2)_t-(NR_{9A})-(CH_2)_j-(NR_{9A})-$, or $-(CH_2)_{1-5}-$. In some such embodiments, each m is independently 0, 1, 2, or 3. In one embodiment, m is 0. In another embodiment, m is 1. In another embodiment, m is 2. In some such embodiments, each h, i, and j is independently 0, 1, 2, or 3. In some such embodiments, each t is independently 1, 2, or 3. In some further embodiments, m is 1, $X_{1A}$ is O, and $X_{2A}$ is $-C(=O)-$. In some further embodiments, m is 1, $X_{1A}$ is O, and $X_{2A}$ is $-NR_{9A}-$.

In some embodiments, the compound of Formula (II) is represented by Formula (IIa), where one of $R_{1A}$ and $R_{2A}$ is

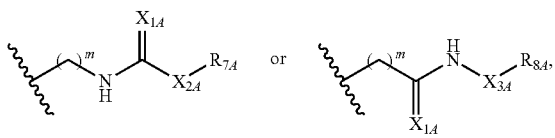

and the other of $R_{1A}$ and $R_{2A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl (such as cyclopropyl, optionally substituted with $C_1$-$C_3$ haloalkyl, e.g., $-CF_3$), a substituted or unsubstituted phenyl, a substituted or unsubstituted 4-6 membered heterocyclyl (such as pyrrolidinyl, piperazinyl, piperidinyl or morpholinyl, each optionally substituted with $C_1$-$C_3$ alkyl, e.g., methyl), or a substituted or unsubstituted 5 or 6 membered heteroaryl. In some embodiments, one of $R_{1A}$ and $R_{2A}$ is

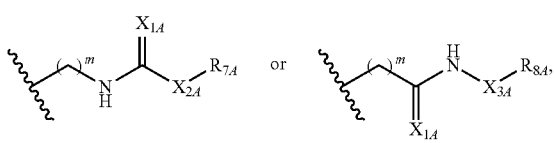

and the other of $R_{1A}$ and $R_{2A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted phenyl, or a substituted or unsubstituted 4-6 membered heterocyclyl. In some further embodiments, one of $R_{1A}$ and $R_{2A}$ is

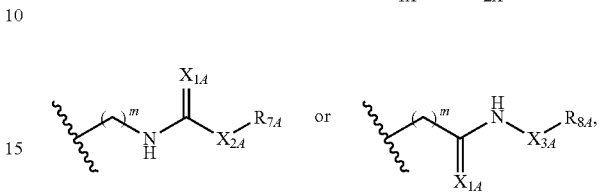

and the other of $R_{1A}$ and $R_{2A}$ is hydrogen. In one embodiment, $R_{1A}$ is

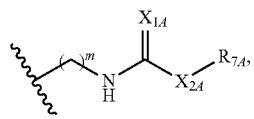

and $R_{2A}$ is hydrogen. In another embodiment, $R_{2A}$ is

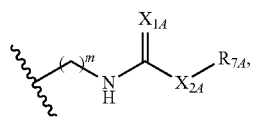

and $R_{1A}$ is hydrogen. In some further embodiments, m is 1, $X_{1A}$ is O, and $X_{2A}$ is $-C(=O)-$. In some further embodiments, m is 1, $X_{1A}$ is O, and $X_{2A}$ is $-NR_{9A}-$.

In some embodiments, the compound of Formula (II) is represented by Formula (IIb), where one of $R_{1A}$ and $R_{3A}$ is

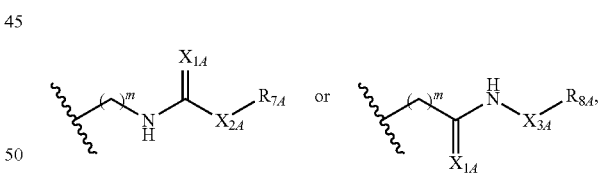

and the other of $R_{1A}$ and $R_{3A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl (such as cyclopropyl, optionally substituted with $C_1$-$C_3$ haloalkyl, e.g., $-CF_3$), a substituted or unsubstituted phenyl, a substituted or unsubstituted 4-6 membered heterocyclyl (such as pyrrolidinyl, piperazinyl, piperidinyl or morpholinyl, each optionally substituted with $C_1$-$C_3$ alkyl, e.g., methyl), or a substituted or unsubstituted 5 or 6 membered heteroaryl. In some embodiments, one of $R_{1A}$ and $R_{3A}$ is

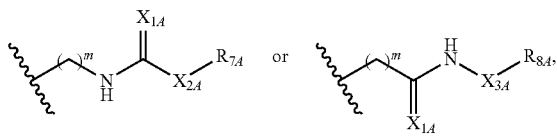 

and the other of $R_{1A}$ and $R_{3A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted phenyl, or a substituted or unsubstituted 4-6 membered heterocyclyl. In some further embodiments, one of $R_{1A}$ and $R_{3A}$ is and the other of $R_{1A}$ and $R_{2A}$ are independently hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted phenyl, or a substituted or unsubstituted 4-6 membered heterocyclyl. In some further embodiments, one of $R_{2A}$ and $R_{3A}$ is

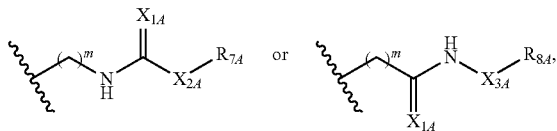 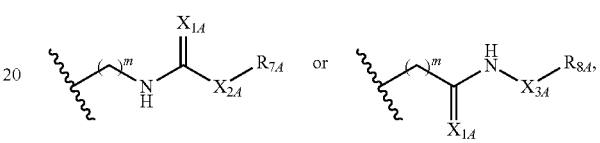

and the other of $R_{1A}$ and $R_{3A}$ is hydrogen. In one embodiment, $R_{1A}$ is and the other of $R_{2A}$ and $R_{3A}$ is hydrogen. In one embodiment, $R_{2A}$ is

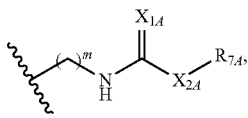 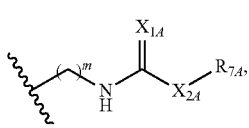

and $R_{3A}$ is hydrogen. In another embodiment, $R_{3A}$ is and $R_{3A}$ is hydrogen. In another embodiment, $R_{3A}$ is

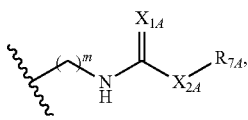 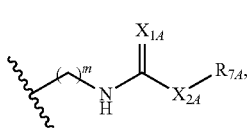

and $R_{1A}$ is hydrogen. In some further embodiments, m is 1, $X_{1A}$ is O, and $X_{2A}$ is —C(=O)—. In some further embodiments, m is 1, $X_{1A}$ is O, and $X_{2A}$ is —NR$_{9A}$—.

In some embodiments, the compound of Formula (II) is represented by Formula (IIc), where one of $R_{2A}$ and $R_{3A}$ is

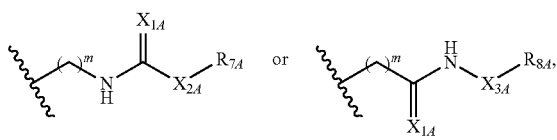

and the other of $R_{2A}$ and $R_{3A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl (such as cyclopropyl, optionally substituted with $C_1$-$C_3$ haloalkyl, e.g., —CF$_3$), a substituted or unsubstituted phenyl, a substituted or unsubstituted 4-6 membered heterocyclyl (such as pyrrolidinyl, piperazinyl, piperidinyl or morpholinyl, each optionally substituted with $C_1$-$C_3$ alkyl, e.g., methyl), or a substituted or unsubstituted 5 or 6 membered heteroaryl. In some embodiments, one of $R_{1A}$ and $R_{2A}$ is and $R_{2A}$ is hydrogen. In some further embodiments, m is 1, $X_{1A}$ is O, and $X_{2A}$ is —C(=O)—. In some further embodiments, m is 1, $X_{1A}$ is O, and $X_{2A}$ is —NR$_{9A}$—.

In some embodiments of the compound of Formula (II), (IIa), (IIb), or (IIc), $X_{2A}$ is —C(=O)—. In some embodiments, $X_{2A}$ is —O—. In some embodiments, $X_{2A}$ is —S—. In some embodiments, $X_{2A}$ is —(CH$_2$)$_{1-5}$—. In some embodiments, $X_{2A}$ is —(CF$_2$)$_{1-5}$—. In some embodiments, $X_{2A}$ is —(CD$_2$)$_{1-5}$—. In some embodiments, $X_{2A}$ is —O— or —(CH$_2$)$_{1-5}$—. In some embodiments, $X_{2A}$ is —NR$_{9A}$—. In some embodiments, $X_{2A}$ is —(CH$_2$)$_h$—(NR$_{9A}$)—(CH$_2$)$_i$—. In some embodiments, $X_{2A}$ is —(CH$_2$)$_h$—(NR$_{9A}$)—(CH$_2$)$_i$—(NR$_{9A}$)—. In some embodiments, $X_{2A}$ is —(CH$_2$)$_h$—(NR$_{9A}$)—(CH$_2$)$_i$— or —(CH$_2$)$_h$—(NR$_{9A}$)—(CH$_2$)$_i$—(NR$_{9A}$)—. In some embodiments, each of h and i is independently 0, 1, 2, or 3. In some embodiments, each of h and i is independently 0, 1, 2 or 3. In some embodiments, h is 0. In some embodiments, h is 1. In some embodiments, h is 2. In some embodiments, h is 3. In some embodiments, i is 0. In some embodiments, i is 1. In some embodiments, i is 2. In some embodiments, i is 3. In some embodiments, h and i are the same. In some embodiments, h and i are different.

In some embodiments of the compound of Formula (II), (IIa), (IIb), or (IIc), $X_{3A}$ is —(CH$_2$)$_{1-5}$—. In some embodiments, $X_{3A}$ is —(CH$_2$)— or —(CH$_2$)$_2$—. In some embodiments, $X_{3A}$ is —(CH$_2$)$_t$—(NR$_{9A}$)—(CH$_2$)$_j$—. In some other embodiments, $X_{3A}$ is —(CH$_2$)$_t$—(NR$_{9A}$)—(CH$_2$)$_j$—(NR$_{9A}$)—. In some embodiments, t is 1. In some embodiments, t is 2. In some embodiments, t is 3. In some embodiments, j is 0. In some embodiments, j is 1. In some embodiments, j is 2. In some embodiments, j is 3. In some embodiments, t and j are the same. In some embodiments, t and j are different.

In some embodiments of the compound of Formula (II), (IIa), (IIb), or (IIc), each of $R_{7A}$ and $R_{8A}$ is independently selected from the group consisting of a substituted or unsubstituted C$_3$-C$_6$ cycloalkyl, a substituted or unsubstituted phenyl, a substituted or unsubstituted naphthyl, a substituted or unsubstituted 5 or 6 membered heteroaryl, a substituted or unsubstituted 3-7 membered heterocyclyl, and a substituted or unsubstituted C$_1$-C$_6$ alkyl. In some embodiments, when $R_{7A}$ and/or $R_{8A}$ is an substituted 5 or 6 membered heterocyclyl that contains one or more nitrogen atoms, at least one nitrogen atom may be substituted with hydrogen or a substituted or unsubstituted C$_1$-C$_6$ alkyl; for example, the substituted 5 or 6 membered heterocyclyl may be

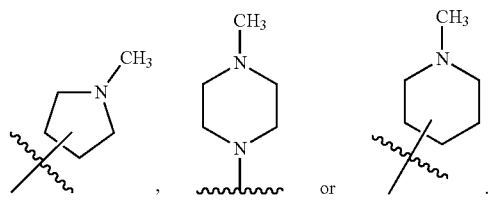

When $R_{7A}$ and/or $R_{8A}$ is an substituted C$_3$-C$_6$ cycloalkyl, C$_3$-C$_6$ cycloalkyl may be substituted with C$_1$-C$_6$ haloalkyl; for example, the substituted C$_3$-C$_6$ cycloalkyl may be

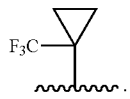

When $R_{7A}$ and $R_{8A}$ are independently a substituted C$_3$-C$_6$ cycloalkyl, a substituted phenyl, a substituted naphthyl, a substituted 5 or 6 membered heteroaryl, a substituted 3-7 membered heterocyclyl, and a substituted C$_1$-C$_6$ alkyl, each group may be substituted with one, two or three substituents selected from the group consisting of halogen, amino, —N(C$_1$-C$_3$ alkyl)$_2$, —NH(C$_1$-C$_3$ alkyl), an unsubstituted C$_1$-C$_6$ alkyl, an C$_1$-C$_6$ haloalkyl (for example —CF$_3$), an unsubstituted C$_1$-C$_6$ alkoxy, a C$_1$-C$_6$ alkyl substituted with C$_1$-C$_6$ alkoxy, amino, —N(C$_1$-C$_3$ alkyl)$_2$, or —NH(C$_1$-C$_3$ alkyl), substituted or unsubstituted C$_3$-C$_6$ cycloalkyl, substituted or unsubstituted heterocyclyl, an (unsubstituted C$_1$-C$_6$ alkyl)amine, an substituted or unsubstituted C$_3$-C$_6$ cycloalkyl(unsubstituted C$_1$-C$_6$ alkyl), and an substituted or unsubstituted heterocyclyl(unsubstituted C$_1$-C$_6$ alkyl).

In some further embodiments, each of $R_{7A}$ and $R_{8A}$ is independently selected from the group consisting of a substituted or unsubstituted phenyl, a substituted or unsubstituted thienyl, a substituted or unsubstituted pyridinyl, a substituted or unsubstituted pyrimidinyl, a substituted or unsubstituted pyrazinyl, a substituted or unsubstituted pyridazinyl, a substituted or unsubstituted pyrrolidinyl, a substituted or unsubstituted morpholino, a substituted or unsubstituted piperidinyl, a substituted or unsubstituted piperazinyl, or a substituted or unsubstituted azepanyl. In some embodiments, each of $R_{7A}$ and $R_{8A}$ is an unsubstituted phenyl. In some other embodiments, each of $R_{7A}$ and $R_{8A}$ is independently a phenyl substituted with one, two or three substituents selected from the group consisting of halogen, amino, —N(C$_1$-C$_3$ alkyl)$_2$, —NH(C$_1$-C$_3$ alkyl), an unsubstituted C$_1$-C$_6$ alkyl, an C$_1$-C$_6$ haloalkyl (for example —CF$_3$), an unsubstituted C$_1$-C$_6$ alkoxy, a C$_1$-C$_6$ alkyl substituted with C$_1$-C$_6$ alkoxy, amino, —N(C$_1$-C$_3$ alkyl)$_2$, or —NH(C$_1$-C$_3$ alkyl), substituted or unsubstituted C$_3$-C$_6$ cycloalkyl, substituted or unsubstituted heterocyclyl, an (unsubstituted C$_1$-C$_6$ alkyl)amine, an substituted or unsubstituted C$_3$-C$_6$ cycloalkyl(unsubstituted C$_1$-C$_6$ alkyl), and an substituted or unsubstituted heterocyclyl(unsubstituted C$_1$-C$_6$ alkyl). In some such embodiments, the unsubstituted C$_1$-C$_6$ haloalkyl may be, for example, —CH$_2$F, —CHF$_2$, —CF$_3$, —CH$_2$CF$_3$, —CClH$_2$, —CCl$_2$H, or —CCl$_3$. In some such embodiments, C$_1$-C$_6$ alkyl substituted with amino may be, for example, —CH$_2$NH$_2$, —CH$_2$CH$_2$NH$_2$, or

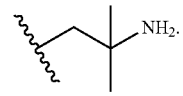

In some such embodiments, C$_1$-C$_6$ alkyl substituted with —NH(C$_1$-C$_3$ alkyl) may be, for example,

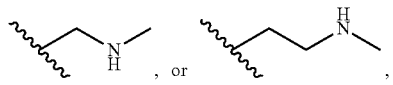

In some such embodiments, C$_1$-C$_6$ alkyl substituted with —N(C$_1$-C$_3$ alkyl)$_2$ may be, for example,

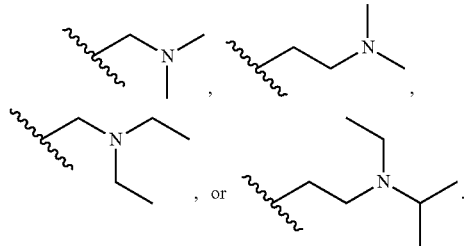

In some such embodiments, the unsubstituted heterocyclyl (unsubstituted C$_1$-C$_6$ alkyl) may be, for example,

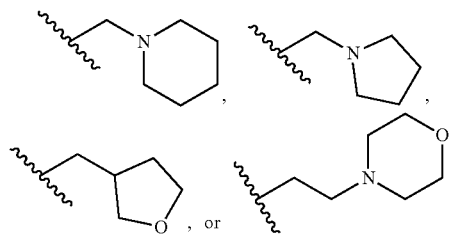

In some further embodiments, each of $R_{7A}$ and $R_{8A}$ is independently a phenyl substituted with one, two or three substituents selected from the group consisting halogen, an unsubstituted $C_1$-$C_6$ alkyl, unsubstituted $C_1$-$C_3$ alkoxy, —NH($C_1$-$C_3$ alkyl), —N($C_1$-$C_3$ alkyl)$_2$, unsubstituted or substituted $C_3$-$C_6$ cycloalkyl, unsubstituted or substituted 3 to 6 membered heterocyclyl (for example, aziridine, azetidine, pyrrolidine, morpholine, piperidine, or piperazine), (unsubstituted $C_1$-$C_6$ alkyl)amine, and heterocyclyl(unsubstituted $C_1$-$C_6$ alkyl).

In some further embodiments, each of $R_{7A}$ and $R_{8A}$ is independently a phenyl mono-substituted with halogen, methyl, ethyl, propyl, isopropyl, t-butyl, —N($C_1$-$C_3$ alkyl)$_2$, —NH($C_1$-$C_3$ alkyl), an unsubstituted —(CH$_2$)$_{1-5}$—N(CH$_3$)$_2$, for example, —(CH$_2$)—N(CH$_3$)$_2$, —(CH$_2$)$_2$—N(CH$_3$)$_2$ or —(CH$_2$)$_3$—N(CH$_3$)$_2$.

In some further embodiments, each of $R_{7A}$ and $R_{8A}$ is independently a phenyl di-substituted with a halogen and an unsubstituted $C_1$-$C_6$ alkyl (such as methyl, ethyl, propyl, isopropyl, or t-butyl), di-substituted with an unsubstituted $C_1$-$C_6$ alkyl and a —N($C_1$-$C_3$ alkyl)$_2$ (for example, —N(CH$_3$)$_2$), di-substituted with an halogen and a —N($C_1$-$C_3$ alkyl)$_2$ (for example, —N(CH$_3$)$_2$), or di-substituted with an unsubstituted $C_1$-$C_6$ alkyl and 3 to 6 membered heterocyclyl group (for example, aziridine, azetidine, pyrrolidine, morpholine, piperidine, piperidine, or piperazine, each of which may be optionally substituted with $C_1$-$C_3$ alkyl at the nitrogen atom).

In some further embodiments, each of $R_{7A}$ and $R_{8A}$ is independently a phenyl substituted with heterocyclyl(unsubstituted $C_1$-$C_6$ alkyl). In some embodiments, the heterocyclyl of the heterocyclyl(unsubstituted $C_1$-$C_6$ alkyl) is an N-linked heterocyclyl where the alkyl group is substituted at the nitrogen atom of the heterocyclyl. In some embodiments, the N-linked heterocyclyl is morpholino, piperidinyl, or piperazinyl. In some embodiments, the unsubstituted $C_1$-$C_6$ alkyl of the heterocyclyl(unsubstituted $C_1$-$C_6$ alkyl) is a methylene, an ethylene, or an n-propylene.

In some further embodiments, each of $R_{7A}$ and $R_{8A}$ is independently a phenyl substituted with unsubstituted or substituted $C_3$-$C_6$ cycloalkyl. In some such embodiments, each of $R_{7A}$ and $R_{8A}$ is independently a phenyl substituted with a cyclopropyl, cyclobutyl, cyclopentyl, or cyclohexyl. In some further embodiments, the cyclopropyl, cyclobutyl, cyclopentyl, or cyclohexyl is further optionally substituted with one or more substituents, such as halogen, unsubstituted $C_1$-$C_6$ alkyl, $C_1$-$C_6$ haloalkyl (for example —CF), or unsubstituted $C_1$-$C_3$ alkoxy. In one embodiment, each of $R_{7A}$ and $R_{8A}$ is independently a phenyl substituted with

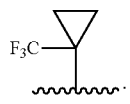

In some embodiments, each of $R_{7A}$ and $R_{8A}$ is independently an unsubstituted thienyl or a thienyl substituted with one or more substituents selected from the group consisting of halogen, unsubstituted $C_1$-$C_6$ alkyl, $C_1$-$C_6$ haloalkyl (for example —CF$_3$), unsubstituted $C_1$-$C_3$ alkoxy, —N($C_1$-$C_3$ alkyl)$_2$, and —NH($C_1$-$C_3$ alkyl).

In any embodiments of the compound of Formula (II), (IIa), (IIb), or (IIc), $R_{9A}$ is hydrogen or an unsubstituted $C_1$-$C_6$ alkyl. In some embodiments, $R_{9A}$ is hydrogen. In some embodiments, $R_{9A}$ is an unsubstituted $C_1$-$C_6$ alkyl, for example, methyl, ethyl, isopropyl, or t-butyl.

In some embodiments, the compound of Formula (II) is selected from the group comprising the following:

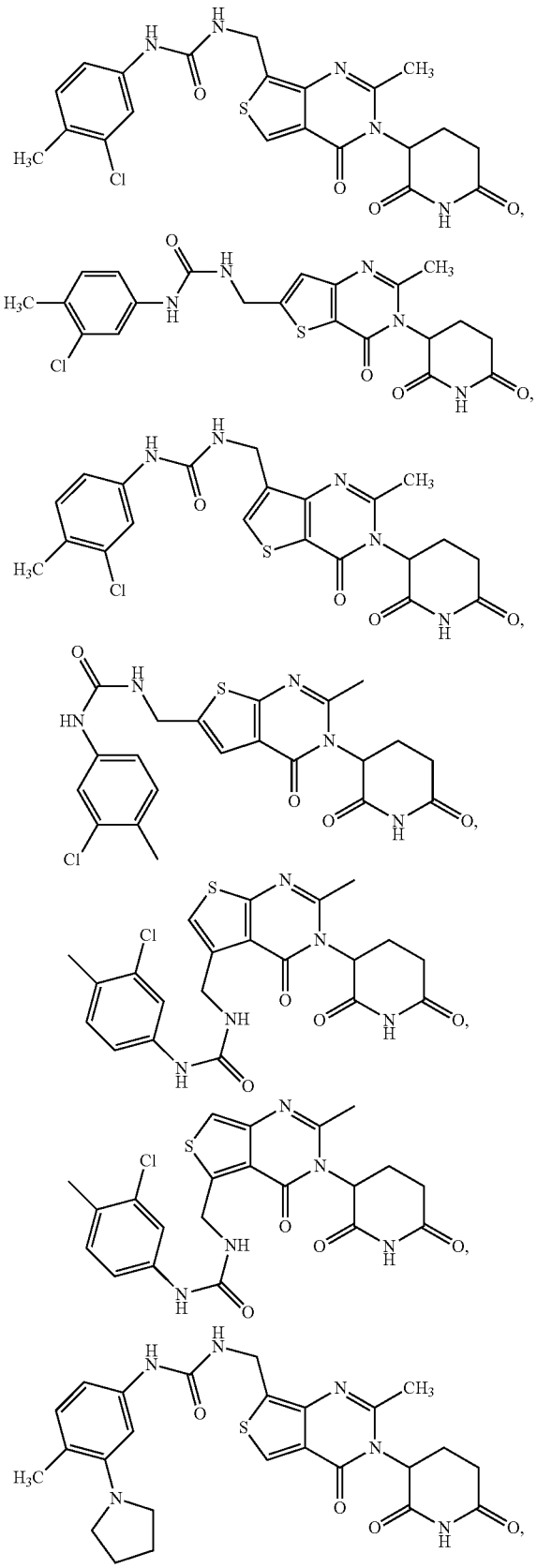

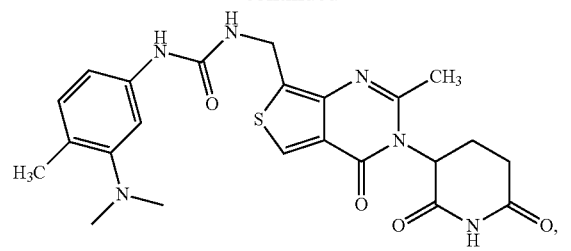
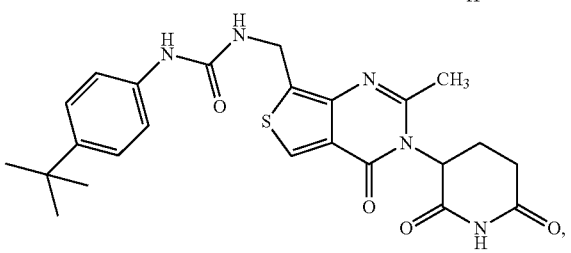
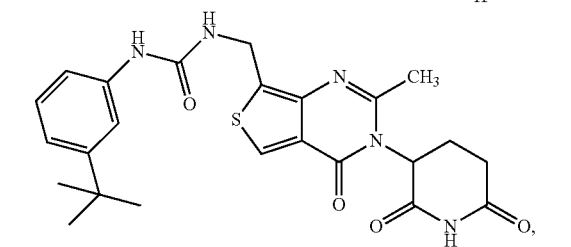
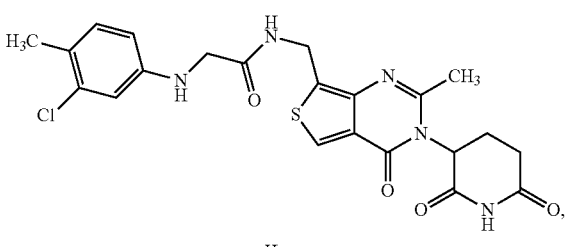
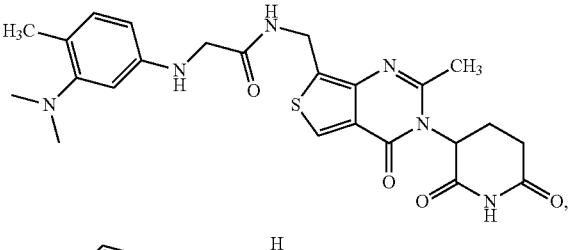
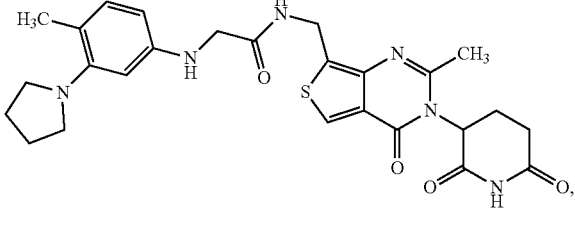
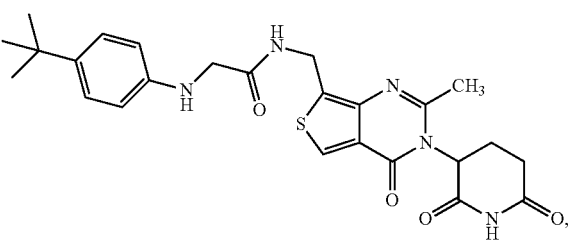
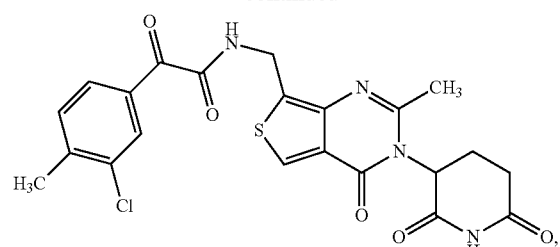
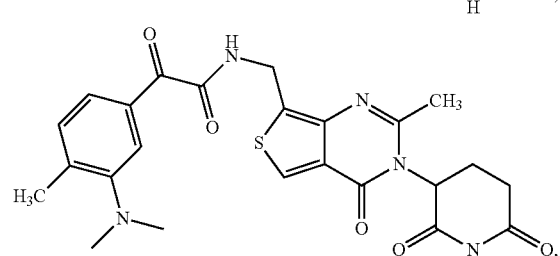
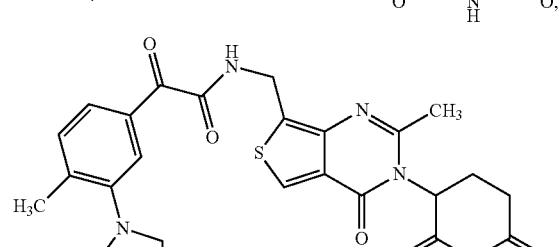
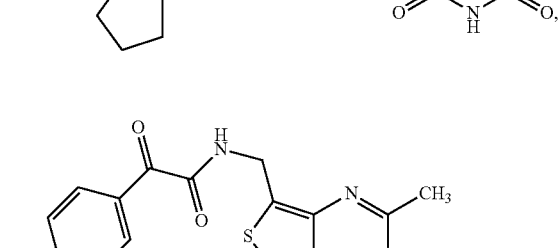
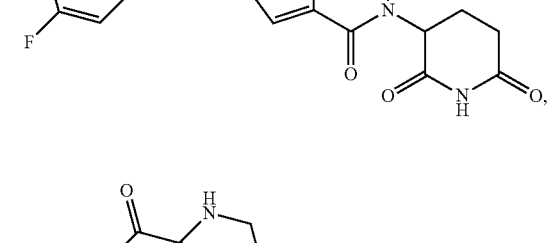
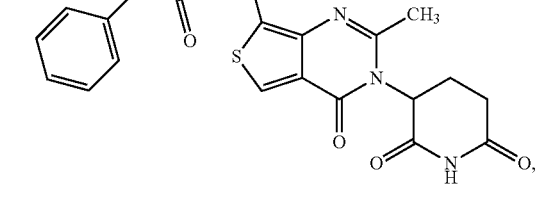
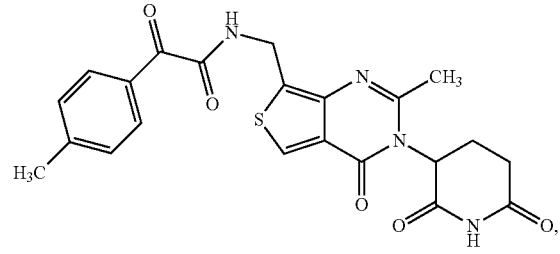

-continued

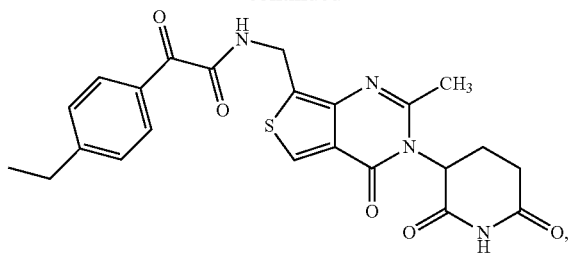

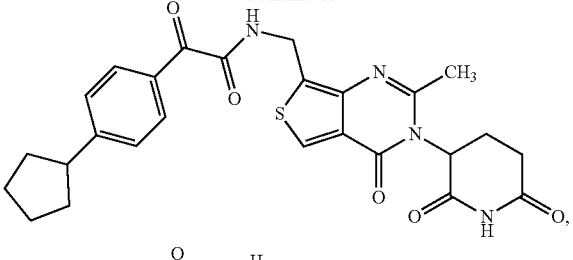

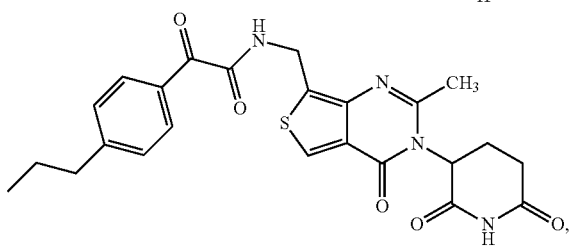

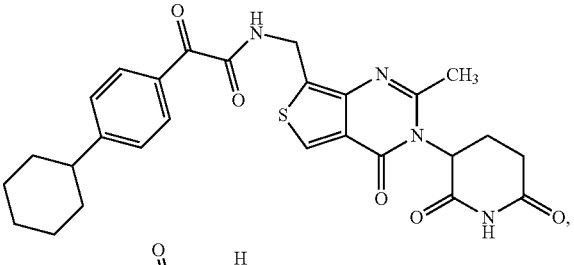

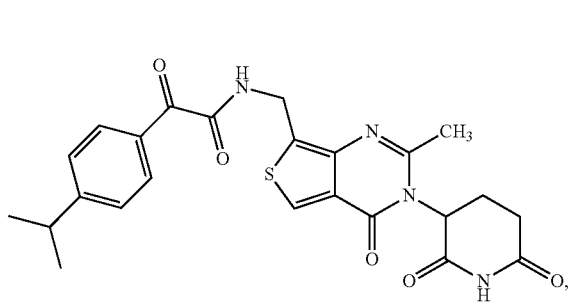

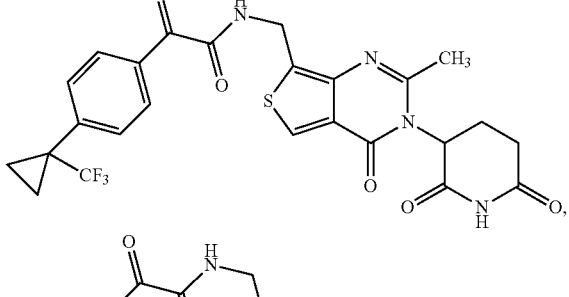

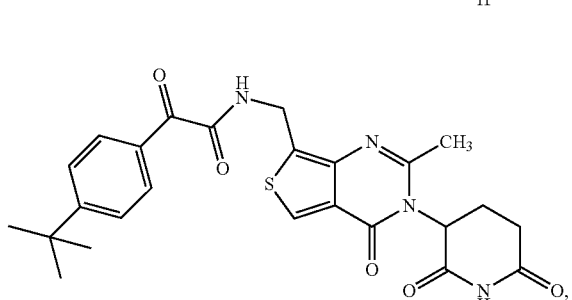

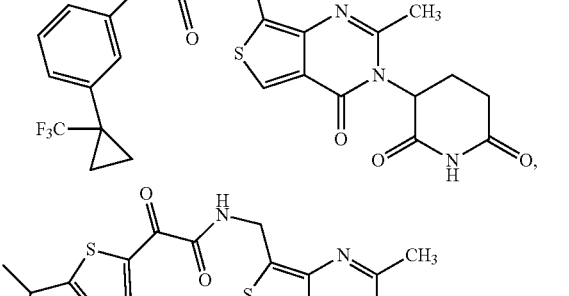

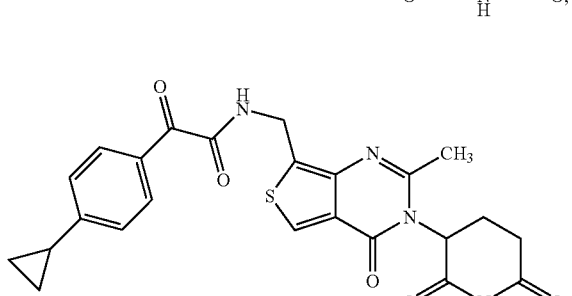

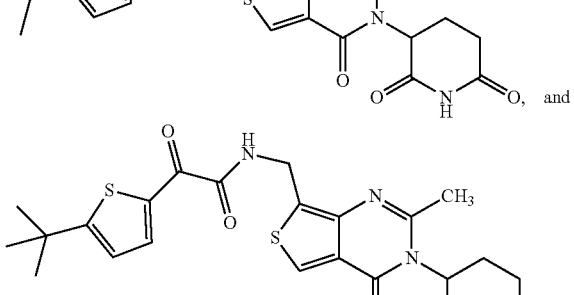, and

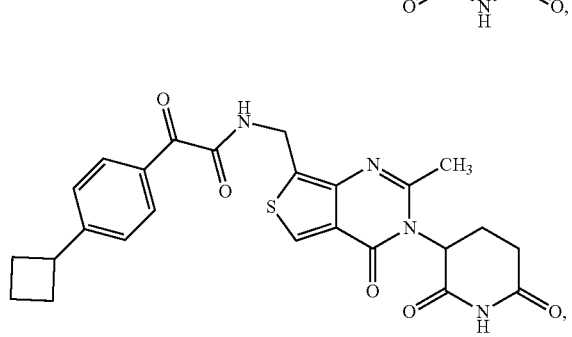

and pharmaceutically acceptable salts thereof.

In some embodiments, the compound of Formula (I) or the compound of Formula (II) is formed as a pharmaceutically acceptable salt. In some embodiments, the compound of Formula (I), the compound of Formula (II), or a pharmaceutically acceptable salt of any of the foregoing, is racemic. In some embodiments, the compound of Formula (I), the compound of Formula (II), or a pharmaceutically acceptable salt of any of the foregoing, has an S-configuration. In some embodiments, the compound of Formula (I), the compound of Formula (II), or a pharmaceutically acceptable salt of any of the foregoing, has an R-configuration. In some embodiments, the compound of Formula (I), the compound of Formula (II), or a pharmaceutically acceptable salt of any of the foregoing, is enriched in one enantiomer over another enantiomer, for example, enriched by about 10%, 20%, 30%, 40%, 50%, 60%, 70%, 80%, 90%, 95%, or 99%, or any value in between. In some embodiments, the compound of Formula (I), the compound of Formula (II), or a pharmaceutically acceptable salt of any of the foregoing, is enriched in one diastereomer over another diastereomer for example, enriched by about 10%, 20%, 30%, 40%, 50%, 60%, 70%, 80%, 90%, 95%, or 99%, or any value in between. In some embodiments, the compound of Formula (I), or the compound of Formula (II), is a pharmaceutically acceptable salt. In some embodiments, the compound of Formula (I), or the compound of Formula (II), is a pharmaceutically acceptable solvate.

Some embodiments provide a pharmaceutical composition comprising a compound of Formula (I), a compound of Formula (II), or a pharmaceutically acceptable salt of any of the foregoing; and a pharmaceutically acceptable excipient.

Methods of Treatment

Some embodiments provide a method of treating, ameliorating, or preventing a disease, disorder, or condition associated with GSPT1, comprising administering a therapeutically effective amount of a compound of Formula (I), a compound of Formula (II), or a pharmaceutically acceptable salt of any of the foregoing, or a pharmaceutical composition comprising a compound described herein (for example, a therapeutically effective amount of a compound of Formula (I), a compound of Formula (II), or a pharmaceutically acceptable salt of any of the foregoing). Other embodiments provide the use of a compound of Formula (I), a compound of Formula (II), or a pharmaceutically acceptable salt of any of the foregoing, or a pharmaceutical composition comprising a compound described herein (for example, a therapeutically effective amount of a compound of Formula (I), a compound of Formula (II), or a pharmaceutically acceptable salt of any of the foregoing) for treating, ameliorating, or preventing a disease, disorder, or condition associated with GSPT1. Still other embodiments provide a compound of Formula (I), a compound of Formula (II), or a pharmaceutically acceptable salt of any of the foregoing, for use in preparing a medicament for treating, ameliorating, or preventing a disease, disorder, or condition associated with GSPT1. In some further embodiments, the disease, disorder, or condition associated with GSPT1 malfunction. In some embodiments, the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer. In some embodiments, the disease, disorder, or condition is cancer. In some further embodiments, the disease, disorder, or condition is a cancer selected from the group consisting of a breast cancer, lung cancer, leukemia, lymphoma, hepatocellular carcinoma, gastric cancer, prostate cancer and astrogliosis, and combinations thereof. In some additional embodiments, the disease, disorder, or condition is a cancer selected from the group consisting of leukemia (such as acute myelogenous leukemia), lymphoma, and hepatocellular carcinoma. In some such embodiments, the subject possesses wild-type GSPT1 or aberrant GSPT1. In some other embodiments, the subject overexpresses GSPT1.

Some embodiments provide a method of inhibiting GSPT1 activity, or a method of decreasing cellular levels of GSPT1, comprising contacting a cell with a compound of a therapeutically effective amount of a compound of Formula (I), a compound of Formula (II), or a pharmaceutically acceptable salt of any of the foregoing. Other embodiments provide the use of a compound of Formula (I), a compound of Formula (II), or a pharmaceutically acceptable salt of any of the foregoing, for inhibiting GSPT1 activity in a cell, or decreasing cellular levels of GSPT1. Still other embodiments provide a compound of Formula (I), a compound of Formula (II), or a pharmaceutically acceptable salt of any of the foregoing, for use in preparing a medicament for inhibiting GSPT1 activity in a cell, or decreasing cellular levels of GSPT1. In some embodiments, the cell is a breast cancer cell, a lung cancer cell, a leukemia cell, a lymphoma cell, a hepatocellular carcinoma cell, a gastric cancer cell, or a prostate cancer cell. In some further embodiments, the cell is a leukemia cell, a lymphoma cell, or a hepatocellular carcinoma cell. In some such embodiments, the cell possesses wild-type GSPT1 or aberrant GSPT1, or overexpresses GSPT1.

Some embodiments provide a method of treating, ameliorating, or preventing a disease, disorder, or condition associated with one or more proteins selected from the group consisting of cytokine, aiolos, phosphodiesterase (PDE) (such as PDE6), ikaros, helios, and CK1α and combinations thereof, comprising administering a therapeutically effective amount of a compound of Formula (I), a compound of Formula (II), or a pharmaceutically acceptable salt of any of the foregoing, or a pharmaceutical composition comprising a compound described herein (for example, a therapeutically effective amount of a compound of Formula (I), a compound of Formula (II), or a pharmaceutically acceptable salt of any of the foregoing). In some embodiments, the protein is a cytokine. In some embodiments, the cytokine is selected from the group consisting of IL-1β, IL-6, TNFα, and IL-2, and combinations thereof. In some embodiments, the cytokine is a pro-inflammatory cytokine. In other embodiments, the protein is aiolos, ikaros, or helios. In still other embodiments, the protein is CK1α. In some embodiments, the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer. In some embodiments, the disease, disorder, or condition is cancer. In some embodiments, the disease, disorder, or condition is a cancer selected from the group consisting of a leukemia, a lymphoma, and a hepatocellular carcinoma.

Some embodiments provide a method of modulating (such as inhibiting or stimulating) protein activity, comprising contacting a cell with a compound of Formula (I), a compound of Formula (II), or a pharmaceutically acceptable salt of any of the foregoing; wherein the protein is selected from the group consisting of a cytokine, aiolos, phosphodiesterase (PDE) (such as PDE6), ikaros, helios, and CK1α. Other embodiments provide the use of a compound of Formula (I), a compound of Formula (II), or a pharmaceutically acceptable salt of any of the foregoing, for modulating (such as inhibiting or stimulating) protein activity; wherein the protein is selected from the group comprising cytokine, aiolos, phosphodiesterase (PDE) (such as PDE6), ikaros, helios, and CK1α. Still other embodiments provide a compound of Formula (I), a compound of Formula (II), or a pharmaceutically acceptable salt of any of the foregoing, for use in preparing a medicament for modulating (such as inhibiting or stimulating) protein activity; wherein the protein is selected from the group comprising cytokine, aiolos, phosphodiesterase (PDE) (such as PDE6), ikaros, helios, and CK1α. In some embodiments, the method or use inhibits a cytokine activity, wherein the cytokine is one or more pro-inflammatory cytokines selected from a group consisting of IL-1β, IL-6, and TNFα. In some embodiments, the method or use stimulates cytokine activity, wherein the cytokine is one or more anti-inflammatory cytokines, such as IL-2. In some embodiments, the method or use inhibits aiolos activity. In some embodiments, the method or use inhibits phosphodiesterase (PDE) (such as PDE6) activity. In some embodiments, the method or use inhibits ikaros activity. In some embodiments, the method or use inhibits helios activity. In some embodiments, the method or use inhibits CK1α activity.

Some embodiments provide a method of decreasing the risk of skin cancer in a subject in need thereof, comprising administering a therapeutically effective amount of a compound of Formula (I), a compound of Formula (II), or a pharmaceutically acceptable salt of any of the foregoing, or a pharmaceutical composition comprising a compound described herein (for example, a therapeutically effective amount a compound of Formula (I), a compound of Formula (II), or a pharmaceutically acceptable salt of any of the foregoing). Other embodiments provide the use of a compound of Formula (I), a compound of Formula (II), or a pharmaceutically acceptable salt of any of the foregoing, or a pharmaceutical composition comprising a compound described herein (for example, a therapeutically effective amount of a compound of Formula (I), a compound of Formula (II), or a pharmaceutically acceptable salt of any of the foregoing) for decreasing the risk of skin cancer. Still other embodiments provide a compound of Formula (I), a compound of Formula (II), or a pharmaceutically acceptable salt of any of the foregoing, for use in preparing a medicament for decreasing the risk of skin cancer. In some embodiments, administering to the subject comprising contacting the skin of the subject. In other embodiments, administering to the subject comprising oral administration to the subject.

Some embodiments provide a method for treating, ameliorating, or preventing a skin disorder, disease, or condition in a subject, comprising administering to the subject a therapeutically effective amount of a compound of Formula (I), a compound of Formula (II), or a pharmaceutically acceptable salt of any of the foregoing, or a pharmaceutical composition comprising a compound described herein (for example, a therapeutically effective amount a compound of Formula (I), a compound of Formula (II), or a pharmaceutically acceptable salt of any of the foregoing). Other embodiments provide the use of a compound of Formula (I), a compound of Formula (II), or a pharmaceutically acceptable salt of any of the foregoing, or a pharmaceutical composition comprising a compound described herein (for example, a therapeutically effective amount of a compound of Formula (I), a compound of Formula (II), or a pharmaceutically acceptable salt of any of the foregoing) for treating, ameliorating, or preventing a skin disorder, disease, or condition. Still other embodiments provide a compound of Formula (I), a compound of Formula (II), or a pharmaceutically acceptable salt of any of the foregoing, for use in preparing a medicament for treating, ameliorating, or preventing a skin disorder, disease, or condition. In some embodiments the skin disorder, disease, or condition is sunburn or skin hypopigmentation. In some embodiments, administering to the subject comprising contacting the skin of the subject. In other embodiments, administering to the subject comprising oral administration to the subject.

Some embodiments provide a method of increasing skin pigmentation in a subject in need thereof, comprising administering a therapeutically effective amount of a compound of Formula (I), a compound of Formula (II), or a pharmaceutically acceptable salt of any of the foregoing, or a pharmaceutical composition comprising a compound described herein (for example, a therapeutically effective amount a compound of Formula (I), a compound of Formula (II), or a pharmaceutically acceptable salt of any of the foregoing). Other embodiments provide the use of a compound of Formula (I), a compound of Formula (II), or a pharmaceutically acceptable salt of any of the foregoing, or a pharmaceutical composition comprising a compound described herein (for example, a therapeutically effective amount of a compound of Formula (I), a compound of Formula (II), or a pharmaceutically acceptable salt of any of the foregoing) for increasing skin pigmentation. Still other embodiments provide a compound of Formula (I), a compound of Formula (II), or a pharmaceutically acceptable salt of any of the foregoing, for use in preparing a medicament for increasing skin pigmentation. In some embodiments, administering to the subject comprising contacting the skin of the subject. In other embodiments, administering to the subject comprising oral administration to the subject.

Some embodiments provide a method of increasing eumelanin levels in a subject in need thereof, comprising administering a therapeutically effective amount of a compound of Formula (I), a compound of Formula (II), or a pharmaceutically acceptable salt of any of the foregoing, or a pharmaceutical composition comprising a compound described herein (for example, a therapeutically effective amount a compound of Formula (I), a compound of Formula (II), or a pharmaceutically acceptable salt of any of the foregoing). Other embodiments provide the use of a compound of Formula (I), a compound of Formula (II), or a pharmaceutically acceptable salt of any of the foregoing, or a pharmaceutical composition comprising a compound described herein (for example, a therapeutically effective amount of a compound of Formula (I), a compound of Formula (II), or a pharmaceutically acceptable salt of any of the foregoing) for increasing eumelanin levels. Still other embodiments provide a compound of Formula (I), a compound of Formula (II), or a pharmaceutically acceptable salt of any of the foregoing, for use in preparing a medicament for increasing eumelanin levels. In some embodiments, administering to the subject comprising contacting the skin of the subject. In other embodiments, administering to the subject comprising oral administration to the subject.

Some embodiments provide a method of increasing p53 activity, comprising contacting a cell with a compound of Formula (I), a compound of Formula (II), or a pharmaceutically acceptable salt of any of the foregoing. In some embodiments, the cell is a leukemia cell, a lymphoma cell, or a hepatocellular carcinoma cell. Other embodiments provide the use of a compound of Formula (I), a compound of Formula (II), or a pharmaceutically acceptable salt of any of the foregoing, for increasing p53 activity in a cell. Still other embodiments provide a compound of Formula (I), a compound of Formula (II), or a pharmaceutically acceptable salt of any of the foregoing, for use in preparing a medicament for increasing p53 activity in a cell. In some embodiments, the cell is a leukemia cell, a lymphoma cell, or a hepatocellular carcinoma cell.

Some embodiments provide a method of decreasing MDM2 activity, comprising contacting a cell with a compound of Formula (I), a compound of Formula (II), or a pharmaceutically acceptable salt of any of the foregoing. Other embodiments provide the use of a compound of Formula (I), a compound of Formula (II), or a pharmaceutically acceptable salt of any of the foregoing, for decreasing MDM2 activity in a cell. Still other embodiments provide a compound of Formula (I), a compound of Formula (II), or a pharmaceutically acceptable salt of any of the foregoing, for use in preparing a medicament for decreasing MDM2 activity in a cell. In some embodiments, the cell is a leukemia cell, a lymphoma cell, or a hepatocellular carcinoma cell.

One or more of the compounds of preferred embodiments can be provided in the form of pharmaceutically acceptable salts, solvates, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

The pharmaceutical compositions of preferred embodiments can further comprise one or more additional therapeutically active agents other than a compound of the preferred embodiments. Such agents can include, but are not limited to, anti-inflammatory agents, anti-cancer agents, immunostimulatory agents, and immunosuppressive agents.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description Additional Therapeutic Agents Some embodiments provide pharmaceutical compositions comprising a compound of Formula (I), a compound of Formula (II), or a pharmaceutically acceptable salt of any of the foregoing and a pharmaceutically acceptable excipient. Some embodiments provide pharmaceutical compositions comprising a compound of Formula (I), a compound of Formula (II), or a pharmaceutically acceptable salt of any of the foregoing, a pharmaceutically acceptable excipient, and a second therapeutic agent. Some embodiments provide methods of treating, ameliorating, or preventing a disease, disorder, or condition associated with GSPT1 (for example, inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer (such as a leukemia, a lymphoma, or a hepatocellular carcinoma)), comprising administering a therapeutically effective amount of a compound of Formula (I), a compound of Formula (II), or a pharmaceutically acceptable salt of any of the foregoing with a second therapeutic agent. Other embodiments provide methods of treating, ameliorating, or preventing a disease, disorder, or condition associated with a protein selected from the group consisting of a cytokine, aiolos, ikaros, helios, and CK1α (such as inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer), comprising administering a therapeutically effective amount of a compound of Formula (I), a compound of Formula (II), or a pharmaceutically acceptable salt of any of the foregoing with a second therapeutic agent. Still other embodiments provide (a) methods of decreasing the risk of skin cancer; (b) methods for treating, ameliorating, or preventing a skin disorder, disease, or condition (such as sunburn or skin hypopigmentation); (c) methods of increasing skin pigmentation; and (d) methods of increasing eumelanin levels; each comprising administering a therapeutically effective amount of a compound of Formula (I), a compound of Formula (II), or a pharmaceutically acceptable salt of any of the foregoing with a second therapeutic agent.

In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone. In some embodiments, the second therapeutic agent is selected from mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; and oxaliplatin. In some embodiments, the second therapeutic agent is selected from vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; and teniposide. In some embodiments, the second therapeutic agent is selected from actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; and procarbazine. In some embodiments, the second therapeutic agent is selected from cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; and floxuridine. In some embodiments, the second therapeutic agent is selected from azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; and triethylenemelamine. In some embodiments, the second therapeutic agent is selected from nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; and eribulin. In some embodiments, the second therapeutic agent is selected from azathioprine; Mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; and ocrelizumab. In some embodiments, the second therapeutic agent is selected from pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; and rilonacept.

Dosing Regimes

In some embodiments, about 1 mg to about 5 grams, or any amount in between, of a compound of Formula (I), a compound of Formula (II), or a pharmaceutically acceptable salt of any of the foregoing is administered each day, each week, or each cycle of treatment.

In some embodiments, a compound of Formula (I), a compound of Formula (II), or a pharmaceutically acceptable salt of any of the foregoing is administered once per day, twice per day, three times per day, four times per day, or more than four times per day. In some embodiments, a compound of Formula (I), a compound of Formula (II), or a pharmaceutically acceptable salt of any of the foregoing is administered once per day, twice per day, three times per day, four times per day, or more than four times per month. In some embodiments, a compound of Formula (I), a compound of Formula (II), or a pharmaceutically acceptable salt of any of the foregoing is administered once per day, twice per day, three times per day, four times per day, or more than four times per cycle of treatment.

In some embodiments, each cycle of treatment lasts from 1 day to 14 days, or any value in between. In some embodiments, each cycle of treatment has from at least one day up to fourteen days, or any value in between, between administrations of a compound of Formula (I), a compound of Formula (II), or a pharmaceutically acceptable salt of any of the foregoing. In some embodiments, each cycle of treatment includes one or more additional therapeutic agents, as described herein. In some embodiments, a compound of Formula (I), a compound of Formula (II), or a pharmaceutically acceptable salt of any of the foregoing is provided intravenously over about 10 minutes to over about 4 hours, or any value in between.

Pharmaceutical Compositions

Some embodiments described herein relate to a pharmaceutical composition, that can include an effective amount of one or more compounds described herein (for example, a compound of Formula (I) (including Formulas (Ia), (Ib) and (Ic)), a compound of Formula (II) (including Formulas (IIa), (IIb) and (IIc)), or a pharmaceutically acceptable salt of any of the foregoing) and at least one pharmaceutically acceptable excipient.

The term "pharmaceutical composition" refers to a mixture of one or more compounds and/or salts disclosed herein with other chemical components, such as one or more excipients. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

As used herein, an "excipient" refers to essentially inert substances that are added to a pharmaceutical composition to provide, without limitation, bulk, consistency, stability, binding ability, lubrication, disintegrating ability etc., to the composition. For example, stabilizers such as anti-oxidants and metal-chelating agents are excipients. Excipients also include ingredients in a pharmaceutical composition that lack appreciable pharmacological activity but may be pharmaceutically necessary or desirable. For example, to increase the bulk of a potent drug whose mass is too small for manufacture and/or administration. It may also be a liquid for the dissolution of a drug to be administered by injection, ingestion or inhalation. For example, a buffered aqueous solution such as, without limitation, phosphate buffered saline that mimics the pH and isotonicity of human blood.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), a compound of Formula (II), or a pharmaceutically acceptable salt thereof, or a pharmaceutical composition thereof can be administered orally or be applied topically on the skin.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

EXAMPLES

Additional embodiments are disclosed in further detail in the following examples, which are not in any way intended to limit the scope of the claims.

Characterization of the compounds disclosed herein is performed with Bruker AV-500 and Bruker DRX-500 NMR spectrometers and a Perkin Elmer PE-SCIEX API-150 mass spectrometer.

Example 1

General Synthesis $Q_1$, $Q_2$, $Q_3$, and $R_5$, as shown in Schemes 1-4, can represent $Q_1$, $Q_2$, $Q_3$, and $R_5$ of compounds of Formula (I), or $Q_{1A}$, $Q_{2A}$, $Q_{3A}$, and $R_{5A}$ of compounds of Formula (II), and are abbreviated in the structures below solely for clarity. The definitions of $Q_1$, $Q_2$, $Q_3$, $R_1$, $R_2$, $R_3$, $R_4$, $R_5$, $R_6$, X, h, i, j, t, m, n, s, $Q_{1A}$, $Q_{2A}$, $Q_{3A}$, $R_{1A}$, $R_{2A}$, $R_{3A}$, $R_{4A}$, $R_{5A}$, $R_{6A}$, $R_{7A}$, $R_{8A}$, $R_{9A}$, $X_A$, $X_{1A}$, $X_{2A}$, and $X_{3A}$, are those as described herein.

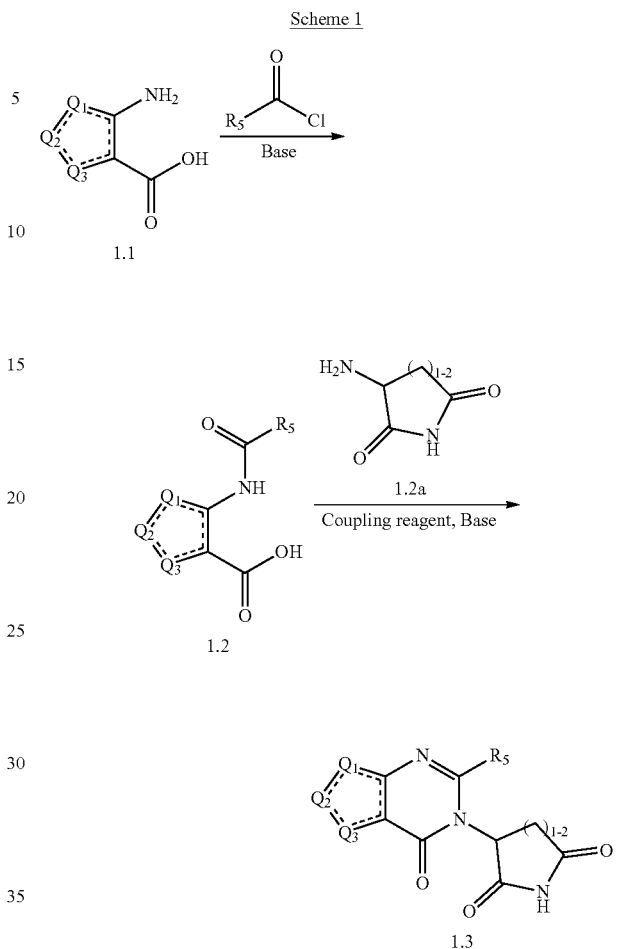

To a solution of compound 1.1 in an organic solvent (for example, ACN), at a cooled temperature, such as 0° C., is added a base (for example, imidazole). After sufficient time for reaction, such as 20 min, an acid chloride (for example, acetyl chloride) is added. After sufficient time for reaction, such as 20 min, the reaction is diluted with an organic solvent, (for example, ethyl acetate), and extracted with $H_2O$. The organic phase is washed with brine, dried using a drying agent, such as $MgSO_4$, filtered and concentrated under vacuum to provide crude compound 1.2, which is used in the next step without further purification.

To a solution of compound 1.2 in an organic solvent (for example, ACN), at a cooled temperature, such as 0° C., is added a base (for example, imidazole) and a coupling reagent (for example, triphenyl phosphite). After sufficient time for reaction, such as 20 min, a cyclic amine 1.2a (for example, 3-aminopyrrolidine-2,5-dione or 3-aminopiperidine-2,6-dione) is added. After sufficient time for reaction, such as 20 min, the reaction is diluted with an organic solvent, (for example, ethyl acetate), and extracted with $H_2O$. The organic phase is washed with brine, dried using a drying agent, such as $MgSO_4$, filtered and concentrated under vacuum to provide crude compound 1.3, which is purified by, for example, column chromatography over silica gel, HPLC, and/or crystallization.

Scheme 2

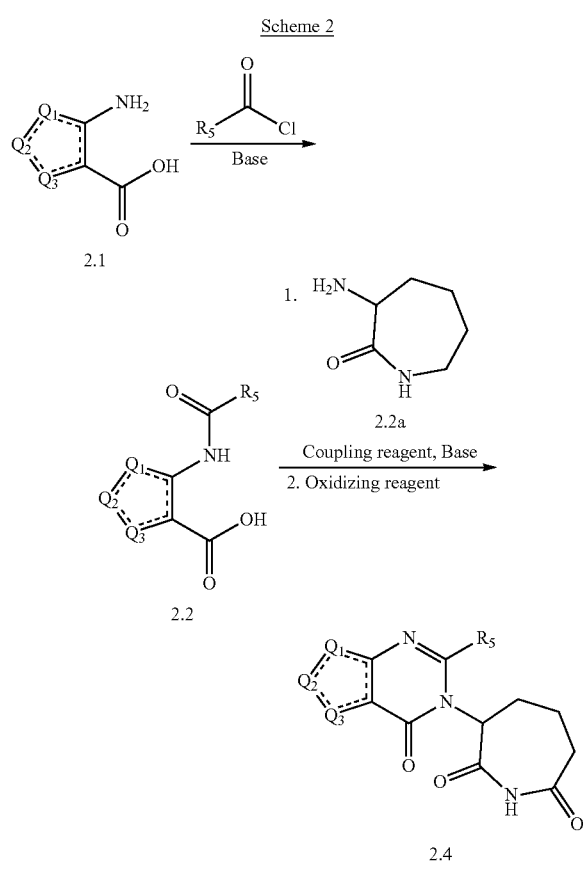

Scheme 3

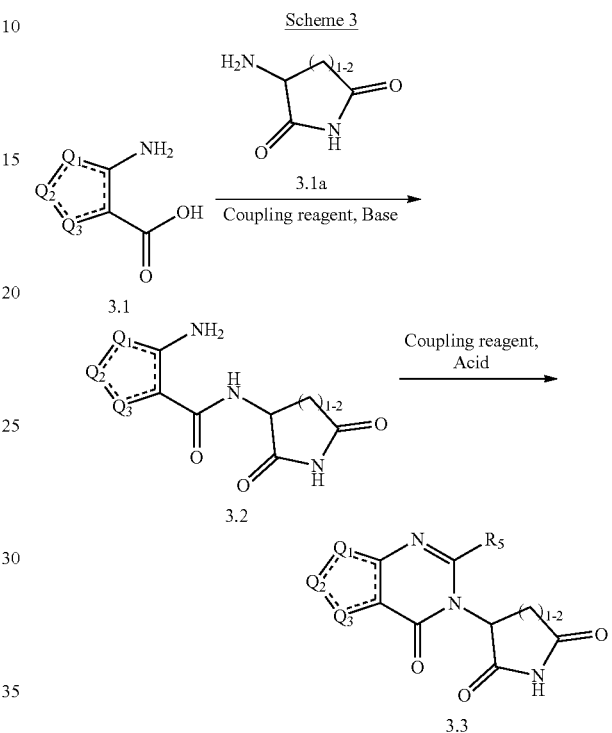

To a solution of compound 2.1 in an organic solvent (for example, ACN), at a cooled temperature, such as 0° C., is added a base (for example, imidazole). After sufficient time for reaction, such as 20 min, an acid chloride (for example, formyl chloride) is added. After sufficient time for reaction, such as 20 min, the reaction is diluted with an organic solvent, (for example, ethyl acetate), and extracted with $H_2O$. The organic phase is washed with brine, dried using a drying agent, such as $MgSO_4$, filtered and concentrated under vacuum to provide crude compound 2.2, which is used in the next step without further purification.

To a solution of compound 2.2 in an organic solvent (for example, ACN), at a cooled temperature, such as 0° C., is added a base (for example, imidazole) and a coupling reagent (for example, triphenyl phosphite). After sufficient time for reaction, such as 20 min, a cyclic amine 2.2a (for example, 3-aminoazepan-2-one) is added. After sufficient time for reaction, such as 20 min, the reaction is diluted with an organic solvent, (for example, ethyl acetate), and extracted with $H_2O$. The organic phase is washed with brine, dried using a drying agent, such as $MgSO_4$, filtered and concentrated under vacuum to provide crude compound 2.3 (structure not shown), which is optionally purified prior to use the next step.

To a solution of compound 2.3 in an organic solvent (for example, fluorobenze) and wet DMSO, at a cooled temperature, such as 0° C., is added an oxidizing agent (for example, Dess-Martin periodinane). After sufficient time for reaction, such as 20 min, the reaction is diluted with an organic solvent, (for example, ethyl acetate), and extracted with $H_2O$. The organic phase is washed with brine, dried using a drying agent, such as $MgSO_4$, filtered and concentrated under vacuum to provide crude compound 2.4, which is purified by, for example, column chromatography over silica gel, HPLC, and/or crystallization.

To a solution of compound 3.1 in an organic solvent (for example, ACN), at a cooled temperature, such as 0° C., is added a base (for example, $NaHCO_3$) and a coupling reagent (for example, CDI). After sufficient time for reaction, such as 20 min, a cyclic amine 3.1a (for example, 3-aminopyrrolidine-2,5-dione or 3-aminopiperidine-2,6-dione) is added. After sufficient time for reaction, such as 20 min, the reaction is diluted with an organic solvent, (for example, ethyl acetate), and extracted with $H_2O$. The organic phase is washed with brine, dried using a drying agent, such as $MgSO_4$, filtered and concentrated under vacuum to provide crude compound 3.2, which is optionally purified prior to use in the next step.

To a solution of compound 3.2 in an organic solvent (for example, ACN), at a cooled temperature, such as 0° C., is added a coupling reagent (for example, trimethyl orthoformate) and an acid (for example, para-toluene sulfonic acid). After sufficient time for reaction, such as 20 min, the reaction is diluted with an organic solvent, (for example, ethyl acetate), and extracted with $H_2O$. The organic phase is washed with brine, dried using a drying agent, such as $MgSO_4$, filtered and concentrated under vacuum to provide crude compound 3.3, which is purified by, for example, column chromatography over silica gel, HPLC, and/or crystallization.

Scheme 4

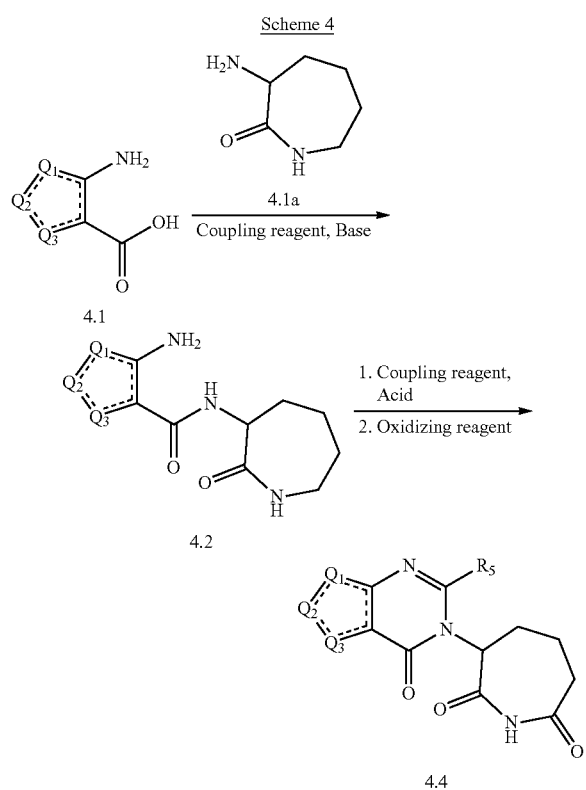

To a solution of compound 4.1 in an organic solvent (for example, ACN), at a cooled temperature, such as 0° C., is added a base (for example, NaHCO$_3$) and a coupling reagent (for example, CDI). After sufficient time for reaction, such as 20 min, a cyclic amine 4.1a (for example, 3-aminoazepan-2-one) is added. After sufficient time for reaction, such as 20 min, the reaction is diluted with an organic solvent, (for example, ethyl acetate), and extracted with H$_2$O. The organic phase is washed with brine, dried using a drying agent, such as MgSO$_4$, filtered and concentrated under vacuum to provide crude compound 4.2, which is optionally purified prior to use in the next step.

To a solution of compound 4.2 in an organic solvent (for example, ACN), at a cooled temperature, such as 0° C., is added a coupling reagent (for example, trimethyl orthoformate) and an acid (for example, para-toluene sulfonic acid). After sufficient time for reaction, such as 20 min, the reaction is diluted with an organic solvent, (for example, ethyl acetate), and extracted with H$_2$O. The organic phase is washed with brine, dried using a drying agent, such as MgSO$_4$, filtered and concentrated under vacuum to provide crude compound 4.3 (structure not shown), which is optionally purified prior to use in the next step.

To a solution of compound 4.3 in an organic solvent (for example, fluorobenze) and wet DMSO, at a cooled temperature, such as 0° C., is added an oxidizing agent (for example, Dess-Martin periodinane). After sufficient time for reaction, such as 20 min, the reaction is diluted with an organic solvent, (for example, ethyl acetate), and extracted with H$_2$O. The organic phase is washed with brine, dried using a drying agent, such as MgSO$_4$, filtered and concentrated under vacuum to provide crude compound 4.4, which is purified by, for example, column chromatography over silica gel, HPLC, and/or crystallization.

Example 2

Compound 1: 3-(2-methyl-4-oxothieno[3,2-d]pyrimidin-3(4H)-yl)piperidine-2,6-dione

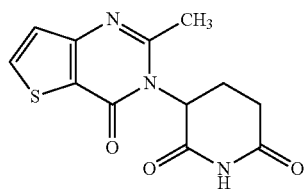 [SMILES: Cc1nc2ccsc2c(=O)n1C1CCC(=O)NC1=O]

To a solution of 3-amino-2-thiophenecarboxylic acid methyl ester (1.00 g, 6.36 mmol) in pyridine (6 mL) at 0° C. was added acetyl chloride (0.524 g, 6.68 mmol) dropwise over 5 min. The mixture was stirred at RT for 1 h then concentrated. H$_2$O was added and the resulting precipitate was filtered and dried to give 3-acetyl amine-2-thiophenecarboxylic acid methyl ester (1.20 g, 94% yield) as a solid. MS (ESI) m/z 200.3 [M+H]$^+$.

To a solution of 3-acetyl amine-2-thiophenecarboxylic acid methyl ester (1.20 g, 6.03 mmol) in MeOH (40 mL) at RT was added NaOH (0.527 g, 6.09 mmol). The mixture was stirred at 50° C. for 16 h then concentrated. 1N HCl was added and the resulting precipitate was filtered and dried to give 3-acetyl amine-2-thiophenecarboxylic acid (0.827 g, 74% yield) as a solid. MS (ESI) m/z 186.0 [M+H]$^+$.

To a solution of 3-acetyl amine-2-thiophenecarboxylic acid (0.300 g, 1.62 mmol) in ACN (4 mL) at RT was added imidazole (0.415 g, 6.10 mmol), triphenyl phosphite (0.603 g, 1.94 mmol) and 3-aminopiperidine-2,6-dione HCl. (0.267 g, 1.62 mmol). The mixture was stirred at 80° C. for 16 h. After concentration, H$_2$O was added, and the resulting solid was washed with EA, filtered, and dried to give Compound 1 (0.025 g, 6% yield) as a solid. MS (ESI) m/z 278.6 [M+H]$^+$. $^1$H NMR (400 MHz, DMSO-d6) δ 11.02 (s, 1 H), 8.175-8.186 (s, 2 H), 7.35 (s, 1 H), 5.312 (m, 2.86-2.81 (m, 1H), 2.65 (s, 3H), 2.63 (m, 1 H), 2.61 (m, 1H), 2.194-2.165 (m, 1H).

Example 3

Compound 2: 3-(2-methyl-4-oxothieno[3,4-d]pyrimidin-3(4H)-yl)piperidine-2,6-dione

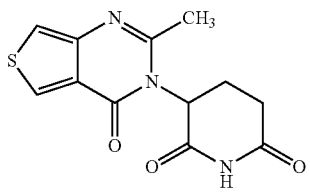 [SMILES: Cc1nc2cscc2c(=O)n1C1CCC(=O)NC1=O]

To a solution of 4-acetamidothiophene-3-carboxylic acid methyl ester (1.84 g, 9.25 mmol) in MeOH (14 mL) and H$_2$O (4 mL) at RT was added KOH (0.958 g, 17.1 mmol). The mixture was stirred at 50° C. for 16 h then concentrated. H$_2$O (10 mL) was added and the mixture was acidified to pH 2 using 1N HCl. The precipitate was filtered and dried to give 4-acetamidothiophene-3-carboxylic acid as a solid (1.32 grams, 78% yield). MS (ESI) m/z 186.0 [M+H]$^+$.

To a solution of 4-acetamidothiophene-3-carboxylic acid (0.350 g, 1.89 mmol) in ACN (4 mL) at RT was added imidazole (0.322 g, 4.73 mmol) followed by triphenyl phosphite (0.603 mg, 1.94 mmol) and 3-aminopiperidine-2,6-dione HCl. (0.311 g, 1.89 mmol). The mixture was heated under microwave at 150° C. for 45 min then cooled to RT. After concentration, H₂O was added and the mixture was extracted with EA. The organic phase was concentrated and the residue was purified using silica gel eluting with MeOH/EA (1:9) to afford Compound 2 as a solid (60 mg, 12% yield). MS (ESI) m/z 278.0 [M+H]⁺. ¹H NMR (400 MHz, DMSO-d6) δ 10.98 (s, 1 H), 8.42 (s, 1 H), 7.72 (s, 1 H), 5.14-5.18 (m, 1H), 2.75-2.79 (m, 1H), 2.52-2.61 (m, 5 H), 2.12-2.15 (m, 1H).

Example 4

Compound 3: 3-(2-methyl-4-oxothieno[2,3-d]pyrimidin-3(4H)-yl)piperidine-2,6-dione

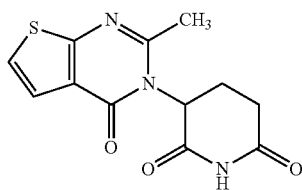 [SMILES: Cc1nc2sccc2c(=O)n1C1CCC(=O)NC1=O]

To a solution of methyl-2-aminothiophene-3-carboxylate (2.00 g, 12.7 mmol) in pyridine (8 mL) at 0° C. was added acetyl chloride (1.39 g, 17.8 mmol) dropwise over 5 min. The mixture was stirred at RT for 16 h then concentrated. H₂O and EA were added. The organic phase was washed with brine, dried over Na₂SO₄, filtered, and concentrated to give methyl-2-acetamido-3-thiophenecarboxylate as a solid (2.7 grams, 100% yield). MS (ESI) m/z 200.0 [M+H]⁺.

Methyl-2-acetamido-3-thiophenecarboxylate (2.53 grams, 12.7 mmol) in a 5% KOH MeOH solution (125 mL) and stirred at 70° C. for 2 h. After concentration, H₂O (15 mL) was added and the solution was acidified to pH 2 using 1N HCl. The resulting precipitate was filtered and dried to give 2-acetamido-3-thiophenecarboxylic acid (1.7 grams, 72% yield). MS (ESI) m/z 158 [M-28]⁺.

To a solution of 2-acetamido-3-thiophenecarboxylic acid (300 mg, 1.62 mmol) in ACN (5 mL) at RT was added imidazole (353 mg, 5.18 mmol), triphenyl phosphite (754 mg, 2.43 mmol) and 3-aminopiperidine-2,6-dione HCl (262 mg, 1.62 mmol). The mixture was heated under microwave at 150° C. for 1 h then cooled to RT. After concentration, H₂O was added and the mixture was extracted with EA. The organic phase was concentrated and the residue was purified using silica gel eluting with EA/hexanes (1:1) to afford Compound 3 (115 mg, 25% yield) as a solid. MS (ESI) m/z 278 [M+H]⁺. ¹H NMR (400 MHz, DMSO-d6) δ 11.02 (s, 1 H), 7.51-7.54 (d, 1H), 7.30-7.32 (d, 1H), 5.25-5.29 (m, 1H), 2.83-2.87 (m, 1H), 2.65 (s, 3H), 2.50-2.55 (m, 2H), 2.46-2.49 (m, 1H).

Example 5

Compound 4: 3-(6-bromo-2-methyl-4-oxothieno[3,2-d]pyrimidin-3(4H)-yl)piperidine-2,6-dione

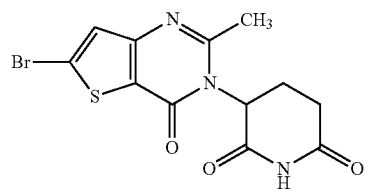 [SMILES: Cc1nc2cc(Br)sc2c(=O)n1C1CCC(=O)NC1=O]

To a solution of 3-amino-5-bromo-2-thiophenecarboxylic acid methyl ester (0.500 g, 2.12 mmol) in pyridine (3 mL) at 0° C. was added acetyl chloride (0.174 g, 2.22 mmol) dropwise over 5 min. The mixture was stirred at RT for 1 h. After concentration, H₂O was added, and the resulting precipitate was filtered and dried to give 3-acetyl amine-5-bromo-2-thiophenecarboxylic acid methyl ester (0.475 g, 81% yield) as a solid. MS (ESI) m/z 278.3 [M+H]⁺.

To a solution of 3-acetamido-5-bromo-2-thiophenecarboxylic acid methyl ester (0.475 g, 1.72 mmol) in MeOH (2 mL) and H₂O (2 mL) at RT was added NaOH (0.069 g, 1.715 mmol). The mixture was stirred at 50° C. for 16 h then concentrated. 1N HCl was added and the resulting precipitate was filtered and dried to give 3-acetamido-5-bromo-2-thiophenecarboxylic acid (0.444 g, 98% yield). MS (ESI) m/z 264.0 [M+H]⁺.

To a solution of 3-acetamido-5-bromo-2-thiophenecarboxylic acid (0.45 g, 0.17 mmol) in ACN (3 mL) at RT was added imidazole (0.029 g, 0.43 mmol), triphenyl phosphite (0.0636, 0.205 mmol) and 3-aminopiperidine-2,6-dione HCl. (0.028 g, 0.17 mmol). The mixture was heated under microwave at 150° C. for 1 h then cooled to RT. After concentration, H₂O was added and the mixture was extracted with EA. A resulting solid, which precipitated from the aqueous phase, was filtered and dried to give Compound 4 (0.011 g, 18% yield). MS (ESI) m/z 357.2 [M+H]⁺.

Example 6

Compound 5: 3-(5-bromo-2-methyl-4-oxothieno[2,3-d]pyrimidin-3(4H)-yl)piperidine-2,6-dione

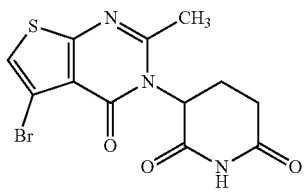 [SMILES: Cc1nc2scc(Br)c2c(=O)n1C1CCC(=O)NC1=O]

A solution of methyl 2-amino-4-bromo-2-thiophenecarboxylate (0.500 g, 2.12 mmol) in acetic anhydride (3 mL) was heated under microwave at 140° C. for 30 min then cooled to RT. H₂O was added and the mixture was extracted with EA. The organic phase was washed with brine, dried over Na₂SO₄, filtered, and concentrated to give methyl 2-acetamido-4-bromo-3-thiophenecarboxylate (0.589 g, 100% yield) as a solid. MS (ESI) m/z 278.3 [M+H]⁺.

To a solution of methyl 2-acetamido-4-bromo-3-thiophenecarboxylate (0.20 g, 0.72 mmol) in MeOH (2 mL) and H₂O (2 mL) at RT was added NaOH (0.086 g, 2.16 mmol). The mixture was stirred at 50° C. for 16 h. After concentration, 1N HCl was added, and the resulting precipitate was filtered and dried under vacuum to give 2-acetamido-4-bromo-3-thiophenecarboxylic acid (0.115 g, 61% yield). MS (ESI) m/z 263.0 [M–H]⁻.

To a solution of 2-acetamido-4-bromo-3-thiophenecarboxylic acid (0.115 g, 0.44 mmol) in ACN (3 mL) at RT was added imidazole (0.074.5 g, 1.04 mmol), triphenyl phosphite (0.338, 1.09 mmol) and 3-aminopiperidine-2,6-dione HCl (0.072 g, 0.44 mmol). The mixture was heated under microwave at 150° C. for 1 h then cooled to RT. After concentration, H₂O was added and the mixture was extracted with EA. A resulting solid, which precipitated from the aqueous phase, was filtered and dried to give Compound 5 (0.025 g, 16% yield). MS (ESI) m/z 357.3 [M+H]⁺. ¹H NMR (400 MHz, DMSO-d6) δ 11.032 (s, 1 H), 7.694 (s, 1 H), 5.276 (m, 1H), 2.875-2.804 (m, 1H), 2.650 (s, 3 H), 2.598-2.566 (m, 2H), 2.185-2.150 (m, 1H).

Example 7

Compound 6: 3-(2,6-dimethyl-4-oxothieno[2,3-d]pyrimidin-3(4H)-yl)piperidine-2,6-dione

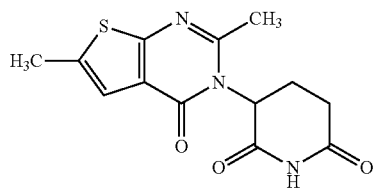 [SMILES: Cc1cc2c(=O)n(C3CCC(=O)NC3=O)c(C)nc2s1]

To a solution of methyl 2-amino-5-methylthiophene-3-carboxylate (2.00 g, 11.6 mmol) in pyridine (14 mL) at 0° C. was added acetyl chloride (0.875 mL). The reaction was stirred at RT for 18 h then concentrated. EA was added and the organic solution was washed with 1 N HCl. The organic phase was concentrated to give methyl 2-acetamido-5-methylthiophene-3-carboxylate (2.15 g, 86% yield). MS (ESI) m/z 214.3 [M+H]⁺.

To a solution of 2-acetamido-5-methylthiophene-3-carboxylate (1.50 g, 7.04 mmol) in MeOH (30 mL) and H₂O (30 mL) was added NaOH (1.15 grams). The mixture was stirred at 55° C. overnight, cooled to RT, and acidified to a pH of 3-4 using HCl (1N). The resulting solid was filtered and concentrated to give 2-acetamido-5-methylthiophene-3-carboxylic acid (0.986 g, 70% yield). MS (ESI) m/z 200.3 [M+H]⁺.

To 2-acetamido-5-methylthiophene-3-carboxylic acid (0.200 g, 1.00 mmol) in ACN (2 mL) was added 3-aminopiperidine-2,6-dione HCl (0.165 g, 1.00 mmol), triphenylphosphite (0.390 g, 1.25 mmol) and imidazole (0.200 g, 3.00 mmol). After reaction by microwave at 150° C. for 1 h, the mixture was cooled to RT and purified directly using Biotage eluting with EA to give Compound 6 (0.158 g, 54% yield) as a solid. MS (ESI) m/z 292.3 [M+H]⁺. ¹H NMR (DMSO-d₆, 400 MHz) δ: 11.0 (s, 1 H), 7.00 (s, 1H), 5.23 (m, 1H), 2.82 (m, 1H), 2.63 (s, 3H), 2.48-2.52 (m, 2H), 2.49 (s, 3H), 2.15 (m, 1H).

Example 8

Compound 7: 3-(5-amino-2,6-dimethyl-4-oxothieno[2,3-d]pyrimidin-3(4H)-yl)piperidine-2,6-dione

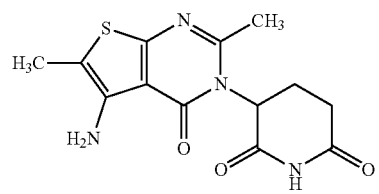 [SMILES: Cc1sc2nc(C)n(C3CCC(=O)NC3=O)c(=O)c2c1N]

3-(2,6-Dimethyl-4-oxothieno[2,3-d]pyrimidin-3(4H)-yl)piperidine-2,6-dione (0.140 g, 0.480 mmol) was dissolved in H₂SO₄ (2 mL) and cooled to 0° C. To this was added a mixture of fuming HNO₃ (1 mL) and H₂SO₄ (0.7 mL). The reaction was stirred for 30 min at 0° C. then quenched with ice followed by the addition of EA and brine. The organic phase was washed with saturated NaHCO₃ (aq) then dried to give 3-(2,6-dimethyl-5-nitro-4-oxothieno[2,3-d]pyrimidin-3(4H)-yl)piperidine-2,6-dione (0.115 g, 71% yield). MS (ESI) m/z 337.3 [M+H]⁺.

To a solution of 3-(2,6-dimethyl-5-nitro-4-oxothieno[2,3-d]pyrimidin-3(4H)-yl)piperidine-2,6-dione (0.110 g, 0.326 mmol) in MeOH (15 mL) and DCM (3 mL) was added a catalytic amount of Pd/C. The mixture was stirred under H₂ for 18 h then filtered through celite. The filtrate was concentrated, and the crude product was purified using Biotage eluting with EA to give Compound 7 (0.020 g, 20% yield). MS (ESI) m/z 307.3 [M+H]⁺. ¹H NMR (DMSO-d₆, 400 MHz) δ: 11.0 (s, 1 H), 5.22 (m, 1H), 5.15 (s, 2H), 2.82 (m, 1H), 2.63 (s, 3H), 2.48-2.52 (m, 2H), 2.49 (s, 3H), 2.15 (m, 1H).

Example 9

Compound 8: 3-(6-bromo-2-methyl-4-oxothieno[2,3-d]pyrimidin-3(4H)-yl)piperidine-2,6-dione

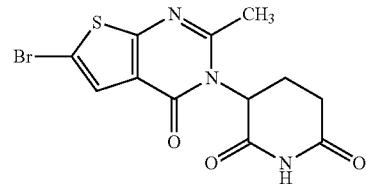 [SMILES: Cc1nc2sc(Br)cc2c(=O)n1C1CCC(=O)NC1=O]

To a solution of 3-(2-methyl-4-oxothieno[2,3-d]pyrimidin-3(4H)-yl)piperidine-2,6-dione (0.075 g, 0.270 mmol) in DMF (4 mL) at RT was added NBS (0.050 g, 0.28 mmol). After stirring at RT for 1 h, the mixture was concentrated then dissolved in EA. The solution was extracted with H₂O then the organic phase was concentrated. Trituration of the residue with EA/hexanes gave Compound 8 (0.085 g, 89% yield). MS (ESI) m/z 357.2 [M+H]⁺. ¹H NMR (DMSO-d₆, 400 MHz) δ: 11.0 (s, 1H), 7.49 (s, 1H), 5.27 (s, 1H), 2.82 (m, 1H), 2.63 (s, 3H), 2.48-2.52 (m, 2H), 2.49 (s, 3H), 2.15 (m, 1H).

Example 10

Compound 9: 3-(7-amino-2-methyl-4-oxothieno[3,2-d]pyrimidin-3(4H)-yl)piperidine-2,6-dione

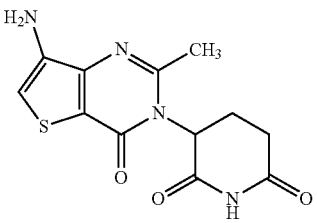 [SMILES: Cc1nc2c(N)csc2c(=O)n1C1CCC(=O)NC1=O]

To a solution of 3-(2-methyl-4-oxothieno[3,2-d]pyrimidin-3(4H)-yl)piperidine-2,6-dione (0.236 g, 0.85 mmol) in DMF (13 mL) at RT was added NBS (0.235 g, 1.32 mmol). After stirring at 110° C. for 3 h, the mixture was cooled to RT, concentrated, and dissolved in EA. The solution was extracted with $H_2O$ then the organic phase was concentrated. Trituration of the residue with EA/hexanes gave 3-(6-bromo-2-methyl-4-oxothieno[3,2-d]pyrimidin-3(4H)-yl)piperidine-2,6-dione (0.250 g, 83% yield). MS (ESI) m/z 357.2 [M+H]$^+$.

To 3-(6-bromo-2-methyl-4-oxothieno[3,2-d]pyrimidin-3(4H)-yl)piperidine-2,6-dione (0.250 g, 0.70 mmol) in $H_2SO_4$ (4 mL) at 0° C. was added a mixture of fuming $HNO_3$ (2 mL) and $H_2SO_4$ (1.4 mL). The reaction was stirred for 30 min at 0° C. then quenched with ice followed by the addition EA and brine. The organic phase was extracted with saturated $NaHCO_3$ (aq) solution then concentrated to give 3-(6-bromo-2-methyl-7-nitro-4-oxothieno[3,2-d]pyrimidin-3(4H)-yl)piperidine-2,6-dione (0.150 g, 53% yield). MS (ESI) m/z 402.1 [M+H]$^+$.

To a solution of 3-(6-bromo-2-methyl-7-nitro-4-oxothieno[3,2-d]pyrimidin-3(4H)-yl)piperidine-2,6-dione (0.150 g, 0.374 mmol) in MeOH (25 mL) was added a catalytic amount of Pd/C. The mixture was stirred under $H_2$ for 3 h then filtered through celite. The filtrate was concentrated and purified using Biotage eluting with EA to give Compound 9 (0.018 g, 17% yield). MS (ESI) m/z 292.3 [M+H]$^+$. $^1$H NMR (DMSO-$d_6$, 400 MHz) δ: 11.0 (s, 1 H), 6.56 (s, 1H), 5.27 (m, 1H), 5.11 (s, 2H), 2.82 (m, 1H), 2.63 (m, 3H), 2.48-2.52 (m, 2H), 2.49 (s, 3H), 2.15 (m, 1H).

Example 11

Compound 10: 3-(5-amino-2-methyl-4-oxothieno[2,3-d]pyrimidin-3(4H)-yl)piperidine-2,6-dione

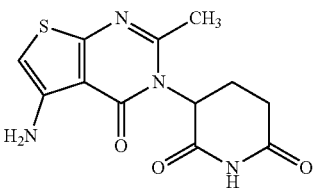 [SMILES: Cc1nc2scc(N)c2c(=O)n1C1CCC(=O)NC1=O]

To a solution of 3-(2-methyl-4-oxothieno[2,3-d]pyrimidin-3(4H)-yl)piperidine-2,6-dione (0.544 g, 1.96 mmol) in DMF (29 mL) at RT was added NBS (0.363 g, 2.03 mmol). The reaction was stirred at RT for 2 h. Additional NBS (0.180 g) was added and the reaction was stirred for 2 h more. The mixture was concentrated then dissolved in EA. The solution was extracted with $H_2O$ then the organic phase was concentrated. Trituration with EA/hexanes gave 3-(6-bromo-2-methyl-4-oxothieno[2,3-d]pyrimidin-3(4H)-yl)piperidine-2,6-dione (0.589 g, 84% yield). MS (ESI) m/z 357.2 [M+H]$^+$.

To a solution of 3-(6-bromo-2-methyl-4-oxothieno[2,3-d]pyrimidin-3(4H)-yl)piperidine-2,6-dione (0.588 g, 1.65 mmol) in $H_2SO_4$ (10 mL) at 0° C. was added fuming $HNO_3$ (100 drops). The reaction was stirred for 90 min at 0° C. then quenched with ice. The resulting solid was filtered and dried to give 3-(6-bromo-2-methyl-5-nitro-4-oxothieno[2,3-d]pyrimidin-3(4H)-yl)piperidine-2,6-dione (0.496 g, 75% yield). MS (ESI) m/z 402.1 [M+H]$^+$.

To a solution of 3-(6-bromo-2-methyl-5-nitro-4-oxothieno[2,3-d]pyrimidin-3(4H)-yl)piperidine-2,6-dione (0.250 g, 0.623 mmol) in MeOH (40 mL) at RT was added a catalytic amount of Pd/C. The mixture was stirred under $H_2$ for 3 h then filtered through celite. After the filtrate was concentrated, the residue was purified using Biotage eluting with EA to give Compound 10 (0.021 g, 12% yield). MS (ESI) m/z 293.3 [M+H]$^+$. $^1$H NMR (DMSO-$d_6$, 400 MHz) δ: 11.0 (s, 1 H), 5.85 (s, 1H), 5.43 (s, 2H), 5.21 (m, 1H), 2.86 (m, 1H), 2.51-2.63 (m, 6H), 2.17 (m, 1H).

Example 12

Compound 11: 3-(7-(aminomethyl)-2-methyl-4-oxothieno[3,4-d]pyrimidin-3(4H)-yl)piperidine-2,6-dione 2,2,2-trifluoroacetate

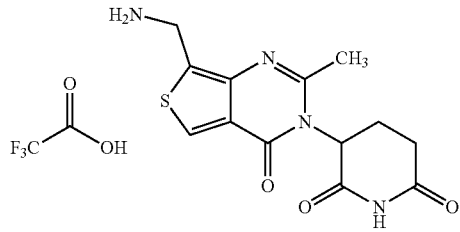 [SMILES: O=C(O)C(F)(F)F ; Cc1nc2c(CN)scc2c(=O)n1C1CCC(=O)NC1=O]

To a solution of methyl 4-aminothiophene-3-carboxylate (3.60 g, 22.8 mmol) in DCM (50 mL) at 0° C. was added TEA (9.5 mL) followed by dropwise addition of acetyl chloride (2.2 g, 34.1 mmol). After stirring at RT for 2 h, the mixture was extracted with $H_2O$ then brine. The organic phase was dried over anhydrous $Na_2SO_4$ then filtered and concentrated to afford methyl 4-acetamidothiophene-3-carboxylate (2.0 g crude, 44% yield) as a solid. MS (ESI) m/z 200.0 [M+H]$^+$.

To a solution of 4-acetamidothiophene-3-carboxylate (2.0 g, 10 mmol) in MeOH (40 mL) at RT was added KOH (1.7 g, 30 mmol). The mixture was stirred at 70° C. for 5 h then cooled to RT and concentrated. The residue was dissolved in $H_2O$ and the solution was extracted with EA. After adjusting the aqueous phase to a pH of 2-3 using 2 N HCl, the mixture was extracted with EA. The combined organic layers were washed with brine, dried over anhydrous $Na_2SO_4$, filtered and concentrated to give 4-acetamidothiophene-3-carboxylic acid (1.8 g, 97% yield) as a solid. MS (ESI) m/z 184.1 [M−H]$^-$.

To a mixture of 4-acetamidothiophene-3-carboxylic acid (1.8 g, 9.7 mmol) and 3-aminopiperidine-2,6-dione (2.4 g, 14.5 mmol) in DMF (20 mL) at RT was added DIEA (4 mL).

To this was added 1-hydroxybenzotriazole (HOBT) (2.0 g, 14.5 mmol) followed by 1-(3-dimethylaminopropyl)-3-ethylcarbodiimide hydrochloride (2.8 g, 14.5 mmol). After stirring at RT for 2 h, the mixture was poured into ice water, filtered, and dried to give 4-acetamido-N-(2,6-dioxopiperidin-3-yl)thiophene-3-carboxamide (2.0 g, 70% yield) as a solid. MS (ESI) m/z 296.1 [M+H]$^+$.

To a suspension of 4-acetamido-N-(2,6-dioxopiperidin-3-yl)thiophene-3-carboxamide (2.0 g, 6.8 mmol) in DMF (20 mL) at RT was added NBS (1.45 g, 8.10 mmol). The mixture was stirred at RT overnight then concentrated and purified using silica gel eluting with DCM/MeOH (30:1) to give 4-acetamido-5-bromo-N-(2,6-dioxopiperidin-3-yl)thiophene-3-carboxamide (1.00 g, 40% yield) as a solid. MS (ESI) m/z 374.0 [M+H]$^+$.

To a solution of 4-acetamido-5-bromo-N-(2,6-dioxopiperidin-3-yl)thiophene-3-carboxamide (1.00 g, 2.68 mmol) in 1-methyl-2-pyrrolidinone (5 mL) at RT was added copper cyanide (725 mg, 8.04 mmol). The mixture was stirred at 180° C. for 2 h under microwave then cooled to RT. After concentration, the residue was purified using silica gel eluting with DCM/MeOH (10:1) to give 4-acetamido-5-cyano-N-(2,6-dioxopiperidin-3-yl)thiophene-3-carboxamide (600 mg crude, 70% yield) as a solid. MS (ESI) m/z 321.1 [M+H]$^+$.

To a suspension of 4-acetamido-5-cyano-N-(2,6-dioxopiperidin-3-yl)thiophene-3-carboxamide (600 mg, 1.88 mmol) in THF (20 mL) at RT was added di-t-butyl dicarbonate (818 mg, 3.75 mmol) and catalytic Raney Ni. The mixture was stirred at 35° C. under H$_2$ overnight then filtered. The filtrate was concentrated and the residue was purified using silica gel eluting with EA to give tert-butyl ((3-acetamido-4-((2,6-dioxopiperidin-3-yl)carbamoyl)thiophen-2-yl)methyl)carbamate (300 mg, 37% yield) as a solid. MS (ESI) m/z 425.1 [M+H]$^+$.

To a suspension of tert-butyl ((3-acetamido-4-((2,6-dioxopiperidin-3-yl)carbamoyl)thiophen-2-yl)methyl)carbamate (300 mg, 0.700 mmol) in xylene (10 mL) and acetic acid (1 mL) at RT was added p-TSA (270 mg, 1.4 mmol). The mixture was stirred at 160° C. for 30 min under microwave then cooled to RT and concentrated. The residue was purified using prep-TLC eluting with DCM/MeOH (5:1) to afford Compound 11 (100 mg, 46% yield) as a solid. MS (ESI) m/z 307.1 [M+H]$^+$.

Example 13

Compound 12: 1-(3-chloro-4-methylphenyl)-3-((3-(2,6-dioxopiperidin-3-yl)-2-methyl-4-oxo-3,4-dihydrothieno[3,4-d]pyrimidin-7-yl)methyl)urea

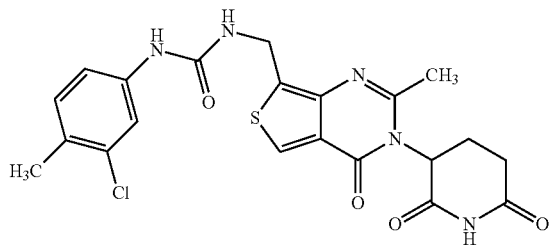 [SMILES: Cc1ccc(NC(=O)NCc2scc3c(=O)n(C4CCC(=O)NC4=O)c(C)nc23)cc1Cl]

To a suspension of 3-(7-(aminomethyl)-2-methyl-4-oxothieno[3,4-d]pyrimidin-3(4H)-yl)piperidine-2,6-dione 2,2,2-trifluoroacetate (50 mg, 0.16 mmol) in THF (4 mL) at RT was added TEA (50 mg, 0.48 mmol) followed by 2-chloro-4-isocyanato-1-methylbenzene (41 mg, 0.24 mmol). The mixture was stirred at RT for 2 h then concentrated. The residue was purified using prep-HPLC eluting with ACN/H$_2$O (0.1% TFA) to afford Compound 12 (18 mg, 23% yield) as a solid. MS (ESI) m/z 474.0 [M+H]$^+$. $^1$H NMR (400 MHz, DMSO-d$_6$) δ 10.97 (s, 1H), 8.68 (s, 1H), 8.29 (s, 1H), 7.65 (d, J 2.0 Hz, 1H), 7.10-7.19 (m, 2H), 6.83 (t, J 5.6 Hz, 1H), 5.16 (dd, J 5.6, 11.6 Hz, 1H), 4.65 (d, J 5.6 Hz, 2H), 2.79-2.83 (m, 1H), 2.57-2.67 (m, 5H), 2.23 (s, 3H), 2.11-2.16 (m, 1H).

Example 14

Compound 13: 1-(3-chloro-4-methylphenyl)-3-((3-(2,6-dioxopiperidin-3-yl)-2-methyl-4-oxo-3,4-dihydrothieno[3,2-d]pyrimidin-6-yl)methyl)urea

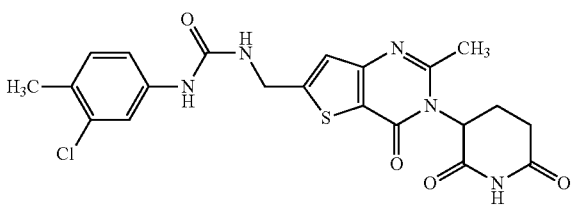 [SMILES: Cc1ccc(NC(=O)NCc2cc3nc(C)n(C4CCC(=O)NC4=O)c(=O)c3s2)cc1Cl]

A mixture of methyl 3-amino-5-bromothiophene-2-carboxylate (1.40 g, 5.96 mmol), acetic anhydride (5.0 mL) and acetic acid (5.0 mL) was stirred at 110° C. for 4 h then cooled to RT. After concentration, saturated NaHCO$_3$ (aq) solution was added and the mixture was extracted with DCM. The organic phase was dried over anhydrous Na$_2$SO$_4$, filtered, and concentrated to give methyl 3-acetamido-5-bromothiophene-2-carboxylate (1.60 g, 97% yield) as a solid. MS (ESI) m/z 277.9, 280.9 [M+H]$^+$.

To a solution of methyl 3-acetamido-5-bromothiophene-2-carboxylate (1.20 g, 4.33 mmol) in DMF (24 mL) at RT was added zinc cyanide (559 mg, 4.76 mmol), tris(dibenzylideneacetone)dipalladium (374 mg, 0.43 mmol) and 1,1'-bis(diphenylphosphino)ferrocene (528 mg, 0.95 mmol). The mixture was stirred at 150° C. under microwave for 1 h then cooled to RT. After concentration, the residue was purified using silica gel eluting with petroleum ether/EA (1:1) to give methyl 3-acetamido-5-cyanothiophene-2-carboxylate (900 mg, 93% yield) as a solid. MS (ESI) m/z 225.0 [M+H]$^+$.

A mixture of methyl 3-acetamido-5-cyanothiophene-2-carboxylate (900 mg, 4.02 mmol), di-t-butyl dicarbonate (1.75 g, 8.04 mmol) and Raney Ni (100 mg) in MeOH (30 mL) was stirred at RT for 1 h under H$_2$. The mixture was filtered and the residue was rinsed with MeOH. The combined organic solution was concentrated and purified using silica gel eluting with petroleum ether/EA (1:1) to give methyl 3-acetamido-5-(((tert-butoxycarbonyl) amino)methyl)thiophene-2-carboxylate (720 mg, 55% yield) as an oil. MS (ESI) m/z 273.1 [M-55]$^+$.

A mixture of methyl 3-acetamido-5-(((tert-butoxycarbonyl)amino) methyl)thiophene-2-carboxylate (720 mg, 2.20 mmol) and lithium hydroxide monohydrate (138 mg, 3.30 mmol) in H$_2$O (5.50 mL) and THF (5.50 mL) was stirred at RT for 6 h. The mixture was concentrated and H$_2$O was added. After extraction with DCM, the aqueous phase was acidified to a pH of 4 using 1N HCl. The resulting suspension was filtered, and the residue was washed with H$_2$O then dried to give 3-acetamido-5-(((tert-butoxycarbonyl)amino)

methyl)thiophene-2-carboxylic acid (614 mg, 89% yield) as a solid. MS (ESI) m/z 259.1 [M-55]⁺.

To a solution of 3-acetamido-5-(((tert-butoxycarbonyl)amino)methyl) thiophene-2-carboxylic acid (614 mg, 1.96 mmol) in DMF (40 mL) at RT was added 3-aminopiperidine-2,6-dione hydrochloride (387 mg, 2.35 mmol) followed by HOBT (397 mg, 2.94 mmol), N-(3-dimethylaminopropyl)-N'-ethylcarbodiimide hydrochloride (564 mg, 2.94 mmol), and DIEA (760 mg, 5.86 mmol). The mixture was stirred at RT for 16 h then concentrated. After the addition of H₂O, the mixture was extracted with DCM, and the organic phase was concentrated. The residue was purified using silica gel eluting with petroleum ether/EA (1:1) to give tert-butyl ((4-acetamido-5-((2,6-dioxopiperidin-3-yl)carbamoyl)thiophen-2-yl)methyl) carbamate (280 mg, 34% yield) as a solid. MS (ESI) m/z 369.1 [M-55]⁺.

A mixture of tert-butyl ((4-acetamido-5-((2,6-dioxopiperidin-3-yl)carbamoyl) thiophen-2-yl)methyl)carbamate (242 mg crude, 0.57 mmol estimated) and p-toluenesulfonic acid monohydrate (217 mg, 1.14 mmol) in xylene/acetic acid (2.0 mL:0.2 mL) was heated under microwave at 160° C. for 30 min then cooled to RT. The mixture was concentrated and the residue was purified by prep-TLC eluting with DCM/MeOH (5:1) to give 3-(6-(aminomethyl)-2-methyl-4-oxothieno[3,2-d]pyrimidin-3(4H)-yl)piperidine-2,6-dione 4-methylbenzenesulfonate (264 mg crude) as a solid. MS (ESI) m/z 307.0 [M+H]⁺.

A mixture of 3-(6-(aminomethyl)-2-methyl-4-oxothieno[3,2-d]pyrimidin-3(4H)-yl)piperidine-2,6-dione 4-methylbenzenesulfonate (224 mg crude, 0.45 mmol estimated), 2-chloro-4-isocyanato-1-methylbenzene (75 mg, 0.45 mmol), and TEA (91 mg, 0.90 mmol) in THF (10 mL) was stirred at RT for 16 h. The mixture was concentrated and the residue was purified by prep-HPLC eluting with ACN/H₂O (0.1% TFA) to afford Compound 13 (38.6 mg, 18% yield) as a white solid. MS (ESI) m/z 474.0, 475.0 [M+H]⁺. ¹H NMR (400 MHz, DMSO-d₆) δ 11.00 (s, 1H), 8.84 (s, 1H), 7.64 (d, J 2.0, 1H), 7.20-7.14 (m, 3H), 6.95-6.92 (m, 1H), 5.30-5.26 (m, 1H), 4.54 (d, J 6.0, 2H), 2.85-2.78 (m, 1H), 2.68-2.56 (m, 5H), 2.23 (s, 3H), 2.17-2.15 (m, 1H).

Example 15

Compound 14: (S)-3-(5-Methyl-7-oxo-1-thia-4,6-diaza-6H-inden-6-yl)-2,5-pyrrolidinedione

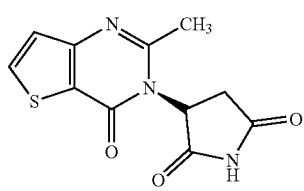

A solution of methyl 3-aminothiophene-2-carboxylate (0.546 g, 3.47 mmol) in acetic anhydride (4 mL) was heated at 140° C. under microwave for 25 min then cooled to RT and concentrated. H₂O was added and the resulting solid was filtered and dried to give methyl 3-acetamidothiophene-2-carboxylate (0.674 g, quantitative yield) as a solid. MS (ESI) m/z 200.2 [M+H]⁺.

To a solution of methyl 3-acetamidothiophene-2-carboxylate (0.674 g, 3.47 mmol) in MeOH (20 mL) at RT was added NaOH (0.416 g, 10.4 mmol). The mixture was stirred at 50° C. for 16 h then concentrated. 1N HCl was added and the resulting solid was filtered and dried to give 3-acetamidothiophene-2-carboxylic acid (0.642 g, 88% yield) as a solid. MS (ESI) m/z 186.2 [M+H]⁺.

To a solution of 3-acetamidothiophene-2-carboxylic acid (0.200 g, 1.08 mmol) in ACN (3 mL) at RT was added imidazole (0.184 g, 2.7 mmol) followed by triphenyl phosphite (0.502 g, 1.62 mmol) and (S)-3-amino-2-pyrrolidinone hydrochloride. (0.147 g, 1.08 mmol). The mixture was heated at 150° C. under microwave for 1 h then cooled to RT and concentrated. The residue was purified using silica gel eluting 0 to 10% MeOH in DCM to afford 6-[(S)-2-oxo-3-pyrrolidinyl]-5-methyl-1-thia-4,6-diaza-6H-inden-7-one (0.242 g, 90% yield) as a solid. MS (ESI) m/z 250.3 [M+H]⁺.

A solution of 6-[(S)-2-oxo-3-pyrrolidinyl]-5-methyl-1-thia-4,6-diaza-6H-inden-7-one (0.100 g, 0.40 mmol) in ACN (3 mL) at RT was bubbled with N₂ for 5 min. Dess-Martin periodinane (0.332 g, 1.20 mmol) and 15 drops of wet DMSO were added at RT and the mixture was heated at 120° C. under microwave for 60 min then cooled to RT and concentrated. To the residue was added 10% MeOH in EA and aqueous Na₂S₂O₃. The mixture was extracted with sat. aqueous NaHCO₃ (4 mL) followed by brine. The organic phase was concentrated, and the residue was purified using silica gel eluting with 0 to 10% MeOH in EA to afford Compound 14 (0.012 g, 11% yield) as a solid. MS (ESI) m/z 264.3 [M+H]⁺. ¹H NMR (400 MHz, DMSO-d6) δ 11.488 (s, 1 H), 8.21 (d, 1 H), 7.40 (d, 1H), 5.58-5.49 (m, 1H), 3.138-3.084 (m, 1 H), 2.798-2.766 (m, 1H), 2.65 (s, 3H).

Example 16

Compound 15: (S)-3-(5-Methyl-7-oxo-1-thia-4,6-diaza-6H-inden-6-yl)-2,7-azepanedione

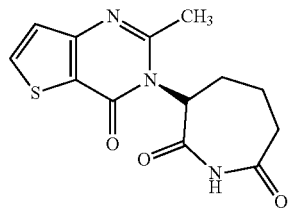

To a solution of 3-acetamidothiophene-2-carboxylic acid (0.250 g, 1.35 mmol) in ACN (4 mL) at RT was added imidazole (0.294 g, 4.32 mmol) followed by triphenyl phosphite (0.628 mg, 2.02 mmol) and (S)-3-amino-2-oxo-azepane, HCl (0.222 g, 1.35 mmol). The mixture was heated at 150° C. under microwave for 60 min then cooled to RT and concentrated. H₂O was added, and the mixture was extracted with EA. After the organic phase was concentrated, the residue was purified using silica gel eluting with 5-15% MeOH in EA to give 6-[(S)-2-oxo-3-azepanyl]-5-methyl-1-thia-4,6-diaza-6H-inden-7-one (160 mg, 43% yield) as a solid. MS (ESI) m/z 278 [M+H]⁺.

A suspension of 6-[(S)-2-oxo-3-azepanyl]-5-methyl-1-thia-4,6-diaza-6H-inden-7-one (100 mg, 0.360 mmol) in ACN (4 mL) and wet DMSO (8 drops using a glass pipet) at RT was bubbled N₂ for 5 min. Dess-Martin periodinane (0.306 g, 0.721 mmol) was added at RT and the mixture was heated at 120° C. under microwave for 60 min then cooled to RT. After aqueous Na₂S₂O₃ (4 mL) and sat. aqueous NaHCO₃(4 mL) were added, the mixture was stirred for 10 min then extracted with EA. The organic phase was concentrated and purified using Biotage eluting with 1-10% MeOH in EA to afford Compound 15 (16 mg, 15% yield) as a solid. MS (ESI) m/z 292 [M+H]$^+$. $^1$H NMR (400 MHz, DMSO-d6) δ 10.72 (s, 1 H), 8.14-8.16 (d, 1H), 7.32-7.34 (d, 1H), 5.22-5.24 (d, 1H), 3.08-3.14 (m, 1H), 2.75-2.81 (m, 1H), 2.68 (s, 3H), 2.48-2.53 (m, 1H), 2.04-2.08 (m, 1H), 1.99-2.03 (m, 1H), 1.86-1.98 (m, 1H).

Example 17

Biological Assays

Western Blot Analysis

MV-4-11 cells were grown in RPMI 1640 media supplemented with 10% fetal bovine serum, streptomycin and penicillin.

Cells were cultured at approximately 10$^6$ cells per mL and incubated in DMSO or the indicated compounds for 6-8 hours. Whole cell extracts were prepared using RIPA buffer according to manufacturer's protocol (Pierce). Briefly, 3×10$^6$ cells were washed once in PBS, the cell pellets were resuspended in RIPA buffer and allowed to incubate for 15 minutes on ice. Cells debris was removed by centrifugation and the cleared whole cell lysates were transferred to new tubes for further analysis.

For Western blot analysis, whole cell protein extracts were separated on 4-12% SDS-polyacrylamide gels, transferred to nitrocellulose and probed with the indicated primary antibodies. Membranes were subsequently washed and probed with the appropriate IRDye secondary antibodies (LI-COR). The signal was detected using the Odyssey Imaging System (LI-COR).

The following antibodies were used in these studies: Anti-eRF3/GSPT1: Abcam, ab126090 (Cambridge, Mass.); Anti-Ikaros: Abcam, ab191394 (Cambridge, Mass.); Anti-CK1α: Abcam, ab108296 (Cambridge, Mass.); Anti-PDE6D: Santa Cruz Biotechnology, sc-166854 (Dallas, Tex.); β-actin (8H10D10) mouse monoclonal antibody: Cell Signaling Technology, #3700 (Danvers, Mass.); IRDye 680RD Goat anti-rabbit antibody: LI-COR, 926-68071 (Lincoln, Nebr.); IRDye 800CW Goat anti-mouse antibody: LI-COR, 926-32210 (Lincoln, Nebr.).

IKAROS activity is shown in Table 1. CK-1α activity is shown in Table 2. GSPT1 activity is shown in Table 3. Helios activity is shown in Table 4. PDE6 activity is shown in Table 5.

TABLE 1

Activity of Compounds 2, 10, 12, and 13 in IKAROS degradation assay. Compounds tested at 30 μM and 15 μM.

| Compound No. | IKAROS % Degradation at 30 μM | IKAROS % Degradation at 15 μM |
|---|---|---|
| 2 | 7 | 0 |
| 10 | 53 | 49 |
| 12 | 60 | 28 |
| 13 | 55 | 65 |

TABLE 2

Activity of Compounds 8, 9, 11, 12, and 13 in CK1α degradation assay. Compounds tested at 30 μM and 15 μM.

| Compound No. | CK1α % Degradation at 30 μM | CK1α % Degradation at 15 μM |
|---|---|---|
| 8 | 0 | 8 |
| 9 | 12 | 24 |
| 11 | 0 | 17 |
| 12 | 45 | 16 |
| 13 | 35 | 31 |

TABLE 3

Activity of Compound 1, 12 and 13 in GSPT1 degradation assay. Compounds tested at 30 μM and 15 μM.

| Compound No. | GSPT1 % Degradation at 30 μM | GSPT1 % Degradation at 15 μM |
|---|---|---|
| 1 | 0 | 23 |
| 12 | 97 | 96 |
| 13 | 87 | 87 |

TABLE 4

Activity of Compound 10, 12, and 13 in Helios assay. Compounds tested at 30 μM and 15 μM.

| Compound No. | Helios % Degradation at 30 μM | Helios % Degradation at 15 μM |
|---|---|---|
| 10 | 16 | 0 |
| 12 | 69 | 49 |
| 13 | 21 | 50 |

TABLE 5

Activity of Compound 2, 3, 4, 5, 11, 12, and 13 in PDE6 degradation assay. Compounds tested at 30 μM and 15 μM.

| Compound No. | PDE6D % Degradation at 30 μM | PDE6D % Degradation at 15 μM |
|---|---|---|
| 2 | 24 | 0 |
| 3 | 10 | 0 |
| 4 | 75 | 49 |
| 5 | 15 | 0 |
| 11 | 41 | 30 |
| 12 | 21 | 0 |
| 13 | 9 | 4 |

Cell Viability Assay

MV-4-11 cells were cultured in RPMI 1640 media supplemented with 10% fetal bovine serum, streptomycin and penicillin, and were plated in white walled 96-well plates at 2500 cells/well. Cells were incubated in DMSO (control) or the indicated compounds for 3 days at 37° C. and 5% CO$_2$. Following the incubation period, 100 μL of CellTiterGlow (CTG) reagent (CellTiter-Glo® Luminescent Cell Viability Assay, Promega (Madison, Wis.)) was added to each well. Following a 10 minutes incubation with shaking, luminescence was measured using the EnVision Multimode plate reader.

Antiproliferative activity of compounds in MV-4-11 cell viability assay is shown in Table 6.

TABLE 6

Activity of Compounds 3, 4, 6, 7, 11, 12, 13 in MV-4-11 cell viability assays. Compounds tested at 30 μM and 15 μM.

| Compound No. | MV-4-11 Cell Viability % DMSO at 30 μM | MV-4-11 Cell Viability % DMSO at 15 μM |
|---|---|---|
| 3 | 94 | 97 |
| 4 | 97 | 100 |
| 6 | 91 | 89 |
| 7 | 96 | 97 |
| 11 | 78 | 94 |
| 12 | 0 | 0 |
| 13 | 0.73 | 2 |

As illustrated in Table 6, Compound 12 inhibits cancer cell viability, such as leukemia cell viability. Compound 12 reduced cell viability of MV-4-11 to 0% of DMSO control both at 30 μM and 15 μM. Compound 13 reduced cell viability of MV-4-11 to 0.73% and 2% of DMSO control at 30 μM and 15 μM, respectively.

Cell-Based Assay

Either frozen primary blood mononuclear cells (PBMCs) or frozen $CD_{14}$+ mobilized peripheral blood monocytes were purchased from AllCells (PB003F, Normal Peripheral Blood MNC (Alameda, Calif.)). Cells were quick thawed, washed 1-time with RPMI-1640 (10% FBS/1% Pen-Strep) and plated in 96 well plates at 200,000 cells per well. Cells were pretreated with DMSO only or Compound 12 for 1 h and then induced with 100 ng/mL lipopolysaccharide (LPS) for 18-24 h. The supernatant was analyzed for IL-1β, IL-6, and TNFα, using Meso Scale assay according to manufacturer's protocol. The negative control wells were treated with DMSO.

For the IL-2 analysis, 96 well plates were precoated with 1 μg/mL anti-human $CD_3$ antibody (OKT3, eBioscience Inc., San Diego, Calif.). After washing with PBS, Compound 12 was added (50 μL/well) followed by PBMCs diluted at 3-4 million cells/mL (150 μL/well). Plates were incubated for 24 h and the supernatants collected for Mesoscale IL-2 analysis. IL-2 activity is measured as fold difference from the DMSO control.

Activity of Compound 12 in IL-1β, IL-6, TNFα, and IL-2 assays is shown in Table 7. Compound 12 was tested at 10 μM and 1 μM.

TABLE 7

| Compound 12 Concentration | IL-1β % Inhibition | IL-6 % Inhibition | TNFα % Inhibition | IL-2 Fold Change |
|---|---|---|---|---|
| 10 μM | 92 | 53 | 91 | 3.1 |
| 1 μM | 80 | 17 | 79 | 3.6 |

As illustrated in Table 7, Compound 12 demonstrated inhibitory effects on IL-1β, IL-6, and TNFα and stimulatory effects on IL-2. Compound 12 also showed a fold change of 3.1 and 3.6 from the DMSO control, respectively, at 10 μM and 1 μM, indicating that Compound 12 stimulated IL-2 production as compared to the DMSO control.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' containing,' or 'characterized by,' and is inclusive or open-ended and does not exclude additional, unrecited elements or method steps; the term 'includes' should be interpreted as 'includes but is not limited to,' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The mere fact that certain measures are recited in mutually different dependent claims does not indicate that a combination of these measures cannot be used to advantage.

It will be further understood by those within the art that if a specific number of an introduced claim recitation is intended, such an intent will be explicitly recited in the claim, and in the absence of such recitation no such intent is present. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A compound of: Formula (I):

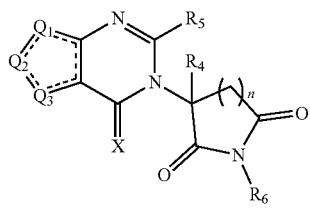

or a pharmaceutically acceptable salt or solvate thereof, wherein:
$Q_1$ is $CR_1$ or —S—;
$Q_2$ is $CR_2$ or —S—;
$Q_3$ is $CR_3$ or —S—;
wherein one of $Q_1$, $Q_2$, and $Q_3$ is —S—;
each ═══ is a single or double bond;
each of $R_1$, $R_2$, and $R_1$ is independently hydrogen, deuterium, hydroxyl, halogen, cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy, a substituted or unsubstituted $C_1$-$C_6$, alkyl, a substituted or unsubstituted $C_2$-$C_6$ alkenyl, a substituted or unsubstituted $C_2$-$C_6$ alkynyl, a substituted or unsubstituted $C_1$-$C_6$ haloalkyl, a substituted or unsubstituted $C_3$-$C_8$ cycloalkyl, a substituted or unsubstituted $C_6$-$C_{10}$ aryl, a substituted or unsubstituted 3-10 membered heterocyclyl, or a substituted or unsubstituted 5-10 membered heteroaryl;
each of $R_4$ and $R_5$ is independently selected from the group consisting of hydrogen, deuterium, halogen, and a substituted or unsubstituted $C_1$-$C_6$ alkyl;
$R_6$ is selected from the group consisting of hydrogen, deuterium, hydroxy, a substituted or unsubstituted $C_1$-$C_6$ alkyl, and a substituted or unsubstituted $C_1$-$C_6$ alkoxy;
X is O, NH, or S; and
n is 1, 2, or 3.

2. A compound of Formula (II):

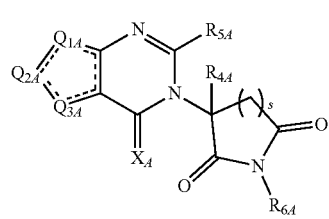

or a pharmaceutically acceptable salt or solvate thereof, wherein:
$Q_{1A}$ is $CR_{1A}$ or —S—;
$Q_{2A}$ is $CR_{2A}$ or —S—;
$Q_{3A}$ is $CR_{3A}$ or —S—;
each ═══ is a single or double bond;
wherein one of $Q_1$, $Q_2$, and $Q_3$ is —S—;
each of $R_{1A}$, $R_{2A}$, and $R_{3A}$ is independently hydrogen, deuterium, hydroxyl, halogen, cyano, nitro, a substituted or unsubstituted amino, a substituted or unsubstituted, C-amido, a substituted or unsubstituted, N-amido, a substituted or unsubstituted ester, a substituted or unsubstituted urea, a substituted or unsubstituted $C_1$-$C_6$ alkoxy, a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted $C_1$-$C_6$ haloalkyl, a substituted or unsubstituted $C_3$-$C_8$ cycloalkyl, a substituted or unsubstituted $C_6$-$C_{10}$ aryl, a substituted or unsubstituted 3-10 membered heterocyclyl, a substituted or unsubstituted 5-10 membered heteroaryl,

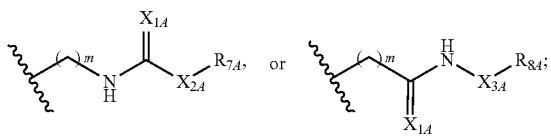

wherein one of $R_{1A}$, $R_{2A}$, and $R_{3A}$ is

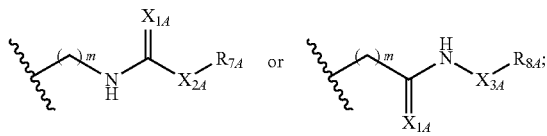

each of $R_{4A}$ and $R_{5A}$ is independently selected from the group consisting of hydrogen, deuterium, halogen, and a substituted or unsubstituted $C_1$-$C_6$ alkyl;
$R_{6A}$ is selected from the group consisting of hydrogen, deuterium, hydroxy, a substituted or unsubstituted $C_1$-$C_6$ alkyl, and a substituted or unsubstituted $C_1$-$C_6$ alkoxy;
$X_A$ is O, NH, or S;
s is 1, 2, or 3;
each $X_{1A}$ is independently O, NH, or S;
each $X_{2A}$ is independently selected from the group consisting of —$NR_{9A}$—, —$(CH_2)_h$—$(NR_{9A})$—$(CH_2)_i$—, —$(CH_2)_h$—$(NR_{9A})$—$(CH_2)_i$—$(NR_{9A})$—, —$(CH_2)_{1-5}$—, —$(CF_2)_{1-5}$—, —$(CD_2)_{1-5}$—, —O—, —C(═O)—, and —S—;

each $X_{3A}$ is independently selected from the group consisting of —$(CH_2)_t$—$(NR_{9A})$—$(CH_2)_j$—, —$(CH_2)_t$—$(NR_{9A})$—$(CH_2)_j$—$(NR_{9A})$—, —$(CH_2)_{1-5}$—, —$(CF_2)_{1-5}$—, and —$(CD_2)_{1-5}$—;

each m is independently 0, 1, 2; 3, 4, or 5;

each h, i, and j is independently 0, 1, 2, 3, 4, or 5;

each t is independently 1, 2, 3, 4, or 5;

each $R_{7A}$ and $R_{8A}$ is independently selected from the group consisting of a substituted or unsubstituted $C_3$-$C_{10}$ cycloalkyl, a substituted or unsubstituted $C_6$-$C_{10}$ aryl, a substituted or unsubstituted 5-10 membered heteroaryl, a substituted or unsubstituted 3-10 membered heterocyclyl, and a substituted or unsubstituted $C_1$-$C_{10}$ alkyl; and $R_{9A}$ is hydrogen, or a substituted or unsubstituted $C_1$-$C_6$ alkyl.

3. The compound of claim 2, wherein each $X_{2A}$ is independently selected from the group consisting of —$NR_{9A}$—, —$(CH_2)_h$—$(NR_{9A})$—$(CH_2)_i$—, —$(CH_2)_h$—$(NR_{9A})$—$(CH_2)_i$—$(NR_{9A})$—, —$(CH_2)_{1-5}$—, —$(CF_2)_{1-5}$—, —$(CD_2)_{1-5}$—, —O—, and —S—.

4. The compound of claim 2, wherein the compound of Formula (II) is represented by Formula (IIa), (IIb), or (IIc),

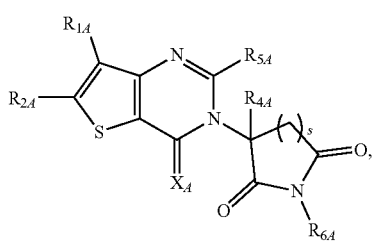

(IIa)

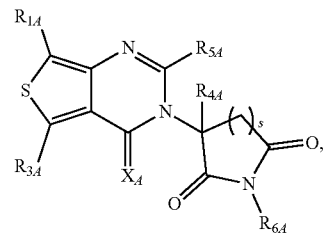

(IIb)

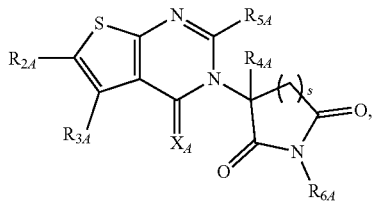

(IIc)

or a pharmaceutically acceptable salt thereof.

5. The compound of claim 2, wherein s is 2.

6. The compound of claim 2, wherein $R_{4A}$ is hydrogen, halogen, or an unsubstituted $C_1$-$C_6$ alkyl.

7. The compound of claim 2, wherein $R_{5A}$ is hydrogen, halogen, or an unsubstituted $C_1$-$C_6$ alkyl.

8. The compound of claim 2, wherein $R_{6A}$ is hydrogen, or a substituted or unsubstituted $C_1$-$C_6$ alkyl.

9. The compound of claim 2, wherein $X_A$ is O.

10. The compound of claim 4, wherein the compound of Formula (II) is represented by Formula (IIa), and wherein one of $R_{1A}$ and $R_{2A}$ is

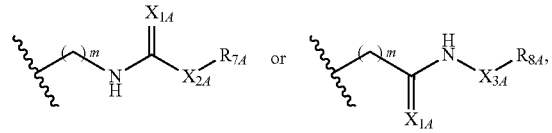

and the other of $R_{1A}$ and $R_{2A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted phenyl, a substituted or unsubstituted 4-6 membered heterocyclyl, or a substituted or unsubstituted 5 or 6 membered heteroaryl.

11. The compound of claim 10, wherein one of $R_{1A}$ and $R_{2A}$ is

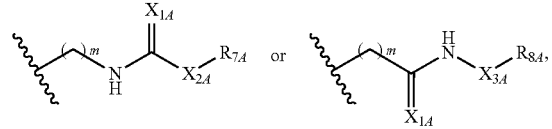

and the other of $R_{1A}$ and $R_{2A}$ is hydrogen.

12. The compound of claim 4, wherein the compound of Formula (II) is represented by Formula (IIb), and wherein one of $R_{1A}$ and $R_{3A}$ is

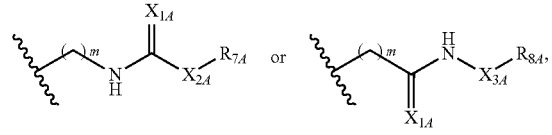

and the other of $R_{1A}$ and $R_{3A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted phenyl, a substituted or unsubstituted 4-6 membered heterocyclyl, or a substituted or unsubstituted 5 or 6 membered heteroaryl.

13. The compound of claim 12, wherein one of $R_{1A}$ and $R_{3A}$ is

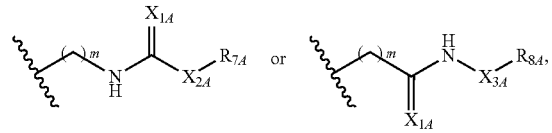

and the other of $R_{1A}$ and $R_{3A}$ is hydrogen.

14. The compound of claim 4, wherein the compound of Formula (II) is represented by Formula (IIc), and wherein one of $R_{2A}$ and $R_{3A}$ is

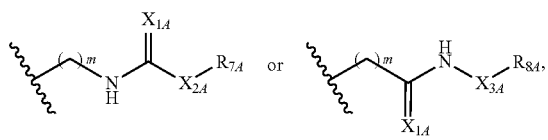

and the other of $R_{2A}$ and $R_{3A}$ is hydrogen, deuterium, hydroxyl, halogen, cyano, nitro, an unsubstituted amino, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted phenyl, a substituted or unsubstituted 4-6 membered heterocyclyl, or a substituted or unsubstituted 5 or 6 membered heteroaryl.

15. The compound of claim 14, wherein one of $R_{2A}$ and $R_{3A}$ is

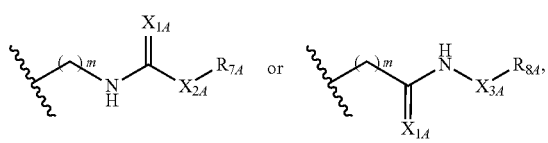

and the other of $R_{2A}$ and $R_{3A}$ is hydrogen.

16. The compound of claim 2, wherein m is 1 or 2.

17. The compound of claim 2, wherein $X_{1A}$ is O.

18. The compound of claim 2, wherein $X_{2A}$ is —$NR_{9A}$—, —$(CH_2)_h$—$(NR_{9A})$—$(CH_2)_i$— or —$(CH_2)_h$—$(NR_{9A})$—$(CH_2)_i$—$(NR_{9A})$—; wherein $R_{9A}$ is hydrogen or an unsubstituted $C_1$-$C_6$ alkyl; and each of h and i is independently 0 or 1.

19. The compound of claim 2, wherein $X_{2A}$ is —C(=O)— or —$(CH_2)_{1-5}$—.

20. The compound of claim 2, wherein $X_{3A}$ is —$(CH_2)_t$—$(NR_{9A})$—$(CH_2)_j$— or —$(CH_2)_t$—$(NR_{9A})$—$(CH_2)_j$—$(NR_{9A})$—; wherein $R_{9A}$ is hydrogen; t is 1 or 2; and j is 0, 1 or 2.

21. The compound of claim 2, wherein each of $R_{7A}$ and $R_{8A}$ is independently selected from the group consisting of a substituted or unsubstituted $C_3$-$C_6$ cycloalkyl, a substituted or unsubstituted phenyl, a substituted or unsubstituted naphthyl, a substituted or unsubstituted 5 or 6 membered heteroaryl, a substituted or unsubstituted 3-7 membered heterocyclyl, and a substituted or unsubstituted $C_1$-$C_6$ alkyl.

22. The compound of claim 21, wherein each of $R_{7A}$ and $R_{8A}$ is independently a phenyl substituted with one, two or three substituents selected from the group consisting of halogen, an unsubstituted $C_1$-$C_6$ alkyl, substituted or unsubstituted $C_3$-$C_6$ cycloalkyl, substituted or unsubstituted heterocyclyl, an (unsubstituted $C_1$-$C_6$ alkyl)amine, —N($C_1$-$C_3$ alkyl)$_2$, —NH($C_1$-$C_3$ alkyl), an substituted or unsubstituted $C_3$-$C_7$ cycloalkyl(unsubstituted $C_1$-$C_6$ alkyl), and an substituted or unsubstituted heterocyclyl (unsubstituted $C_1$-$C_6$ alkyl).

23. The compound of claim 22, wherein each of $R_{7A}$ and $R_{8A}$ is independently a phenyl substituted with one or two substituents selected from the group consisting of halogen, —N($C_1$-$C_3$ alkyl)$_2$, —NH($C_1$-$C_3$ alkyl), and an unsubstituted $C_1$-$C_6$ alkyl.

24. The compound of claim 2, selected from the group consisting of

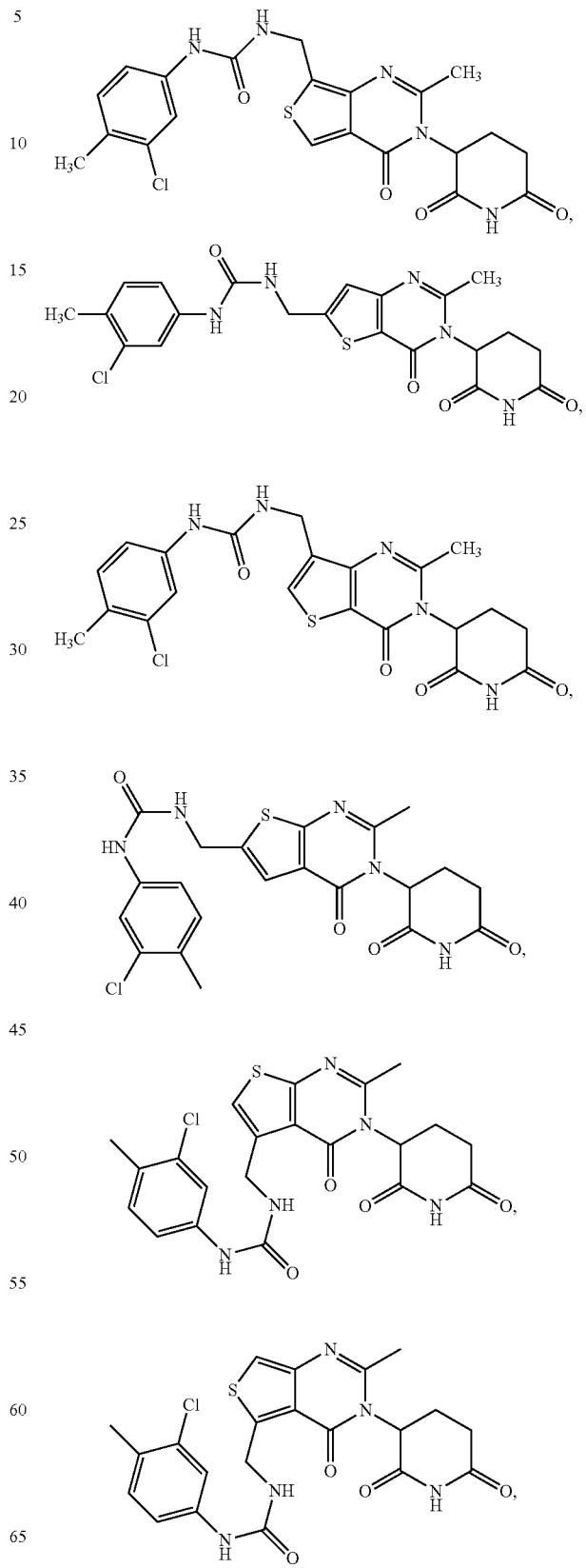

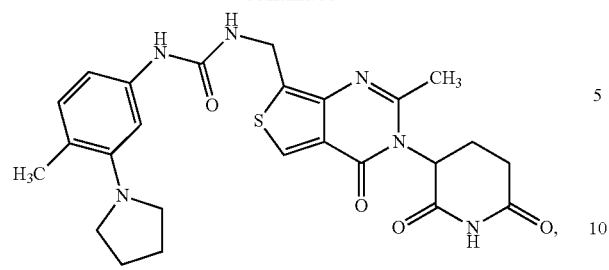
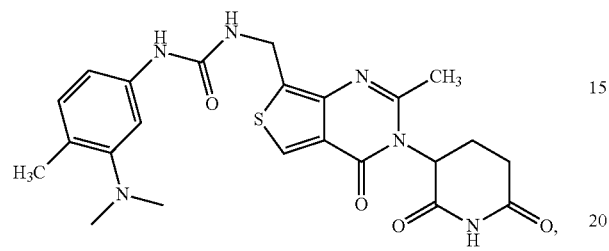
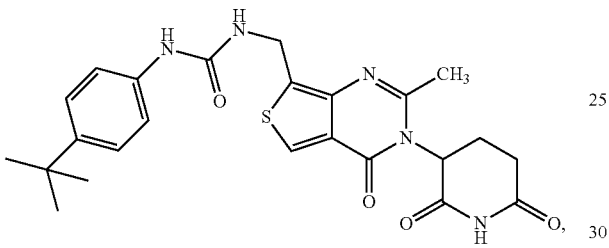
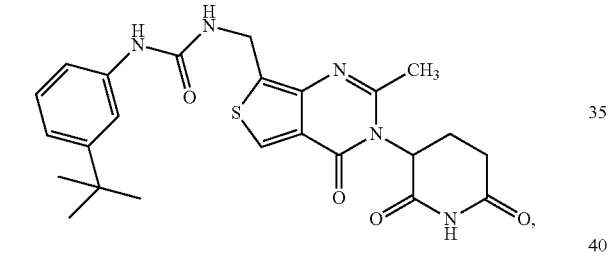
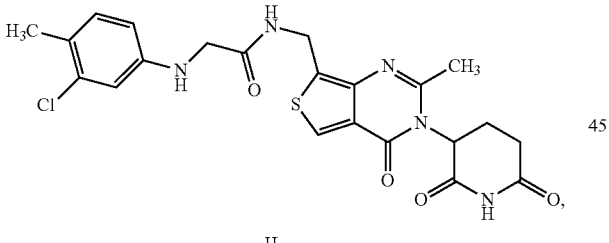
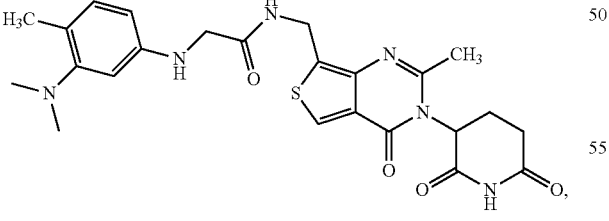
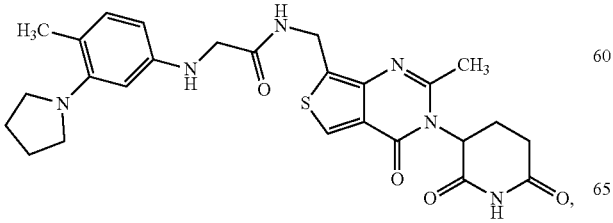
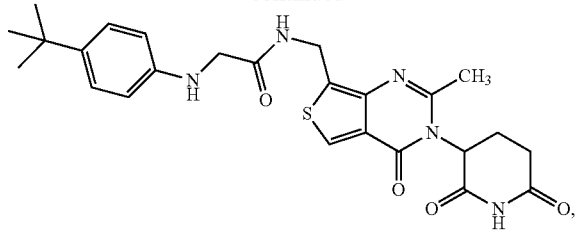
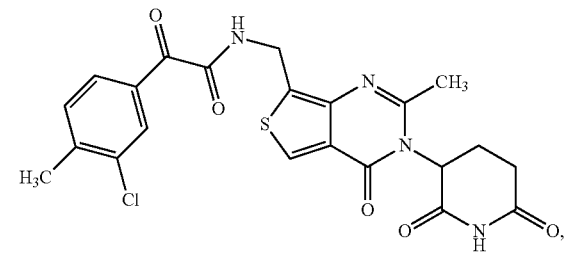
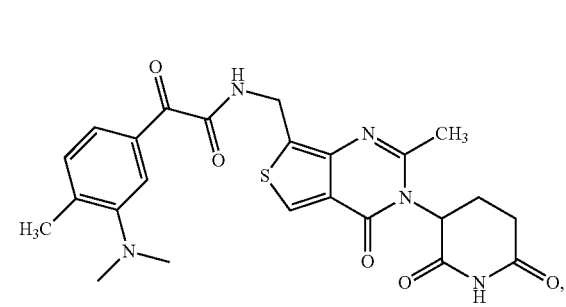
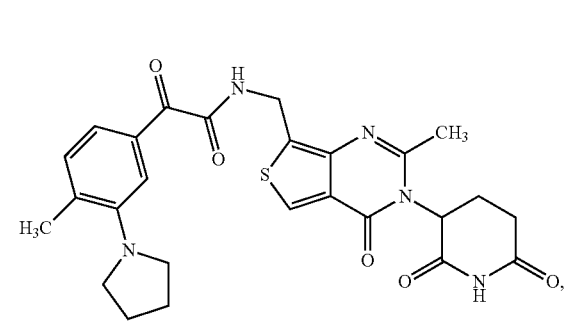
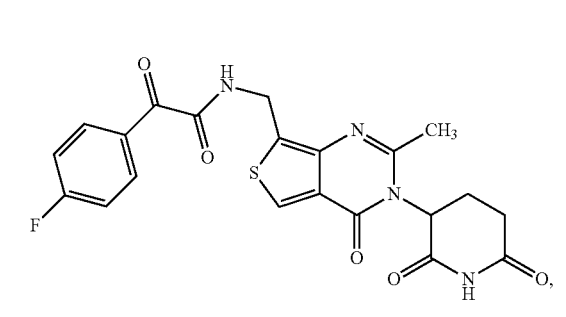
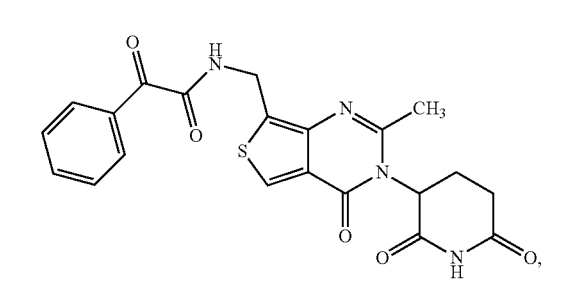

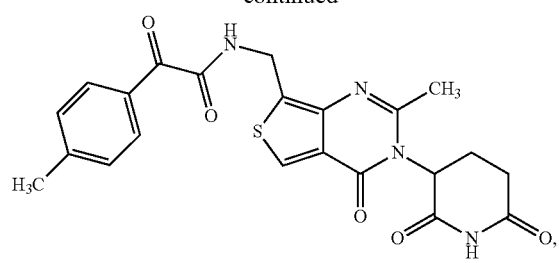
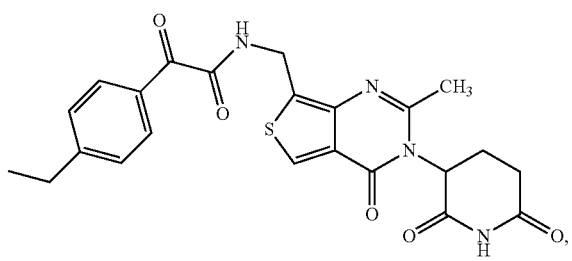
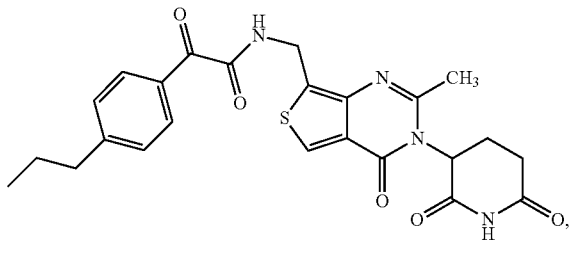
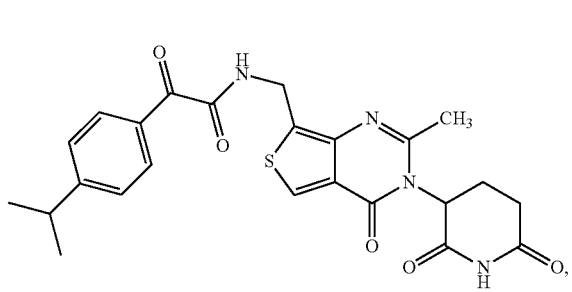
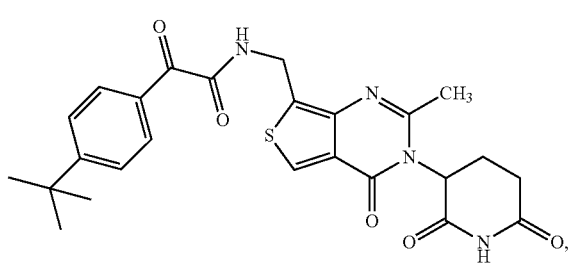
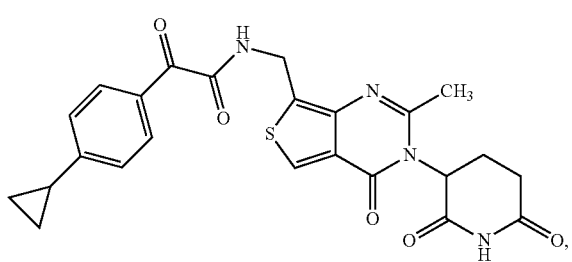
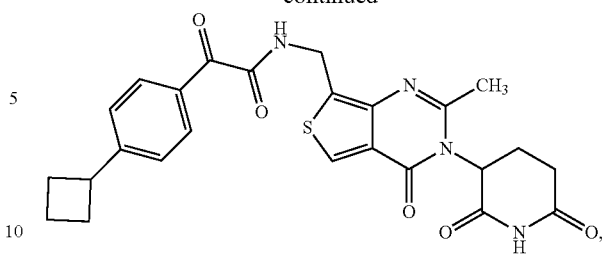
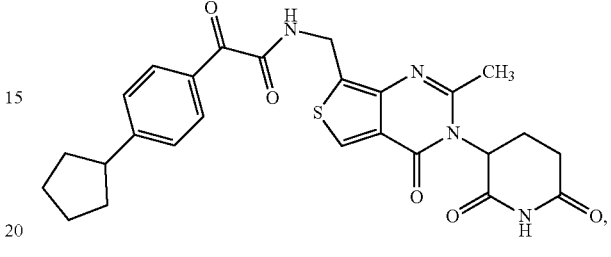
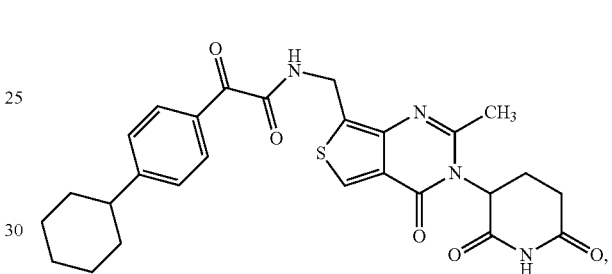
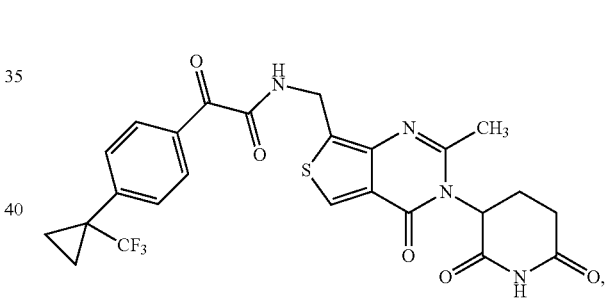
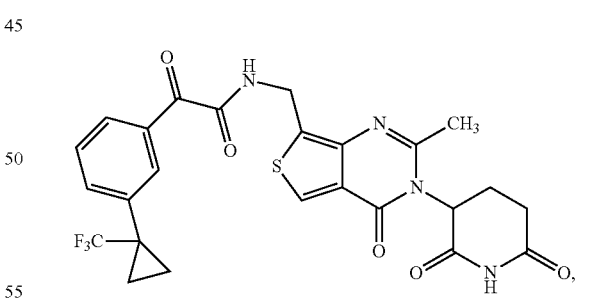
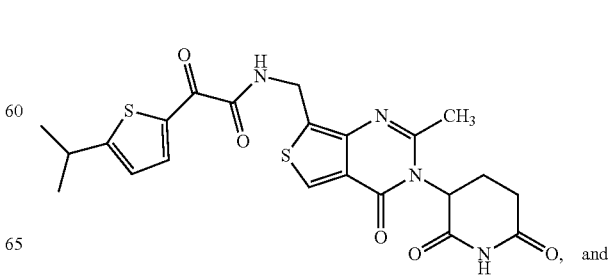

-continued

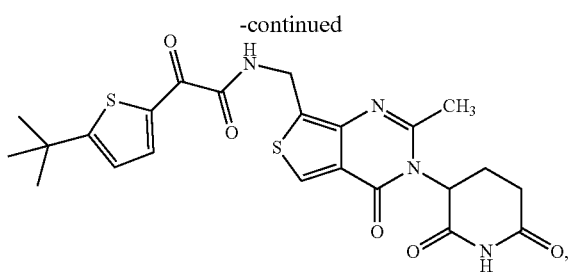

and pharmaceutically acceptable salts thereof.

25. The compound of claim 1, wherein the compound of Formula (I) is represented by Formula (Ia), (Ib), or (Ic):

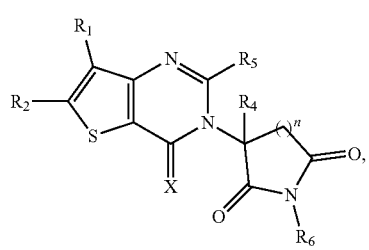
(Ia)

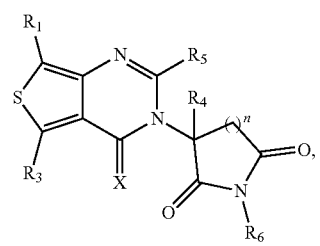
(Ib)

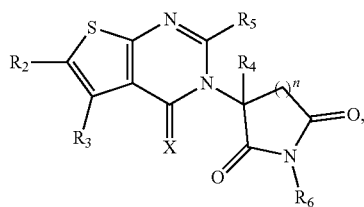
(Ic)

or a pharmaceutically acceptable salt thereof.

26. The compound of claim 25, wherein n is 2.
27. The compound of claim 25, wherein $R_5$ is an unsubstituted $C_1$-$C_6$ alkyl.
28. The compound of claim 25, wherein $R_6$ is hydrogen, or a substituted or unsubstituted $C_1$-$C_6$ alkyl.
29. The compound of claim 25, wherein X is O.
30. The compound of claim 25, wherein each of $R_1$, $R_2$, and $R_3$ is independently hydrogen, deuterium, hydroxyl, halogen, cyano, nitro, a substituted or unsubstituted amino, a substituted or unsubstituted C-amido, a substituted or unsubstituted N-amido, a substituted or unsubstituted ester, a substituted or unsubstituted urea, a substituted or unsubstituted $C_1$-$C_6$ alkoxy, a substituted or unsubstituted $C_1$-$C_6$ alkyl, a substituted or unsubstituted $C_1$-$C_6$ haloalkyl, a substituted or unsubstituted $C_3$-$C_6$ cycloalkyl, a substituted or unsubstituted phenyl, a substituted or unsubstituted naphthyl, a substituted or unsubstituted 4-6 membered heterocyclyl, or a substituted or unsubstituted 5 or 6 membered heteroaryl.

31. The compound of claim 25, wherein the compound of Formula (I) is represented by Formula (Ia), and wherein at least one or each of $R_1$ and $R_2$ is hydrogen.
32. The compound of claim 31, wherein one of $R_1$ and $R_2$ is hydrogen and the other of $R_1$ and $R_2$ is selected from the group consisting of an unsubstituted $C_3$-$C_6$ cycloalkyl, an unsubstituted $C_1$-$C_3$ alkoxy, an unsubstituted $C_1$-$C_3$ alkyl, a $C_1$-$C_6$ alkyl substituted with $C_1$-$C_6$ alkoxy, amino, —N($C_1$-$C_3$ alkyl)$_2$, or —NH($C_1$-$C_3$ alkyl), an unsubstituted $C_1$-$C_2$ haloalkyl, a halogen, and an unsubstituted amino.
33. The compound of claim 25, wherein the compound of Formula (I) is represented by Formula (Ib), and wherein at least one or each of $R_1$ and $R_3$ is hydrogen.
34. The compound of claim 33, wherein one of $R_1$ and $R_3$ is hydrogen and the other of $R_1$ and $R_3$ is selected from the group consisting of an unsubstituted $C_3$-$C_6$ cycloalkyl, an unsubstituted $C_1$-$C_3$ alkoxy, an unsubstituted $C_1$-$C_3$ alkyl, a $C_1$-$C_6$ alkyl substituted with $C_1$-$C_6$ alkoxy, amino, —N($C_1$-$C_3$ alkyl)$_2$, or —NH($C_1$-$C_3$ alkyl), an unsubstituted $C_1$-$C_2$ haloalkyl, a halogen, and an unsubstituted amino.
35. The compound of claim 25, wherein the compound of Formula (I) is represented by Formula (Ic), and wherein at least one or each of $R_2$ and $R_3$ is hydrogen.
36. The compound of claim 35, wherein one of $R_2$ and $R_3$ is hydrogen and the other of $R_2$ and $R_3$ is selected from the group consisting of an unsubstituted $C_3$-$C_6$ cycloalkyl, an unsubstituted $C_1$-$C_3$ alkoxy, an unsubstituted $C_1$-$C_3$ alkyl, a $C_1$-$C_6$ alkyl substituted with $C_1$-$C_6$ alkoxy, amino, —N($C_1$-$C_3$ alkyl)$_2$, or —NH($C_1$-$C_3$ alkyl), an unsubstituted $C_1$-$C_2$ haloalkyl, a halogen, and an unsubstituted amino.
37. The compound of claim 1, selected from the group consisting of

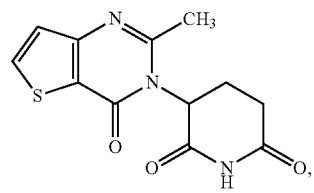

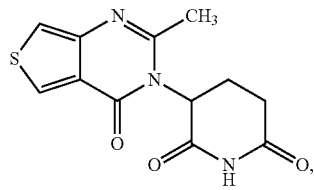

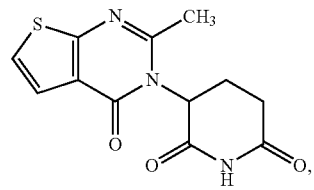

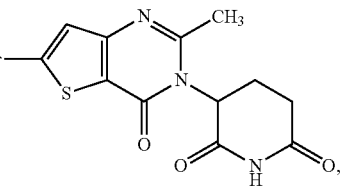

-continued

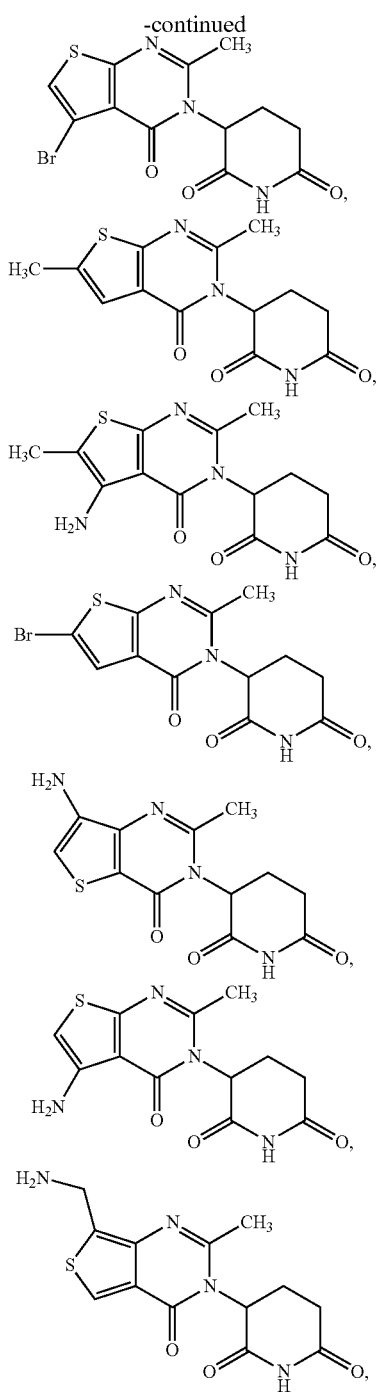

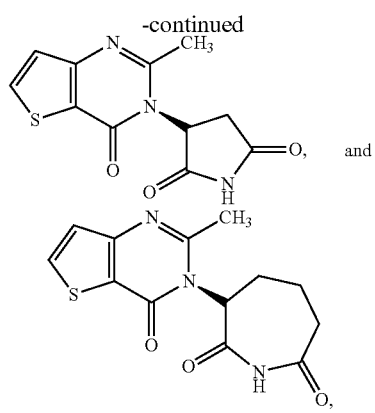

and pharmaceutically acceptable salts thereof.

38. A pharmaceutical composition comprising a compound of claim 2, or a pharmaceutically acceptable salt thereof, and one or more pharmaceutically acceptable excipients.

39. A method of inhibiting GSPT1 activity, comprising contacting a cell with a compound of claim 2, or a pharmaceutically, acceptable salt thereof.

40. A method of modulating protein activity, comprising contacting a cell with a compound of claim 2, or a pharmaceutically acceptable salt thereof, wherein the protein is selected from the group consisting of cytokine, aiolos, PDE6, ikaros, helios, and CK1α.

41. A method of treating or ameliorating a disease, disorder or condition, comprising administering a therapeutically effective amount of a compound of claim 2, or a pharmaceutically acceptable salt thereof to a subject in need thereof, and wherein the disease, disorder or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer.

42. The method of claim 40, wherein the cytokine is selected from the group consisting of IL-1β, IL-6, TNFα, and IL-2, and combinations thereof.

43. The method of claim 41, wherein the disease, disorder or condition is cancer.

44. The method of claim 43, wherein the cancer is selected from the group consisting of a breast cancer, lung cancer, leukemia, lymphoma, hepatocellular carcinoma, gastric cancer, prostate cancer and astrogliosis, and combinations thereof.

* * * * *